US00RE36385E

United States Patent [19]

Toda et al.

[11] E Patent Number: Re. 36,385

[45] Reissued Date of Patent: Nov. 9, 1999

[54] GLUCOPYRANOSE DERIVATIVES

[75] Inventors: Masaaki Toda; Yutaro Sasaki, both of Osaka; Katsuichi Shimoji, Kyoto, all of Japan

[73] Assignee: Ono Pharmaceutical Co., Ltd., Oaska, Japan

[21] Appl. No.: 08/064,549

[22] Filed: May 20, 1993

Related U.S. Patent Documents

Reissue of:

[64] Patent No.: 4,925,929
Issued: May 15, 1990
Appl. No.: 07/338,090
Filed: Apr. 14, 1989

[U.S. Applications:

[63] Continuation-in-part of application No. 06/938,308, Dec. 5, 1986, abandoned, and application No. 07/188,873, May 2, 1988, abandoned.

[30] Foreign Application Priority Data

| | | | |
|---|---|---|---|
| Dec. 6, 1985 | [JP] | Japan | 60-273440 |
| Sep. 6, 1986 | [JP] | Japan | 61-210379 |
| May 1, 1987 | [JP] | Japan | 62-106298 |

[51] Int. Cl.[6] ..... A61K 31/00; C07H 13/00; C07H 11/00; C07D 309/00

[52] U.S. Cl. ..... 536/4.1; 536/17.2; 536/17.5; 536/54; 536/118; 536/122; 514/885

[58] Field of Search ..... 536/4.1, 118, 122, 536/54, 17.2, 17.5; 514/25, 885

[56] References Cited

U.S. PATENT DOCUMENTS

| | | | |
|---|---|---|---|
| 4,304,903 | 12/1981 | Nair et al. | 536/118 |
| 4,374,831 | 2/1983 | Joseph et al. | 536/4.1 |
| 4,399,126 | 8/1983 | Schaub et al. | 536/118 |
| 4,536,572 | 8/1985 | Kim et al. | 536/17.2 |

FOREIGN PATENT DOCUMENTS

| | | |
|---|---|---|
| 59-300644 | 11/1984 | Japan . |
| 87180608 | 11/1985 | Japan . |
| 61-056865 | 2/1986 | Japan . |
| 61-193402 | 6/1986 | Japan . |
| 61-193403 | 6/1986 | Japan . |
| 61-198197 | 7/1986 | Japan . |
| 61-226883 | 8/1986 | Japan . |
| 61-321410 | 8/1986 | Japan . |
| 61-007348 | 12/1986 | Japan . |
| 8-308545 | 10/1996 | Japan . |
| WO 8404526 | 11/1984 | WIPO . |

OTHER PUBLICATIONS

Agricultural and Biological Chemistry, vol. 48, No. 1, Jan. 1984, pp. 251–252.
"Synthesis of biologically active, novel monosaccharide analogs of lipid A".
Chemical & Pharmaceutical Bulletin, vol. 33, No. 10, Oct. 1985, pp. 4621–4624.
"Antitumor activity and biological effects of chemically synthesized etc".
Sobel et al., "Steryl Sulfates. II. Isolation and Separation of Sterols," J. Am. Chem. Soc., 64, 361 (1942).
Tetrahedron Letters, vol. 26, No. 12, pp. 1545–1548, 1985, Great Britain.

*Primary Examiner*—Ronald W. Griffin
*Assistant Examiner*—Everette White
*Attorney, Agent, or Firm*—Sughrue, Mion, Zinn, Macpeak & Seas

[57] ABSTRACT

This invention relates to glucopyranose compounds of formula (I) and (IA)

(I)

(IA)

and the non-toxic salts thereof wherein the substituents are as defined herein. Such materials possess enhancing activity of cellular immunity (e.g. mitogenic activity) to living tissue and therefore are useful as anti-tumor agents.

29 Claims, No Drawings

GLUCOPYRANOSE DERIVATIVES

Matter enclosed in heavy brackets [ ] appears in the original patent but forms no part of this reissue specification; matter printed in italics indicates the additions made by reissue.

CROSS-REFERENCE TO RELATED APPLICATIONS

This application is a continuation in part, of U.S. application Ser. No. 938,308, filed Dec. 5, 1986, now abandoned and U.S. application Ser. No. 188,873 filed May 2, 1988, now abandoned.

FIELD OF THE INVENTION

This invention relates to glucopyranose derivatives.

More particularly, this invention relates to (1) novel glucopyranose derivatives (compounds);
(2) processes for their preparation; and
(3) immunity-enhancing agents and/or anti-tumor agents containing as active ingredient the present derivatives.

BACKGROUND OF THE INVENTION

Gram-negative germs (e.g. cholera germs, salmonella germs, colon bacillus) have compounds known as lipopolysaccharides (abbreviated as LPS) on the outer cell membrane, and it was thought that such compounds induced endotoxin shock.

It was known that LPS have various bioactivities including fetal toxicity; this is why it is so named an endotoxin. For example, LPS have a pyrogenetic action, a hemorrhage action, can induce encephalomyelitis, arthritis, and have a blastogenic action (macrophage activating action, B cell mitogenic activity, producing action of non-specific antibody, enhancing activity of cellular immunity etc.) and anti-tumor action (INF (interferon) inducing action, TNF (tumor necrosis factor) inducing action etc.).

Especially, LPS is effective as a non-specific immunity agent, and has an action inducing hemorrhage necrosis of tumor cells specifically by its TNF inducing activity, and therefore can be useful as an anti-tumor agent.

LPS is also useful for its inducing activity of IL-1 (interleukin-1) or interferon, not only enhancing its activity of cellular immunity but also stimulating of NK (natural killer) activity.

On the other hand, LPS is constituted from three kinds of materials, i.e. acidic protein, macromolecular polysaccharides and phospholipid, and the phospholipid but has been found as its active site by Westphal, Lüdertz et al.

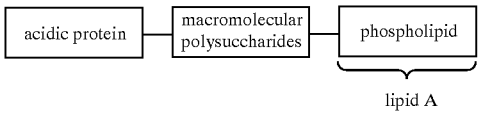

The phospholipid shown above is called lipid A, and it was known that lipid A alone possesses various activities like LPS.

The absolute structure of lipid A was unknown for many years, but recent studies have made clear that its structure is a disaccharideamine combined with fatty acids and phosphoric acids as shown below. See Nippon Saikin-gaku Zasshi 40(1), 57 (1985) and Proc. Natl. Acad. Sci. U.S.A., 80, 4624 (1983):

Lipid A of *E. Coli*

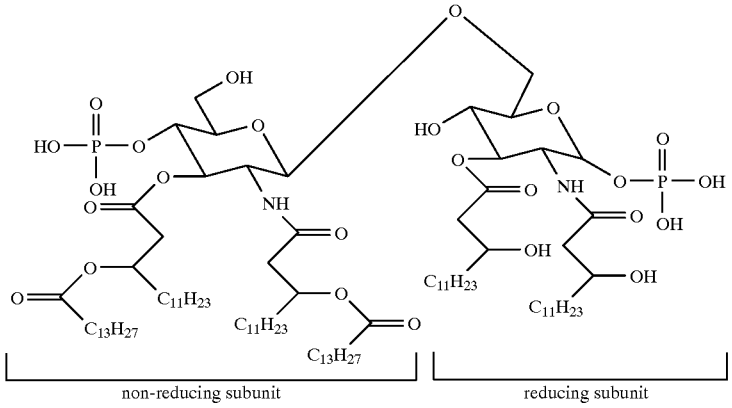

As a result of these recent studies, it has been discovered that each subunit above possesses activities like lipid A. In particularly, the reducing subunit was isolated as a biosynthesis precursor and was named lipid X. See Biol. Chem., 256, 10690 (1981) and Proc. Natl. Acad. Sci., 80, 4624 (1983).

Futher, a compound combined with a hexadecanoyl group on the hydroxy group of the β-hydroxytetradecanoyl group on the 2nd position of lipid X as ester is named lipid Y.

Patent applications have been filed on the above lipid A, lipid X and lipid Y by Wisconsin Alumni Research Foundation. See WO-8404526 or EP-143840.

Non-reducing subunits were not found to be naturally occuring, and some of them were synthesized chemically, i.e. compounds of general formula:

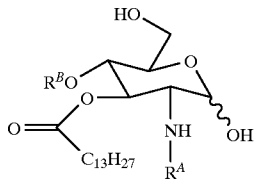

Examples are:

Compound 1:

$R^1$=

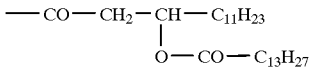

$R^2$=—H

Compound 2:

$R^1$=—CO—$C_{13}H_{27}$ $R^2$=—PO(OH)$_2$

Compound 3:

$R^A$1=

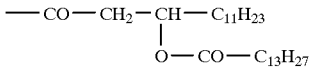

$R^2$=—PO(OH)$_2$

See Agric. Biol. Chem., 48(1), 251 (1984) and FEBS LETT., 167, 226 (1984).

Patent applications relating to the above compounds have been published. See Japanese Patent Publication No. 61-126093 and 61-126094.

Further, compounds replacing the hydroxy group on the 1st position with a hydrogen atom has benn described, i.e. compounds of general formula:

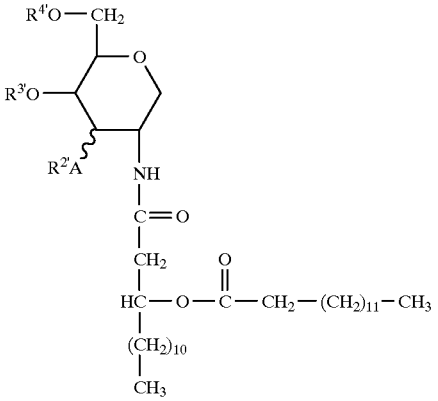

wherein A represents O or NH, $R^{2'}$ represents $C_{14}$ or $C_{14}$-O-$C_{14}$, $R^{3'}$ and R4' represent a hydrogen atom or P, $C_{14}$ represents a tetradecanoyl group, $C_{14}$-O-$C_{14}$ represents a (3-tetradecanoyl)-tetradecanoyl group, and P represents a phosphoryl group, respectively. Stereo configuration of $AR^{2'}$ on the 3rd position is α-configuration or β-configuration. See Japanese Patent Publication No. 61-172867.

SUMMARY OF THE INVENTION

We, the present inventors, succeeded in synthesizing novel compounds by introducing the following chemical modifications into a non-reducing subunit:

(1) conversion of the phosphoric acid residue on the 4th position into a sulfuric acid residue, (2) introduction an aryl group (benzene ring or naphthalene ring) into the terminal of the acyl chain on the 2nd and 3rd positions, (3) conversion of the hydroxy group on the 1st position into a hydrogen atom in some compounds, (4) conversion of the hydroxymethyl group on the 5-position into a methyl group, hydrogen atom or a sulfoxymethyl group (—$CH_2OSO_3H$) in some compounds, and we confirmed that these novel compounds possess excellent pharmacological activities like lipid-A. The present invention was thus achieved.

That is, the present invention relates to glucopyranose compounds of general formulae (I) and (IA):

(I)

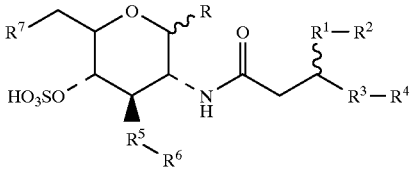

wherein

R represents a hydrogen atom, a hydroxy group or an alkoxy group of from 1 to 4 carbon atom(s);

$R^1$ represents a single bond or an oxycarbonylalkylene group of from 2 to 20 carbon atoms;

$R^2$ and $R^6$, independently, represent a hydrogen atom or a general formula:

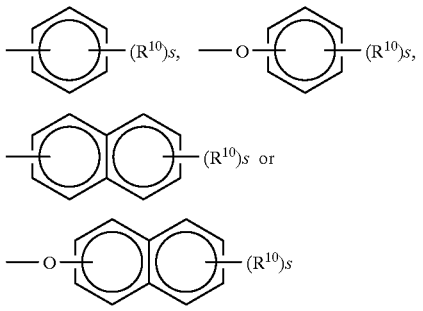

(wherein $R^{10}$ represents a hydrogen atom, an alkyl or alkoxy group of from 1 to 7 carbon atom(s) or a halogen atom, and s represents 1, 2 or 3), respectively;

$R^3$ represents an alkylene group of from 1 to 20 carbon atom(s);

$R^4$ represents a hydrogen atom or a general formula:

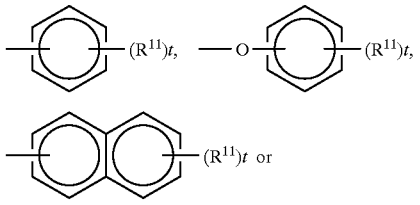

-continued

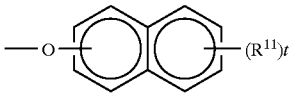

(wherein $R^{11}$ represents a hydrogen atom, an alkyl or alkoxy group of from 1 to 7 carbon atom(s) or a halogen atom, and t represents 1, 2 or 3);

$R^5$ repesents an oxycarbonylalkylene group of from 2 to 20 carbon atoms; and $R^7$ represents a hydrogen atom or a hydroxy group;

with the proviso that $R^2$, $R^4$ and $R^6$ do not represent hydrogen atoms at the same time;

(IA)

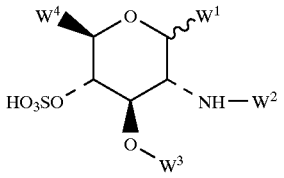

wherein $W^1$ represents a hydrogen atom, a hydroxy group or an alkoxy group of from 1 to 4 carbon atom(s);

$W^2$ represents a group represented by A, B, D or E:

A represents a general formula:

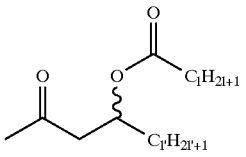

B represents a general formula:

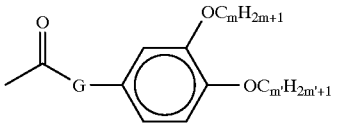

D represents a general formula:

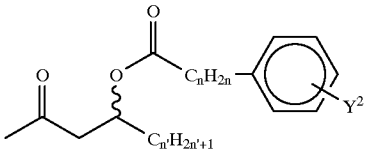

and

E represents a general formula:

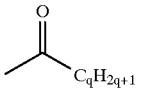

(in each of A, B, D and E, l and q each represents an integer of 11~15, m and m' each represents an integer of 6~12, n represents an integer of 6~10, l' and n' each represents an integer of 9~13, G represents a single bond or an alkylene group of from 1 to 4 carbon atom(s), $Y^2$ represents a hydrogen atom, an alkyl or alkoxy group of from 1 to 7 carbon atom(s) or a halogen atom);

$W^3$ represents a group represented by L, M or Q:

L represents a general formula:

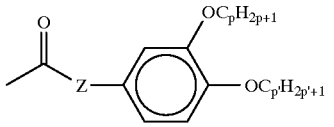

M represents a general formula:

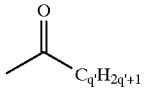

and

Q represents a general formula:

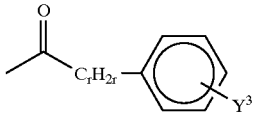

(in each of L, M and Q, Z represents a single bond or an alkylene group of from 1 to 4 carbon atom(s), p and p' each represents an integer of 6~12, q' represents an integer of 11~15, r represents an integer of 6~10, $Y^3$ represents a hydrogen atom, an alkyl or alkoxy group of from 1 to 7 carbon atom(s) or a halogen atom);

$W^4$ represents a hydrogen atom, hydroxymethyl group or sulfoxymethyl group;

with the proviso that when $W^4$ represents hydroxymethyl group, (A,M), (A,Q), (D,M), (D,Q), and (E,M) as the combination of ($W^2$, $W^3$) are excluded, and when $W^4$ represents sulfoxymethyl group, (A,M) and (E,M) as the combination of ($W^2$, $W^3$) are excluded;

non-toxic salts of these derivatives, processes for their preparation, and immunity enhancing agents and/or anti-tumor agents containing as active ingredient a compound of formula (I) or (IA).

DETAILED DESCRIPTION OF THE INVENTION

In general formula (I) and (IA), examples of the alkoxy group of from 1 to 4 carbon atom(s) as R and $W^1$ are methoxy, ethoxy, propoxy and butoxy groups and isomeric groups thereof, and preferred groups as R and $W^1$ are a hydrogen atom, a hydroxy group and a methoxy group.

In general formula (I), the oxycarbonylalkylene group of from 2 to 20 carbon atoms as $R^1$ and $R^5$ is a group of general formula:

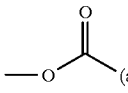

(alkylene group of from 1 to 19 carbon atom(s))- and alkylene chain side is bonded to $R^2$ and $R^6$ group respectively. Suitable alkylene group of 1 to 19 carbon atom(s) include methylene, ethylene, trimethylene, tetramethylene, pentamethylene, hexamethylene, heptamethylene, octamethylene, nonamethylene, decamethylene, undecamethylene, dodecamethylene, tridecamethylene, tetradecamethylene, pentadecamethylene, hexadecamethylene, heptadecamethylene, octadecamethylene and nonadecamethylene groups and isomeric groups thereof, and preferred groups as $R^1$ are a single bond (a hydrogen atom as $R^2$ is preferable, in this case), oxycarbonyltrimethylene, oxycarbonyltetramethylene, oxycarbonylhexamethylene, oxycarbonylheptamethylene, oxycarbonyloctamethylene, oxycarbonylnonamethylene, oxycarbonyldecamethylene and oxycarbonyldodecamethylene groups.

In the general formula (I) and (IA), examples of the alkyl or alkoxy group of from 1 to 7 carbon atom(s) as $R^{10}$ in the group represented by $R^2$ and $R^6$, $R^{11}$ in the group represented by $R^4$, $Y^2$ in the group represented in D and as $Y^3$ in the group represented in Q, are methyl, ethyl, propyl, butyl, pentyl, hexyl, heptyl, methoxy, ethoxy, propoxy, butoxy, pentyloxy, hexyloxy and heptyloxy groups and isomeric groups thereof. Halogen atoms represented by $R^{10}$, $R^{11}$, $Y^2$ and $Y^3$ are fluorine, chlorine, bromine and iodine atoms, and prefered groups as $R^{10}$ and $R^{11}$ are a hydrogen atom, chlorine atom, methoxy group and pentyl group. And prefered groups as $Y^2$ and $Y^3$ are hydrogen atom.

In general formula (I), examples of the alkylene group of from 1 to 20 carbon atom(s) for $R^3$ are methylene, ethylene, trimethylene, tetramethylene, pentamethylene, hexamethylene, heptamethylene, octamethylene, nonamethylene, decamethylene, undecamethylene, dodecamethylene, tridecamethylene, tetradecamethylene, pentadecamethylene, hexadecamethylene, heptadecamethylene, octadecamethylene and nonadecamethylene and eicosamethylene groups and isomeric groups thereof, and prefered groups as $R^3$ especially are hexamethylene and undecamethylene groups.

In the groups represented by $W^2$ and $W^3$ in general formula (IA):

(i) the alkyl groups represented by $—C_lH_{2l+1}$, $—C_qH_{2q+1}$ and $—C_{q'}H_{2q'+1}$ are undecyl, dodecyl, tridecyl, tetadecyl and pentadecyl groups, of which the carbon number is from 11 to 15, and isomeric groups thereof, and a more prefered group is a tridecyl group;

(ii) the alkyl groups represented by $—C_mH_{2m+1}$, $—C_{m'}H_{2m'+1}$, $—C_pH_{2p+1}$ and $—C_{p'}H_{2p'+1}$ are hexyl, heptyl, octyl, nonyl, decyl, undecyl and dodecyl group, of which the carbon number is from 6 to 12, and isomeric groups thereof, and a more prefered group is a decyl group;

(iii) the alkylene groups represented by $—C_nH_{2n}$ and $—C_rH_{2r}$ are hexamethylene, heptamethylene, octamethylene, nonamethylene and decamethylene groups, of which the carbon number is from 6 to 10, and isomeric groups thereof, and a more prefered group is an octamethylene group;

(iv) the alkylene groups of from 1 to 4 carbon atom(s) as G and Z, are methylene, ethylene, propylene and butylene group and isomeric groups thereof. More preferred group as G and Z is a single bond.

In general formula (IA), the alkyl groups represented by $—C_{l'}H_{2l'+1}$ and $—C_{n'}H_{2n'+1}$ in the groups represented by $W^2$, are nonyl, decyl, undecyl, dodecyl and tridecyl, of which the carbon number is from 9 to 13, and isomeric groups thereof, and a more preferable group is an undecyl group.

More preferred groups as $W^2$ and $W^3$ each are the group represented by B and L.

In general formula (I) and (IA), all of the groups defined above for $R^7$ and $W^4$ are preferable.

The alkyl, alkylene and alkenylene groups described above include straight and branched chain groups, and preferred groups especially are straight chain.

The compounds of the present invention of general formulae (I) and (IA) possess activities like lipid A, and therefore are useful as immunity enhancing agents and anti-tumor agents. More concretely the compounds of the present invention possess properties of activating macrophages, B cell mitogenic activity, producing action of non-specific antibody, enhancing activity of cellular immunity, as examples of blastogenic activities, and possess the properties of INF (interferon) inducing action, TNF (tumor necrosis factor) inducing action etc. as examples of anti-tumor activities. The compounds also possess producing action of interleukin and stimulating action of NK (natural killer) activity.

The present invention is concerned with all compounds of general formulae (I) and (IA) in the "natural" form or its enantiomeric form, or mixtures thereof, more particularly the racemic form consisting of equimolecular mixtures of the natural and its enantiomeric form.

As will be apparent to those of ordinary skill in the art, the compounds depicted in general formulae (I) and (IA) have at least five centers of chirality.

This is, when the carbon atoms of the 1-, 2-, 3-, 4- and 5-positions of the sugar skeleton and the alkyl or alkylene groups represented by R, $R^1$, $R^3$, $R^5$, $W^1$, $W^2$ or $W^3$ are branched-chain, it is possible to occur the centers of chirality.

The presence of chirality leads, as is well known, to the existence of isomerism.

Thus, all isomers and mixtures thereof which have those side-chains attached to the sugar ring carbon atoms in positions 2 and 4 in the cis-configuration and those side-chains attached to the sugar ring carbon atoms in positions 3 and 5 in the cis-configuration, being such a configuration that the former side-chains (those in position 2 and 4) and the latter side-chains (those in position 3 and 5) are trans with respect to each other and have R or $W^1$ groups in the 1-position of sugar are to be considered within the scope of the present invention.

METHODS FOR PREPARING COMPOUNDS OF FORMULAE (I) AND (IA)

The present invention not only pertains to chemical compounds per se and non-toxic salts thereof, but also encompasses processes for their preparation.

According to present invention, among the compounds of the present invention of general formula (I), compounds wherein $R^7$ is a hydroxy group, of general formula:

(Ia)

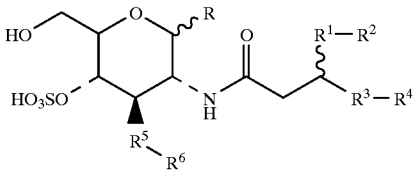

(wherein, all of the symbols have the same meanings as hereinbefore defined)

may be prepared by hydrolizing a compound of general formula:

(II)

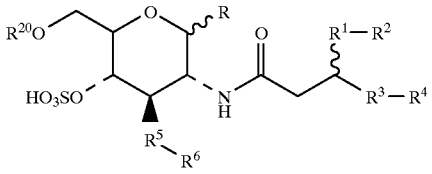

(wherein $R^{20}$ represents a trialkylsilyl group, and the other symbols have the same meaning as hereinbefore defined)

in an acidic condition.

Hydrolysis is well known and can be conducted, for example, using an acid (acetic acid, oxalic acid, trifluoroacetic acid, hydrochloric acid etc.), in a water-miscible organic solvent (THF, methanol, ethanol, dioxane etc.), with or without water, at a temperature of from 0° C. to 70° C.

On the other hand, among the compounds of general formula (I), compounds wherein $R^7$ is a hydrogen atom, of general formula:

(Ib)

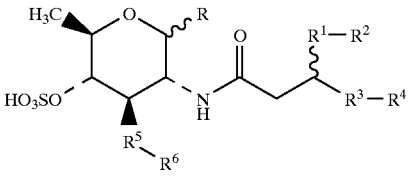

(wherein, all of the symbols have the same meaning as hereinbefore defined)

may be prepared by introducing a sulfo group into the hydroxy group of the 4th-position of a compound of general formula:

(III)

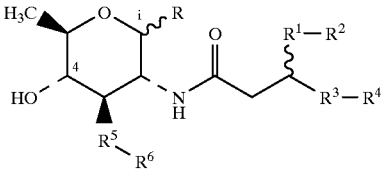

(wherein, all of the symbols have the same meaning as hereinbefore defined).

Such a reaction procedure is well known, and may be carried out, for example, in the presence of a tertiary amine (pyridine, triethylamine etc), in an inert organic solvent (THF, methylene chloride, ethyl acetate etc.) or in the absence of a solvent, using a sulfur trioxide-pyridine complex, at a temperature of from −10° C. to 60° C.

The reaction using the compound of the general formula (III) wherein R is a hydroxy group leads to the production of small amounts of by-product in which the sulfoxy groups are introduced at 1-position as well as at the 4-position. The by-product may be removed by purification described hereinafter.

Among the compounds of the general formula (II) and (III), compounds wherein R is a hydroxy group, of general formula (IIa) and (IIIa) may be prepared by the series of reaction steps described in the following scheme (A).

Scheme (A)
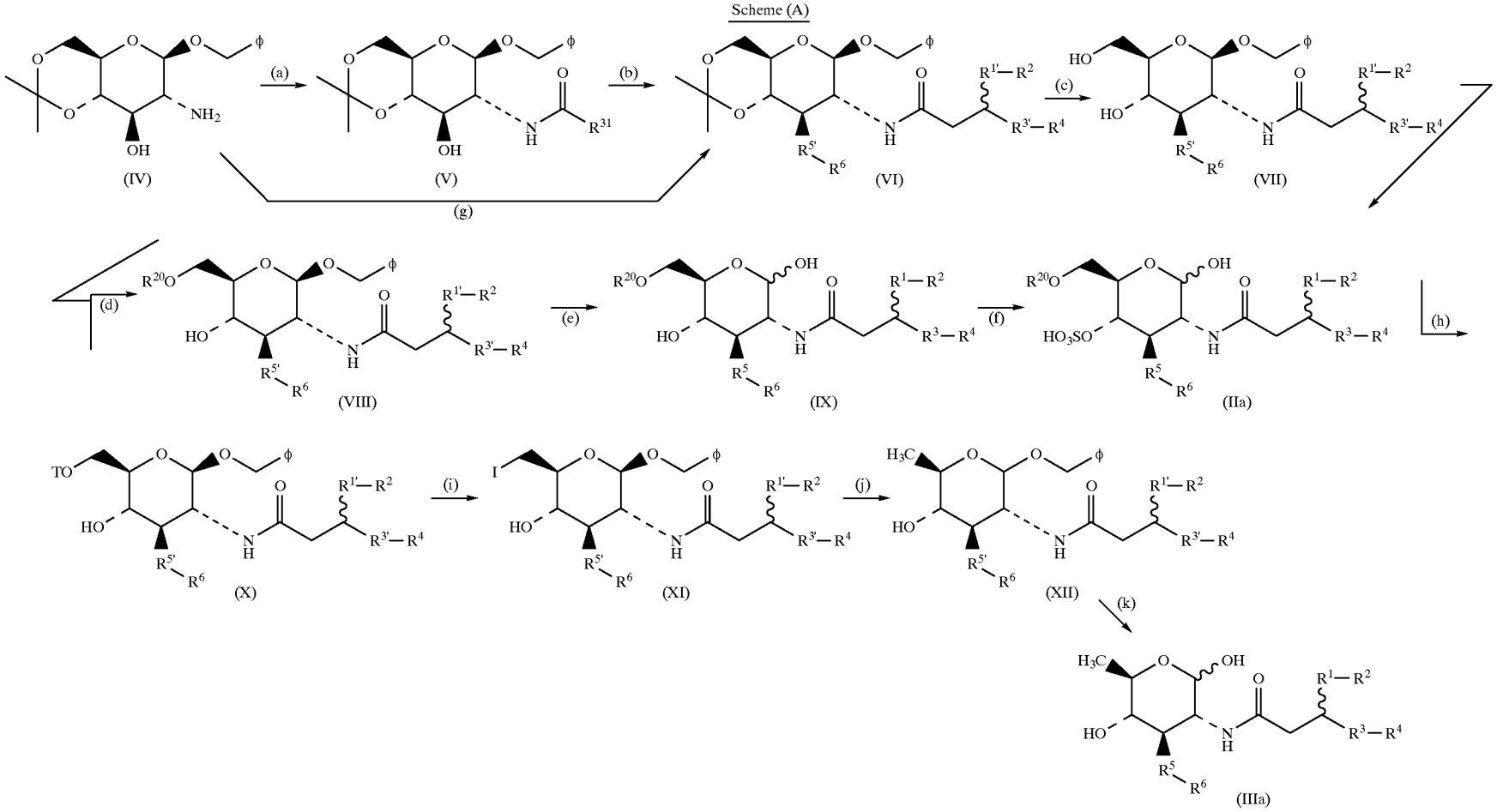

Each of the symbols in the scheme (A) represent the following meanings or have been defined hereinbefore respectively.

$R^{1'}$—a single bond or an oxycarbonylalkylene or oxycarbonylalkenylene group of from 2 to 20 arbon atoms, $R^{3'}$—an alkylene or alkenylene group of from 1 to 20 carbon atom(s), $R^{5'}$—an oxycarbonylalkylene or oxycarbonylalkenylene group of from 2 to 20 carbon atoms, $R^{31}$—a group of general formula:

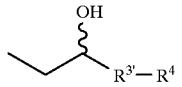

or

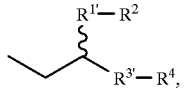

T—methanesulfonyl group or p-toluenesulfonyl group,

I—iodine atom.

In scheme (A), each of the reaction steps are known per se, and summarized descriptions are as follows:

Step (a) is an introducing reaction of an acyl group into the amino group, i.e. N-acylation, and it may be carried out, for example, using a mixed acid anhydride which was prepared from a carboxylic acid of general formula:

(XIII)

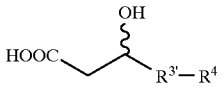

or (XIV)

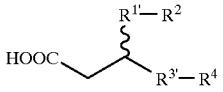

by reacting with pivaloyl chloride, in the presence of a suitable base (triethylamine, pyridine etc.), in an inert organic solvent (methylene chloride, toluene, benzene, hexane, THP, THF, etc.), at a temperature of from −30° C. to 30° C., in the same condition without purification.

N-acylation described above may be carried out by reacting a compound of the general formula (IV) and a carboxylic acid of the general formula (XIII) or (XIV), in the presence of a suitable base (triethylamine, pyridine, 4-(N,N-dimethylamino) pyridine etc.) in an inert organic solvent (methylene chloride, acetonitrile etc.), using 2-chloro-N-methylpyridinium iodide, at a temperature of from −30° C. to 30° C.

Further, N-acylation also may be carried out by reacting a carboxylic acid of the general formula (XIII) and (XIV) in the presence of triphenylphosphine, in an inert organic solvent (methylene chloride, THF, ethyl acetate etc.), using 2,2'-pyridyldisulfide, at a temperature of from −10° C. to 50° C.

N-acylation may be carried out by other methods of activating carboxylic acids, for example, using dicyclohexylcarbodiimide.

In this N-acylation, using the compound of the general formula (XIII) produces a compound of the general formula (IIa) wherein the substituents —$R^1$—$R^2$ and the substituents —$R^5$—$R^6$ are the same groups.

Step (b) is an introducing reaction of and acyl group into the hydroxy group, i.e. O-acylation, and it may be carried out, for example, in the presence of a suitable base (triethylamine, 4-(N,N-dimethylamino)pyridine, pyridine etc.), in an inert organic solvent (methylene chloride, toluene, benzene, ethyl acetate, hexane, THF, THP etc.) or in the absence of a solvent, using a corresponding acyl halide, at a temperature of from −10° C. to 60° C.

O-acylation may be carried out by reacting a corresponding acid, in the presence of a suitable amine (triethylamine, 4-(N,N-dimethylamino)pyridine, pyridine etc.) in an inert organic solvent (methylene chloride, acetonitrile etc.), using 2-chloro-N-methylpyridinium iodide as a condensing agent, at a temperature of from −30° to 30° C.

Further, O-acylation may also be carried out by other methods of activating carboxylic acid, for example, using dicyclohexylcarbodiimide.

Step (c) is a removing reaction of isopropylidene groups on the 4th and 6th positions of the sugar as protecting group, and it may be carried out, for example, in water or a water miscible organic solvent (THF, methanol, ethanol etc.) and water, using an acid (acetic acid, p-toluenesulfonic acid, camphorsulfonic acid, trichloroacetic acid, oxalic acid etc.), at a temperature of from 0° C. to 80° C.

Step (d) is an introducing reaction of a protecting group into the hydroxy group on the 6th position selectively, and it may be carried out, for example, in the presence of a suitable base (4-(N,N-dimethylamino)pyridine, pyridine, triethylamine etc.), in an inert organic solvent (methylene chloride, toluene, benzene, ethyl acetate, hexane, THF, THP etc.) or without a solvent being used, using a corresponding trialkylsilyl halide (t-butyldimethylsilyl chloride, trimethylsilyl chloride etc.), at a temperature of from −10° C. to 60° C.

Step (e) is a removing reaction of a benzyl group, and it may be carried out, for example, in an atmosphere of hydrogen, in an organic solvent (methanol, ethanol, THF, THP etc.), using a hydrogenating catalyst (palladium-carbon, platinum black, nickel etc.), at a temperature of from −10° C. to 80° C.

Step (f) is an introducing reaction of a sulfo group into the hydroxy group on the 4th position, and it may be carried out, for example, in the presence of a tertiary amine (pyridine, triethylamine etc.), in an inert organic solvent (THF, methylene chloride, ethyl acetate etc.) or in the absence of a solvent, using sulfur trioxide-pyridine complex, at a temperature of from −10° C. to 60° C.

Step (g) is acylation of the amino group on the 2nd position and the hydroxy group on the 3rd position at the same time, and it may be carried by the same procedure as described in step (b).

Step (h) is tosylation (an introducing reaction of a p-toluenesulfonyl group) or mesylation (an introducing reaction of a methanesulfonyl group), and it may be carried out, for example, in an inert organic solvent (methylene chloride etc.) or without a solvent being used, in the presence of tertiary amine (triethylamine, pyridine, 4-(N,N-dimethylamino)pyridine etc.), using tosyl halide or mesyl halide, at a temperature of from −40° C. to 40° C.

Step (i) is a replacing reaction of a tosyloxy or a mesyloxy group into an iodine atom, and may be carried out, for example, in an inert organic solvent (acetone etc.), using an iodide (sodium iodide, potassium iodide etc.), at a temperature of from 0° C. to 60° C.

Step (j) is a removing reaction of the iodine atom, and it may be carried out, for example, in an inert organic solvent (toluene, benzene, xylene etc.), in the presence of tributylstannane and α,α'-azobisisobutyronitrile, by irradiation of light.

Step (k) is a removing reaction of a benzyl group, and it may be carried out by the same procedure as described in step (e).

Compounds of general formula (II) or (III) wherein R is a hydrogen atom or an alkoxy group of from 1 to 4 carbon atom(s) can be prepared by using compounds of general formula:

(XV)

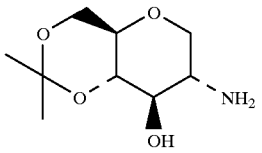

or (XVI)

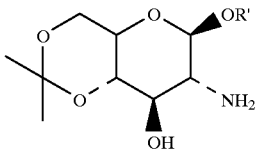

(wherein R' represents an alkyl group of from 1 to 4 carbon atom(s)) as starting material instead of the compounds of the general formula (IV) shown in the scheme (A).

In this case, reaction step (e) or (k) should be omitted, and the substituents defind with prime ($R^{1'}$, $R^{3'}$ and $R^{5'}$) and understood as the same substituents without prime ($R^1$, $R^3$ and $R^5$).

On the other hand, among the compounds of the general formula (IA), compounds wherein $W^4$ is a hydrogen atom, of the general formula:

(IAa)

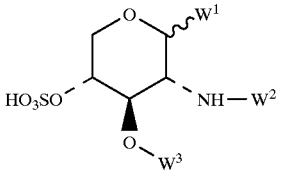

(wherein all of the symbols have the same meaning as defined hereinbefore)

may be prepared from a compound of general formula:

(IIIA)

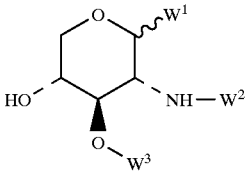

(wherein all of the symbols have the same meaning as defined hereinbefore)

by the same method for the preparation of a compound of general formula (Ib) from a compound of the general formula (III).

Further, the compounds of general formula (IA) wherein $W^4$ is a sulfoxymethyl group (—$CH_2OSO_3H$), that is, a compound of general formula:

(IAb)

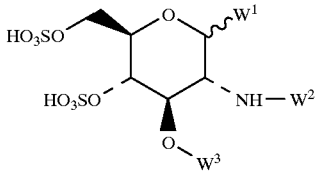

(wherein all of the symbols have the same meaning as defined hereinbefore)

may be prepared by introducing sulfo groups into the hydroxy groups of the 4- and 6-positions of a compound of general formula:

(IIIB)

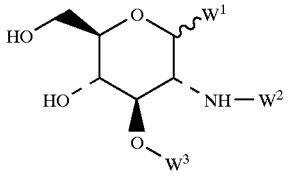

(wherein all of the symbols have the same meaning as defined hereinbefore).

This reaction may be carried out by the same method described hereinbefore, by using a two-fold amount of sulfur trioxide-pyridine complex required when introducing a sulfo group only into the 4-position.

Further, compounds of general formula (IA) wherein $W^4$ is hydroxymethyl group (—$CH_2OH$); that is, a compound of general formula:

(IAc)

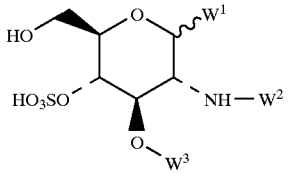

(wherein all of the symbols have the same meaning as defined hereinbefore)

may be prepared from a compound of general formula:

(IIA)

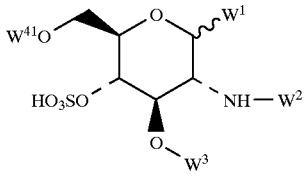

(wherein $W^{41}$ represents a trialkylsilyl group, the other symbols have the same meaning as defined hereinbefore)

by the method for the preparation of a compound of general formula (Ia) from a compound of general formula (II).

A compound of general formula (IIIA) may be prepared by the series of reaction steps described in the following scheme (B), and a compound of general formula (IIIB) and compounds of general formulae (IIAa) and (IIAb) within general formula (IIA) may be prepared by the series of reaction steps described in the following scheme (C).
Scheme (B)
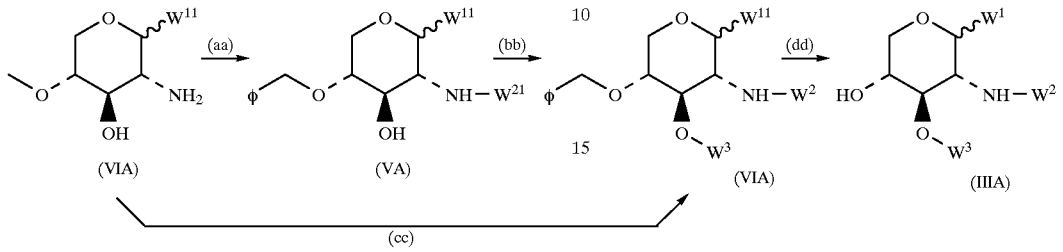

Scheme (C)
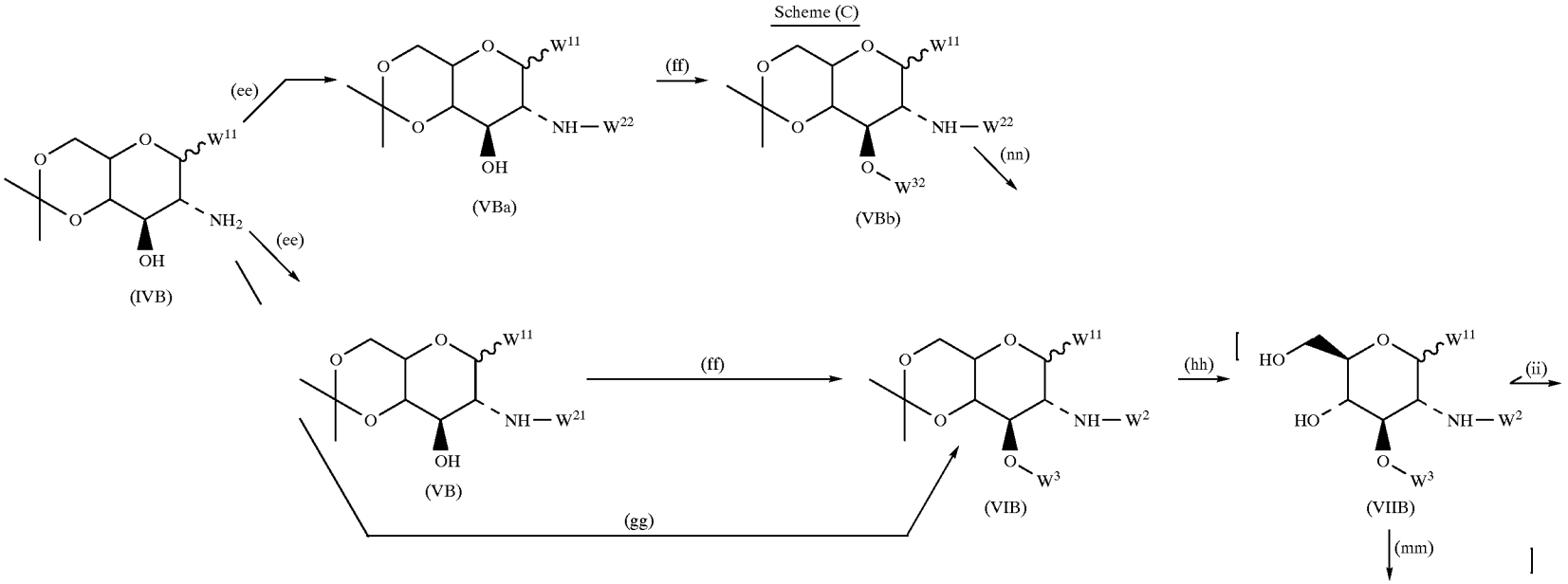

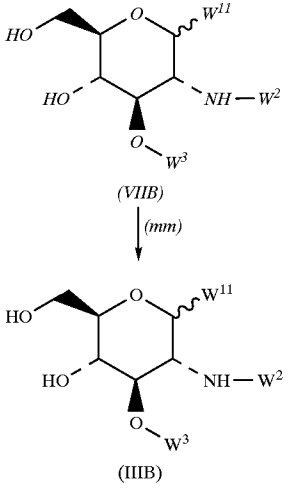
-continued
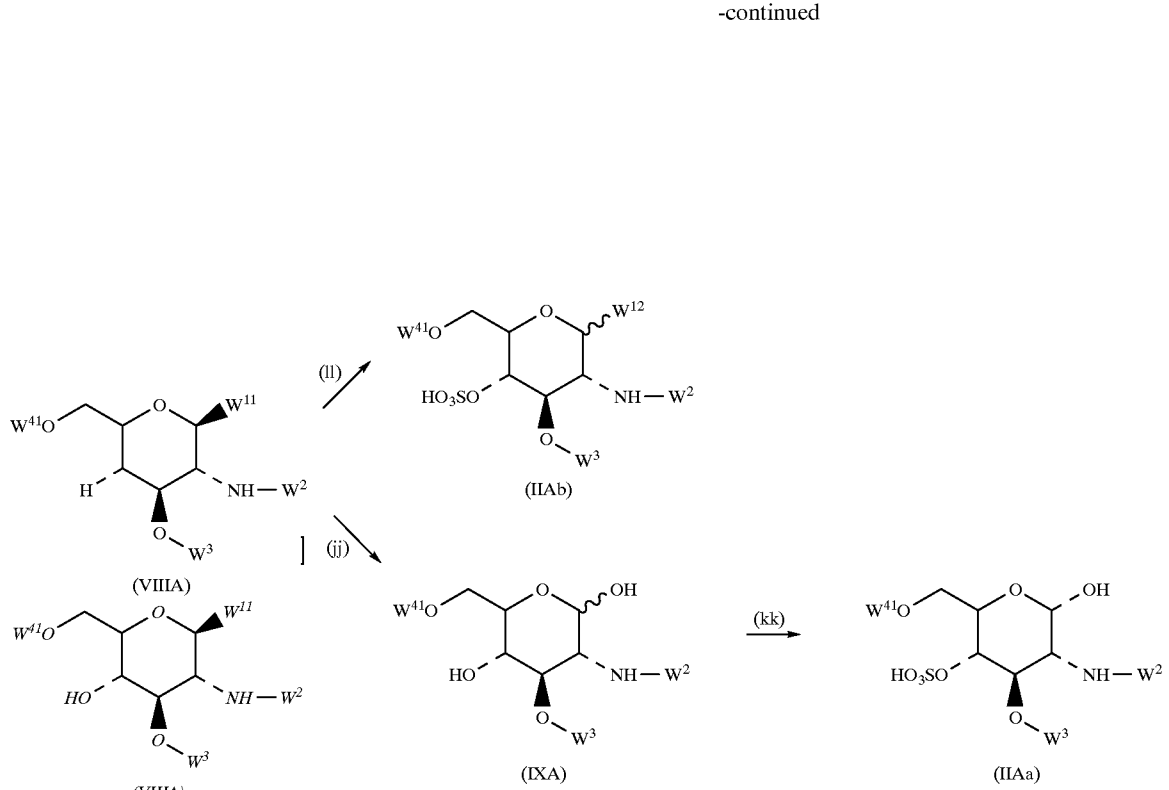

Each of the symbols in the schemes (B) and (C) represent the following meanings or are as defined hereinbefore respectively, and the other symbols have same meaning as defined hereinbefore.

$W^{11}$—hydrogen atom, benzyloxy group or alkoxy group of from 1 to 4 atom(s), $W^{21}$—a group of general formula:

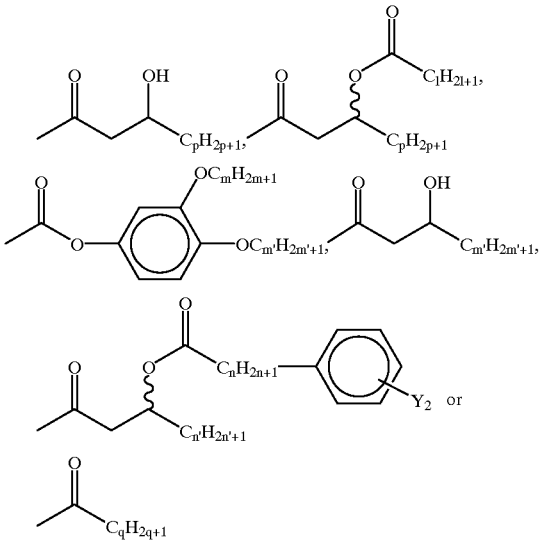

$W^{22}$, $W^{32}$—being same or different, a group of the general formula:

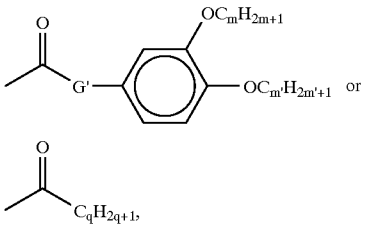

with the provisio that, when one group of $W^{22}$ and $W^{32}$ represents a group of general formula:

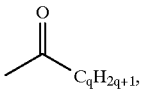

the other group necessarily represents a group of general formula:

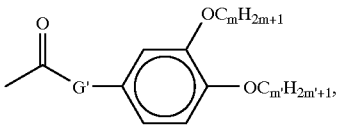

G'—alkenylene group of from 2 to 4 carbon atom(s),

W"—trialkylsilyl group, $W^{12}$—hydrogen atom or alkoxy group of from 1 to 4 carbon atom(s).

Step (aa) is reaction for introducing an acyl group into the amino group, i.e. N-acylation, and it may be carried out by using a corresponding carboxylic acid of general formula:

(XIIIAa)

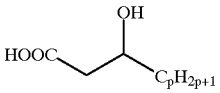

(XIVAa)

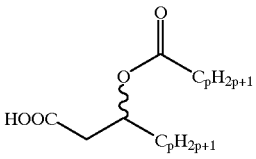

(XIVAb)

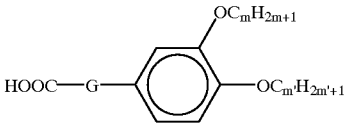

(XIVAc)

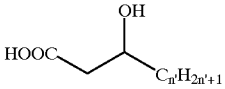

(XIVAd)

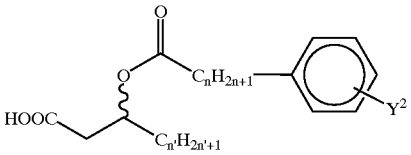

(XIVAe)

(wherein all symbols are the same meaning as defined hereinbefore.) instead of a compound of general formula (XIII) or (XIV) by the same procedure as described in step (a).

Step (bb) is a reaction for introducing an acyl group into the hydroxy group, i.e. O-acylation, and it may be carried out by the same procedure as described in step (b).

Step (cc) is the acylation of the amino group of the 2-position of sugar and the hydroxy group of the 3-position of sugar at the same time, and it may be carried out by the same procedure as described in step (g).

Step (dd) is a reaction for removing a benzyl group, and it may be carried out by the same procedure as described in stop (e).

Step (ee) is a reaction for introducing an acyl group into the amino group, i.e. N-acylation, and may be carried out by using a compound of general formula (IVB) by the same procedure as described in step (a)

Step (ff) is a reaction for introducing an acyl group into the hydroxy group, i.e. O-acylation, and may be carried out by the same procedure as described in step (b).

Step (gg) is the acylation of the amino group of the 2-position of sugar and the hydroxy group of the 3-position of sugar at the same time, and it may be carried out by the same procedure as described in step (g).

Step (hh) is a reaction for removing the isopropylidene group on the 4th and 6th positions of the sugar as hydroxy-protecting group, and it may be carried out by the same procedure as described in the step (c).

Step (ii) is a reaction for introducing a protecting group into the hydroxy group on the 6-position selectively, and it may be carried out by the same procedure as described in step (d).

Step (jj) is a reaction for removing a benzyl group, and it may be carried out by the same procedure as described in step (e).

Step (kk) is a reaction for introducing a sulfo group into the hydroxy group on the 4-position of sugar, and it may be carried out by the same procedure as described in step (f).

Step (ll) is a reaction for introducing a sulfo group into the hydroxy group on the 4-position of sugar, and it may be carried out by the same procedure as described in step (f).

Step (mm) is a reaction for removing a benzyl group in a compound of general formula (VIIB) wherein $W^{11}$ is a benzyloxy group, and it may be carried out by the same procedure as described in step (e).

Step (nn) is a catalytic reduction, and it may be carried out by the same procedure as described in step (e).

Throughout the specification, in each reaction, the products may be purified by conventional methods, for example, distillation at atmospheric or reduced pressure, high performance liquid chromatography, thin layer chromatography using silica gel or magnesium silicate or washing or recrystallization. Purification may be carried after each reaction or after a series of reactions.

STARTING MATERIALS

Starting materials and reagents using in the present invention are known compounds per se or may be prepared by known methods per se.

For example, the compounds of general formula (IV) were described in Agric. Biol. Chem., 48(1), 251 (1984).

The compounds of general formula (IVa) wherein $W^{11}$ is a hydrogen atom, may be synthesized easily from the compounds described in J. Org. Chem., 30(4), 1282 (1985) by known methods.

SALTS

The compounds of the present invention of general formulae (I) and (IA) may be [formed] *in the form of* salts at the sulfo group.

By conversion into salts, solubility of the compounds of the present invention in water can be increased, and therefore this embodiment may be useful for administration as pharmaceuticals.

The compounds of the present invention may easily be converted into corresponding salts by methods known per se, e.g. methods described hereafter.

The salts in the present invention are preferably non-toxic. The non-toxic salts herein referred to mean salts of cations such that the salt is relatively innoxious to the living body (animals including human beings) tissues and that the effective pharmacological properties of the compounds of general formulae (I) and (IA) are not impaired by side effect(s) resulting from the cations when used in an amount required for the prevention and/or treatment of the desired conditions. Water-soluble salts are preferable.

Suitable salts include, for example, a salt of an alkali metal such as sodium, potassium, a salt of an alkaline earth metal such as calcium, magnesium, an ammonium salt and a pharmaceutically acceptable (non-toxic) amine salt.

Amines suitable for forming such salts with a sulfo group are well known and include, for example, those amines which are theoretically obtained by substituting one or more of hydrogen atom(s) of ammonia by other group(s). These groups, which may be the same or different when one or more hydrogen atom(s) are substituted, are selected from, for example, alkyl group(s) of from 1 to 6 carbon atom(s) and hydroxyalkyl group(s) of from 1 to 3 carbon atom(s). Suitable non-toxic amine salts include salts of a tetraalkylammonium group, such as tetramethylammonium salt and salts of an organic amine, such as methylamine, dimethylamine, cyclopentylamine, benzylamine, phenthylamine, piperidine, monoethanolamine, diethanolamine, lysine and arginine.

Salts are obtained from the compounds of the present invention of general formulae (I) and (IA), by methods known per se, for example, by reacting a compound of the general formula (I) or (IA) and a suitable base such as a hydroxide or carbonate of an alkali metal or alkaline earth metal, ammonium hydroxide, ammonia or an organic amine in theoretical amounts in an appropriate solvent.

The salts can be isolated by freeze-drying the solution, or by filtration if salts are sufficiently insoluble to the reaction solution, or if necessary, by removing part of the solvent followed by filtration.

PHARMACOLOGICAL ACTIVITIES

The compounds of the present invention of the general formulae (I) and (IA), possess lipid A-like activities described hereinbefore. As example of such utilities, the following results are illustrative, using standard laboratory techniques:

(1) Mitogenic activity in vitro

The compounds of the present invention showed activities as in the following Table I(1), with the test system described hereafter.

TABLE I(1)

| Example No. of the compounds | Blastgenic Index |
|---|---|
| 1(c) | 30 |
| 1(d) | 28 |
| 1(f) | 23 |
| 1(h) | 37 |
| 1(j) | 25 |
| 1(r) | 17 |
| 1(o) | 17 |
| 1(u) | 10 |
| 1(s) | 58 |
| 1(t) | 50 |
| 2 | 33 |
| 3(b) | 13.7 |
| 3(c) | 13.8 |
| 3(g) | 17.6 |
| 4 | 27.7 |

Mitogenic activity means activity of activating mitogenic cell division, and in this test system, the amount of tymidine taken into lympha cells was measured and a ratio determined against a blank control call (Blastogenic index) was calculated.

For example, adding the compound prepared in example 1(c) to the test system induced 30 times the amount of tymidine taken into the lympha cells versus the control.

The amounts were measured by density of a radiolabel.

Mytogenic activity in vitro was measured by the following method (See Procedure Method of Immunoexperiment pp 315 published by Japan Immunology Society).

C3H/He male mice 6 weeks old were killed by bloodletting, and their spleens were isolated and homogenized. Homogenizing liquids were filtered with gauze, and suspending cells were prepared with PBS solution. After washing, lymphacytes fractions were gathered with lympholight M. Lymphacytes were suspended in RPMI 1640 cultivation solution (10% FEBS), and the solution was divided into $5\times10^5$ cells/180 μl/wells. Ten times concentration of the terminal concentration (1 μg/ml) of the compounds of the present invention were added with 20 μl portions to each of the wells.

In an atmosphere of a mixed gas of 5% $CO_2$–95% $O_2$, the cells were cultivated for 24 hrs at 37° C. After cultivation, $^3$H-tymidine 0.5 μCi/20 μl was added to the each cells. Cultivation was continued at 37° C. for another 24 hrs, and amounts of $^3$H-tymidine taken into the cells were measured. Mitogenic activities were calculated as by Blastogenic index in as follows.

$$\text{Elastogenic index} = \frac{\text{Amount of } ^3\text{H-tymidine taken into the lymphacytes with adding the compound of the present invention}}{\text{Amount of } ^3\text{H-tymidine taken into the blank control lymphacytes}}$$

(2) Inducing activities of TNF in vitro

The compounds of the present invention showed activities as in the following Table I(2), with the test system described hereafter.

TABLE I(2)

| Example No. of the compounds | Cytotoxicities (%) |
|---|---|
| 1(c) | 86 |
| 1(d) | 95 |
| 1(h) | 81 |
| 1(j) | 69 |
| 1(r) | 86 |
| 1(s) | 100 |
| 3 | 50.7 |
| 3(b) | 30.2 |
| 3(g) | 87.9* |
| 4 | 20.0 |

*serum dilution ½s

Inducing activity of TNF in vitro was measured by the following test system.

Corye parvum (manufactured by Ribi Immuno Chem. Research Inc.) was administered in ICR male mice 6-weeks old through the tail vein as priming agent. Ten days later, the compounds of the present invention (10 μg) were administered through tail vein as eliciting agent. 90 mins after the administration, blood was collected from the hearts, and blood serums were separated.

Mice L-M cells ($10^4$/100 μl/well) suspended in a mixture of the diluted serum solution (100 μl/well) and RPMI 1640 cultivating solution (10% FEBS and 0.2% glucose; manufactured by Nissui Pharmaceutical Co.) were cultivated in an atmosphere of a mixed gas of 5% $CO_2$–95% $O_2$, for 48 hrs at 37° C., after adding $^3$H-tymidine taken (0.5 μCi/20 μl/well). Amounts of $^3$H-tymidine taken into cells during the cultivation were measured.

Inducing activities of TNF were measured by cytotoxicity calculated as follows:

$$\text{Cytotoxicity (\%)} = \left(\frac{\text{Amount of } ^3\text{H-tymidine taken into the lymphacytes with adding the compound of the present invention}}{\text{Amount of } ^3\text{H-tymidine into taken the blank control lympacytes}}\right)\times 100$$

TOXICITY

It was confirmed that the acute toxicity ($LD_{50}$) of the compounds of the present invention were more than 100 mg/kg animal body weight by intravenous administration. Therefore, the compounds of the present invention may be considered to be sufficiently safe and suitable for pharmaceutical use.

For example, the values of $LD_{50}$ of the compound prepared in example 1(c) was more than 300 mg/kg animal body weight by intravenous administration in mice.

APPLICATIONS AS PHARMACEUTICALS

In mammals including human beings, especially human beings, decrease of immunity decreased of aging, disorders including immunodeficiencies etc., may induce fatal infections, e.g., opportunistic infection.

The compounds of the present invention of the general formulae (I) and (IA) possess enhancing activity of cellular immunity (e.g. mitogenic activity) to living tissue as examplified by the experimental results discussed above, and therefore are useful as enhancing agents of immunity.

The compounds of the present invention of general formulae (I) and (IA) posses an inducing activity of TNF, an inducing activity of IL-1 and an inducing activity of IFN, and therefore are also useful as anti-tumor agents.

As example of such an anti-tumor effect, the following results are ilustrative, using standard laboratory techniques:

(1) Anti-tumor effect on Balb/C mice inocudlated with Meth-A Sarcoma

Anti-tumor effect was measured by the following procedure.

Tumor cells which had been maintained in ascites of Balb/C mouse generation after generation was used. One group is consisting of eight female Balb/C mice. Meth-A sarcoma tumor ($1\times10^5$ cells/0.05 ml) was inoculated into left side of female mice of 7-week old (body weight: 18–20 g). Seven day after, when tumor size came to 6~9 mm, test compound was administered into tail vein first (day 7) and then administered two times (total three times: Day 7, 9, 12). Dose of test compound is 3 and 10 mg/kg or 3, 10 and 30 mg/kg and each test compound solution volume was 10 ml/kg. Anti-tumor effect is estimated by survival period (from inoculation day to death day) and tumor apparent weight.

$$\text{Tumor apparent weight (mg)} = \text{long diameter of tumor (mm)} \times \text{(short diameter of tumor (mm))}^2 \times 1/2$$

Test results about survival period and tumor appearent weight are shown in the following Tables II(1) and II(2), respectively.

TABLE II(1)

| Example No. of the compounds | Dose (mg/body) | Survival period (day ± standard error) |
|---|---|---|
| 1(C) | Control | 46.1 ± 3.3 |
| | 3 | 46.8 ± 6.3 |
| | 10 | 62.8 ± 18.8* |
| 4 | Control | 34.6 ± 7.8 |
| | 3 | 48.5 ± 8.7*** |
| | 10 | 46.6 ± 7.2*** |
| 4(b) | Control | 42.9 ± 10.6 |
| | 3 | 61.6 ± 18.0* |
| | 10 | 65.8 ± 20.4** |
| 4(C) | Control | 42.9 ± 10.6 |
| | 3 | 51.9 ± 8.2* |
| | 10 | 58.3 ± 13.8*** |
| | 30 | 71.3 ± 16.1**** |

In experiments, statistic analysis was done with unpaired Student's t(two tailed)-test. In tables *, , * and **** showed significant difference from the value of respective control (P<0.05, P<0.02, P<0.01, P<0.001). P values lower than 0.05 were judged to be significant.

TABLE II(2)

| Example No. of the compounds | Dose (mg/kg) iv | Apperarent tumor weight (g ± standard error) Day 7 | Day 10 | Day 13 | Day 16 |
|---|---|---|---|---|---|
| 1(c) | control | 0.198 ± 0.054 | 0.314 ± 0.066 | 0.411 ± 0.120 | 0.734 ± 0.287 |
| | 3 | 0.200 ± 0.074 | 0.240 ± 0.118 | 0.314 ± 0.206 | 0.580 ± 0.412 |
| | 10 | 0.199 ± 0.044 | 0.156 ± 0.084**** | 0.120 ± 0.099**** | 0.208 ± 0.253**** |
| 4 | control | 0.206 ± 0.035 | 0.539 ± 0.110 | 0.906 ± 0.188 | 1.666 ± 0.560 |
| | 3 | 0.212 ± 0.042 | 0.469 ± 0.169 | 0.650 ± 0.162* | 1.004 ± 0.434* |
| | 10 | 0.205 ± 0.022 | 0.361 ± 0.056*** | 0.455 ± 0.116*** | 0.846 ± 0.233**** |
| 4(b) | control | 0.203 ± 0.049 | 0.349 ± 0.165 | 0.739 ± 0.517 | 1.238 ± 0.785 |
| | 3 | 0.218 ± 0.028 | 0.172 ± 0.094*** | 0.272 ± 0.181*** | 0.430 ± 0.459*** |
| | 10 | 0.217 ± 0.022 | 0.154 ± 0.042*** | 0.197 ± 0.068*** | 0.172 ± 0.141*** |
| 4(c) | control | 0.203 ± 0.049 | 0.349 ± 0.165 | 0.739 ± 0.517 | 1.238 ± 0.785 |
| | 3 | 0.200 ± 0.044 | 0.230 ± 0.084* | 0.392 ± 0.176 | 0.578 ± 0.274** |
| | 10 | 0.210 ± 0.025 | 0.206 ± 0.053** | 0.242 ± 0.086*** | 0.300 ± 0.193*** |
| | 30 | 0.209 ± 0.023 | 0.168 ± 0.062*** | 0.222 ± 0.152*** | 0.309 ± 0.259*** |

*P < 0.05
**P < 0.02
***P < 0.01
****P < 0.001

From the above results, compounds of example No. 1(C), 4, 4(b) and 4(c) exhibit a significant effect on prolongation of life and on tumore regression at the dose of 10, 3, 3 and 3 mg/kg, respectively.

(2) Anti-tumor effect on Balb/C mice inoculated with RLδ1 tumor.

Tumor cells which had been maintained in ascites of Balb/C mouse generation after generation was used. One group is consisting of six female balb/C mice. RLδ1 tumor ($1\times10^5$ cells/0.05 ml) was inoculated into left side of female mice of 6-week old (body weight: 18~20 g). Ten days after, when tumore size came to 7~10 mm, compound of example No. 1(1) or 1(t) was administered by i.p. route (Day 10). Dose of test compound was 1 and 3 mg/body dand each test compound solution volume was 10 ml/kg. Antitumore effect is estimated by survival period and tumor appearent weight.

Test results about survival period and tumor apparent weight are shown in the following Tables II(3) and II(4), respectively.

TABLE II(3)

| Example No. of the compounds | Dose (mg/body) ip | Survival period (day ± standard error) |
|---|---|---|
| 1(l) | Control | 45.2 ± 19.6 |
| | 1 | 47.3 ± 18.8 |
| | 3 | 55.3 ± 16.4 |
| 1(t) | Control | 45.2 ± 19.6 |
| | 1 | 51.8 ± 20.1 |
| | 3 | 54.0 ± 18.4 |

TABLE II(4)

| Example No. of the compounds | Dose (mg/kg) ip | Appearent tumor weight (g ± standard error) Day 10 | Day 10 | Day 13 |
|---|---|---|---|---|
| 1 (l) | control | 0.217 ± 0.092 | 0.517 ± 0.270 | 0.683 ± 0.580 |

TABLE II(4)-continued

| Example No. of the compounds | Dose (mg/kg) ip | Appearent tumor weight (g ± standard error) Day 10 | Day 10 | Day 13 |
|---|---|---|---|---|
| | 1 | 0.216 ± 0.043 | 0.234 ± 0.168 | 0.351 ± 0.349 |
| | 3 | 0.216 ± 0.029 | 0.210 ± 0.192* | 0.333 ± 0.375 |
| 1(t) | control | 0.217 ± 0.092 | 0.517 ± 0.270 | 0.683 ± 0.580 |
| | 1 | 0.226 ± 0.082 | 0.241 ± 0.257 | 0.383 ± 0.583 |
| | 3 | 0.213 ± 0.041 | 0.159 ± 0.092** | 0.147 ± 0.153 |

*P < 0.05
**P < 0.02

From the above results, compounds of example No. 1(1) and 1(t) at the dose of 3 mg/body on Day 14 (4 day after administration) exhibit a significant effect on tumor regression.

For the treatment of immuno deficiencies or tumor, the compounds of the present invention of general formulae (I) and (IA) or non-toxic salts thereof may normally be administered systemically or partially; usually by oral or parenteral administration.

The doses to be administered are determined depending upon age, body weight, symptoms, the desired therapeutic effect, the route of administration, and the duration of the treatment etc. In the human adult, the doses per person per dose are generally between 0.1 mg and 100 mg, by oral administration, up to several times per day, and between 10 μg and 10 mg, by parenteral administration to several times per day.

As mentioned above, the doses to be used depend upon various conditions. Therefore, there are cases in which doses lower than or greater than the ranges specified above may be used.

Solid compositions according to the present invention for oral administration include compressed tablets, dispersible powders and granules. In such solid compositions, one or more of the active compound(s) is or are, admixed with at least one inert diluent such as lactose, mannitol, glucose, hydroxypropylcellulose, microcrystalline cellulose, starch, polyvinylpyrrolidone or magnesium metasilicate aluminate. The compositions may also comprise, as is normal practice, additional substances other than inert diluents e.g. lubricating agents such as magnesium stearate, disintegrating agents such as cellulose calcium gluconate, and assistant for dissolving e.g. arginine, glutamic acid or amino-acid such as aspartic acid. The tablets or pills may, if desired, be made into gastric film-coated or enteric film-coated tablets or pills, such as sugar-coated, gelatin-coated, hydroxypropyl cellulose-coated or hydroxypropylmethyl cellulose phthalate-coated tablets or pills and, two or more of layers may be used. The compositions for oral administration also include capsules of absorbable material such as gelatin.

Liquid compositions for oral administration include pharmaceutically-acceptable emulsions, solutions, suspensions, syrups and elixirs containing inert diluents commonly used in the art such as distilled water or ethanol. Besides inert diluents such compositions may also comprise adjuvants such as wetting and suspending agents, and sweetening, flavoring, perfuming and preserving agents.

Other compositions for oral administration include spray compositions which may be prepared by known methods and which comprise one or more of the active compound(s).

Preparations for injection according to the present invention for parenteral administration include sterile aqueous or non-aqueous solutions, suspensions or emulsions. Examples of aqueous solvents or suspending media are distilled water for injection and physiological salt solution. Examples of non-aqueous solvents or suspending media are propylene glycol, polyethylene glycol, vegetable oils such as olive oil, alcohols such as ethanol, POLYSORBATE 80 (registered Trademark). These compositions may also include adjuvants such as preserving, wetting, emulsifying, dispersing agents and assistant agents for dissolving (e.g. arginine, glutamic acid or amino-acid such as aspartic acid). They may be sterilized, for example, by filtration through a bacteria-retaining filter, by incorporation of sterilizing agents in the compositions or by irradiation. They may also be manufactured in the form of sterile solid compositions which can be dissolved in sterile water or some other sterile injectable medium immediately before use.

Other compositions for parenteral administration include liquids for external use, and endermic liniments such as ointments, suppositories and pessaries which comprise one or more of the active compound(s) and may be prepared by known methods.

NOMENCLATURE

Throughout the specification including the claims, the compounds of the present invention and termed derivatives of glucopyranose or 1,5-anhydro-glucitol having the following skeletal structure:

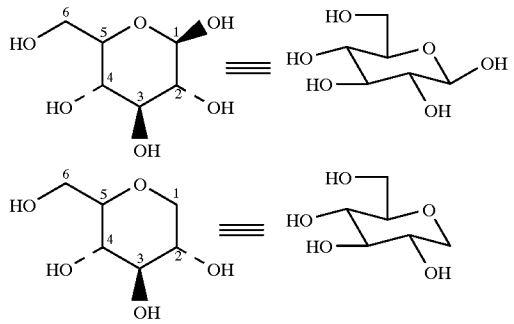

In the structural formula of the specification including the claims, the dotted line (- -), the thickened line (◄) and the wavy line (~) indicate that the respective group attached thereto is in the backside of the plane, i.e. in α-configuration, in the front of the plane, i.e. in β-configuration, and in α- or β-configuration or at mixture thereof, respectively, according to the generally accepted nomenclature rules.

REFERENCE EXAMPLES AND EXAMPLES

The following reference examples and examples illustrate the present invention, but are not to be construed as limiting the present invention.

In the reference examples and examples, "TLC" and "IR" represent "Thin layer chromatography" and "Infrared absorption spectrum", respectively.

The solvents in parentheses refer to the developing or eluting solvents, and the ratios of the solvents used are by volume in chromatographic separations.

Unless otherwise specified, "IR" was measured by the KBr tablet method.

REFERENCE EXAMPLES 1 and 1(a)

Synthesis of benzyl 2-deoxy-2-(3R-hydroxytetradecanoyl)amino-4,6-O-isopropylidine-β-D-glcopyranoside (reference example 1) and benzyl 2-deoxy-2-(3S-hydroxytetradecanoyl)amino-4,6-O-isopropylidene-β-D-glu copyranoside (reference example 1(a))

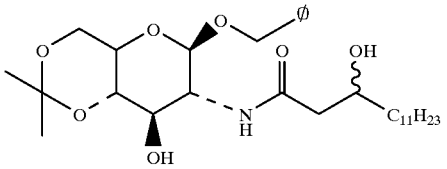

Pivaloyl chloride (1.37 ml) was added to an ice-cooled solution of β-hydroxymiristic acid (2.60 g) in methylene chloride (20 ml), and the mixture was stirred for 30 mins. The solution was added slowly to an ice-cooled solution of benzy 2-deoxy-2-amino-4,6-O-isopropylene-β-D-glucopyranoside (Agric. Biol. Chem., 48(1), 251 (1984); 2.6 g) and triethylamine (1.67 ml) in methylene chloride (20 ml).

The reaction mixture was stirred for 30 mins with ice-cooling and further for 2 hrs at room temperature and then diluted with a mixture of hexane and ethyl acetate ($n\text{-}C_6H_{14}$:EtOAc=1:2; 20 ml). The solution was washed with 1N hydrochloric acid, water and brine, successively dried and evaporated. The residue was purified by column chromatography on silica gel ($EtOAc:CH_2Cl_2$=3:2) to give the title compounds (3R-compound: 1.71 g; 3S-compound: 2.69 g) having the following physical data. 3R-compound:

TLC: Rf 0.31 ($EtOAc:CH_2Cl_2$=3:2);

IR: ν 3500, 3300, 1645, 1630, 1540, 1460, 1450, 1380, 1370, 1260, 1200, 1170, 1080, 1035, 935, 855, 735, 694 $cm^{-1}$ 3S-compound:

TLC: Rf 0.22 ($EtOAc:CH_2Cl_2$=3:2);

IR: same as 3R-compound

REFERENCE EXAMPLES 1(b)~1(f)

By the same procedure as in reference example 1, the following compounds having the physical data shown in Table III were prepared:

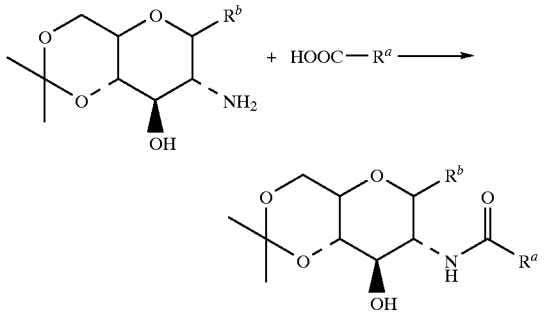

TABLE III

| No. | —$R^b$, —$R^c$ | Name | TLC | IR ($cm^{-1}$) |
|---|---|---|---|---|
| 1 (b) | $R^b$: 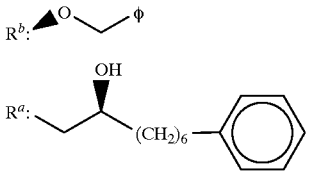 | benzyl 2-deoxy-3-(3R-hydroxy-9-phenylnonanoyl) amino-4,6-O-isopropylidene-β-D-glucopyranoside | Rf 0.45 (EtOAc) | ν (liquid film) 3370, 3330, 2910, 1730, 1630 |
| [1 (c) | $R^b$: 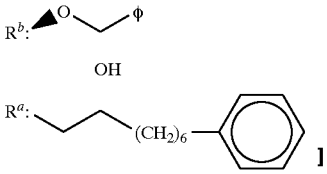 ] | benzyl 2-deoxy-2-(3S-hydroxy-9-phenylnonanoyl) amino-4,6-O-isopropylidene-β-D-glucopyranoside | Rf 0.36 (EtOAc) | ν 3400, 2940, 2860, 1650, 1600 |
| *1 (c)* | $R^b$: 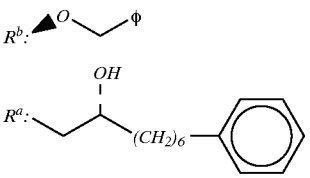 | | | |
| 1 (d) | —$R^b$:—H 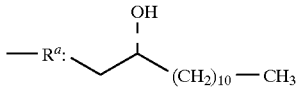 | 2-deoxy-2-(3R-hydroxytetradecanoyloxy)amino-4,6-O-isopropylidene-1,5-anhydro-D-glucitol | Rf 0.24 (EtOAc) | ν 3300, 2925, 2850, 1640, 1550, 1465, 1380 |

TABLE III-continued

| No. | —$R^b$, —$R^c$ | Name | TLC | IR ($cm^{-1}$) |
|---|---|---|---|---|
| 1 (e) | —$R^b$: —H<br>—$R^a$: OH, $(CH_2)_{10}$—$CH_3$ | 2-deoxy-2-(3S-hydroxytetradecanoyloxy)amino-4,6-O-isopropylidene-1,5-anhydro-D-glucitol | Rf 0.21 (EtOAc) | |
| 1 (f) | —$R^b$: $OCH_3$<br>—$R^a$: OH, $(CH_2)_{10}$—$CH_3$ | methyl 2-deoxy-2-(3R-hydroxytetradecanoyloxy) amino-4,6-O-isopropylidene-β-D-glucopyranoside | Rf 0.21 (EtOAc) | ν 3470–3280, 2920, 2850, 1640, 1545, 1465, 1380 |

REFERENCE EXAMPLE 2

Synthesis of benzyl 2-deoxy-2-[3R-(4-phenylbutoxy)tetradecanoyl]amino-3-O-(4-phenylbutyryl)-4,6-O-isopropylidene-β-D-glucopyranoside

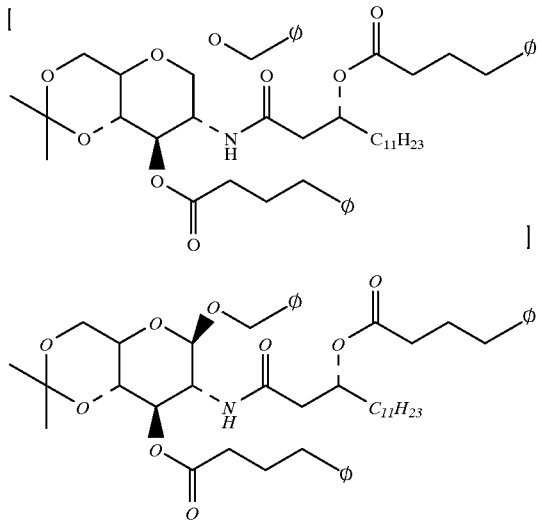

Phenylbutanoic acid (361 mg) and then 2-chloro-1-methylpyridinium iodide (767 mg) and triethylamine (0.84 ml) were added to a solution of the compound (535 mg) prepared in reference example 1 dissolved into methylene chloride (10 ml). The mixture was stirred for 30 mins with ice-cooling. 4-(N,N-dimethylamino) pyridine (61 mg) was added to the reaction solution at room temperature and the mixture was stirred for 18 hrs.

The reaction solution was washed with water, dil. hydrochloric acid and an aqueous saturated solution of sodium bicarbonate, dried and evaporated. The residue was purified by column chromatography on silica gel ($EtOAc:CH_2Cl_2$=1:9) to give the title compound having the following physical data.

TLC: Rf 0.55 ($EtOAc:CH_2Cl_2$=1:9);

IR: ν 3320, 2900, 2480, 1720, 1645, 1515, 1445, 1370, 1190, 1165, 1080, 1020, 850, 725, 690 $cm^{-1}$.

REFERENCE EXAMPLES 2(a)~2(z)

By the same procedure as in reference example 2, using the starting materials specified, the following compounds having the physical data shown in Table IV were prepared:

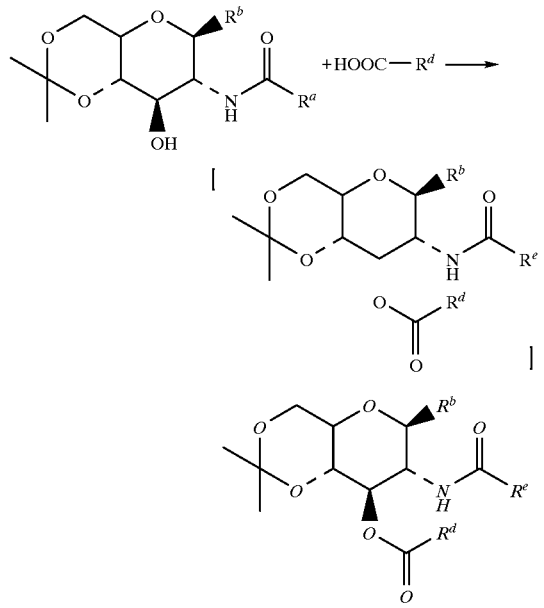

TABLE IV

| No. | $R^b$, $R^c$, $R^d$ | Name | Starting Material | TLC | IR ($cm^{-1}$) |
|---|---|---|---|---|---|
| 2 (a) | 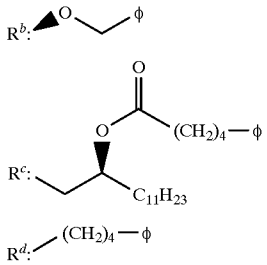 | benzyl 2-deoxy-2-[3S-(5-phenylpentanoyloxy) tetradecanoyl]amino-3-O-(5-phenylpentanoyl)-4,6-O-isopropylidene-β-D-glucopyranoside | Reference Example 1 (a) | Rf 0.78 ($CH_2Cl_2$:EtOAc = 9:1) | |
| 2 (b) | 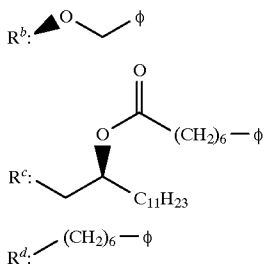 | benzyl 2-deoxy-2-[3S-(7-phenylheptanoyloxy) tetradecanoyl]amino-3-O-(7-phenylheptanoyl)-4,6-O-isopropylidene-β-D-glucopyranoside | Reference Example 1 (a) | Rf 0.79 ($CH_2Cl_2$:EtOAc = 9:1) | |
| 2 (c) | 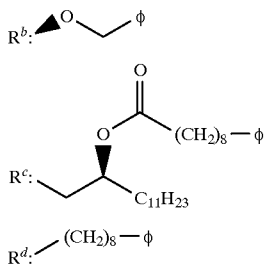 | benzyl 2-deoxy-2-[3S-(9-phenylnonanoyloxy) tetradecanoyl]amino-3-O-(9-phenylnonanoyl)-4,6-O-isopropylidene-β-D-glucopyranoside | Reference Example 1 (a) | Rf 0.78 ($CH_2Cl_2$:EtOAc = 9:1) | |

TABLE IV-continued

| No. | $R^b$, $R^c$, $R^d$ | Name | Starting Material | TLC | IR ($cm^{-1}$) |
|---|---|---|---|---|---|
| 2 (d) | 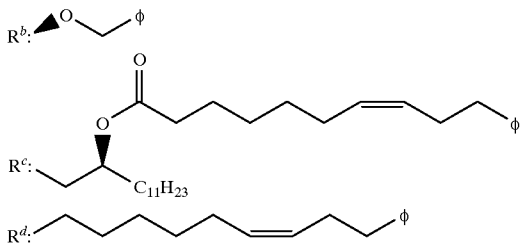 | benzyl 2-deoxy-2-[3S-(10-phenyl-7Z-decenoyloxy) tetradecanoyl]amino-3-O-(10-phenyl-7Z-decenoyl)-4,6-O-isopropylidene-β-D-glucopyranoside | Reference Example 1 (a) | Rf 0.60 ($CH_2Cl_2$:EtOAc = 95:5) | |
| 2 (e) | 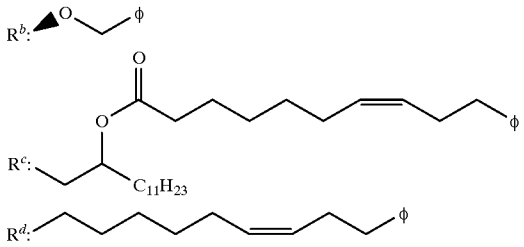 | benzyl 2-deoxy-2-[3R-(10-phenyl-7Z-decenoyloxy) tetradecanoyl]amino-3-O-(10-phenyl-7Z-decenoyl)-4,6-O-isopropylidene-β-D-glucopyranoside | Reference Example 1 | | ν 3460, 2980, 2860, 1730, 1680, 1600, 1510, 1500, 1450, 1380, 1310, 1270, 1180, 1090, 860, 700 |
| 2 (f) | 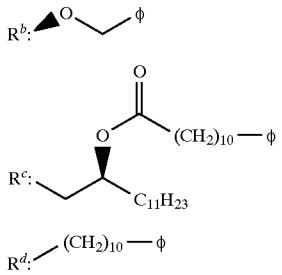 | benzyl 2-deoxy-2-[3S-(10-phenylundecanoyloxy) tetradecanoyl]amino-3-O-(10-phenylundecanoyl-4,6-isopropylidene-β-D-glucopyranoside | Reference Example 1 (a) | | |

TABLE IV-continued

| No. | $R^b$, $R^c$, $R^d$ | Name | Starting Material | TLC | IR ($cm^{-1}$) |
|---|---|---|---|---|---|
| 2 (g) | 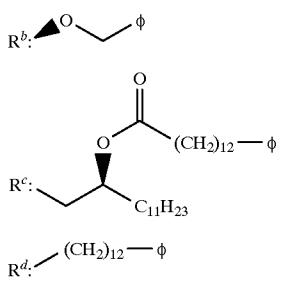 | benzyl 2-deoxy-2-[3S-(13-phenyltridecanoyloxy) tetradecanoyl]amino-3-O-(13-phenyltridecanoyl)-4,6-O-isopropylidene-β-D-glucopyranoside | Reference Example 1 (a) | Rf 0.86 ($CH_2Cl_2$:$CH_3OH$ = 95:5) | |
| 2 (h) | 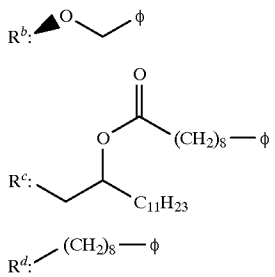 | benzyl 2-deoxy-2-[3R-(9-phenylnonanoyloxy) tetradecanoyl]amino-3-O-(9-phenylnonanoyl)-4,6-amino-3-O-(9-phenylnonanoyl)-4,6-D-glucopyranoside | Reference Example 1 | Rf 0.69 (EtOAc: n-$C_6H_{14}$ = 3:5) | ν 3350, 2910, 1850, 1730, 1680, 1520 |
| 2 (i) | 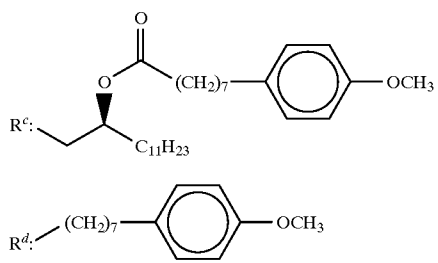 | benzyl 2-deoxy-2-[3S-[8-(4-methoxyphenyl) octanoyloxy]tetradecanoyl]amino-3-O-[8-(4-methoxyphenyl)octanoyl]4,6-O-isopropylidene-β-D-glucopyranoside | Reference Example 1 (a) | Rf 0.78 (EtOAc: n-$C_6H_{14}$ = 1:1) | ν 3410, 3350, 1730, 1710, 1650, 1600 |

TABLE IV-continued

| No. | $R^b$, $R^c$, $R^d$ | Name | Starting Material | TLC | IR ($cm^{-1}$) |
|---|---|---|---|---|---|
| 2 (j) | 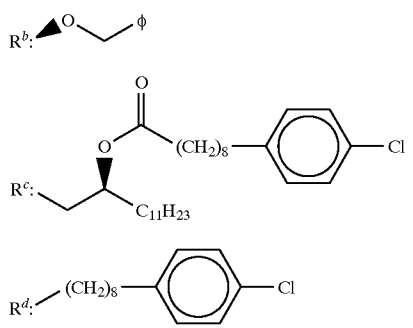 | benzyl 2-deoxy-2-[3S-[9-(4-chlorophenyl) nonanoyloxy]tetradecanoyl]amino-3-O-[9-(4-chlorophenyl)nonanoyl]-4,6-O-isopropylidene-β-D-glucopyranoside | Reference Example 1 (a) | | ν 3350, 2900, 2840, 1720, 1660, 1520, 1490 |
| 2 (k) | 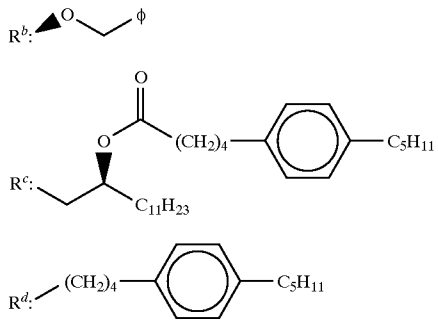 | benzyl 2-deoxy-2-[3S-[5-(4-pentylphenyl) pentanoyloxy]tetradecanoyl]amino-3-O-[5-(4-pentylphenyl)pentanoyl]-4,6-O-isopropylidene-β-D-glucopyranoside | Reference Example 1 (a) | Rf 0.82 (EtOAc: n-$C_6H_{14}$ = 3:5) | ν 3350, 2910, 2850, 1730, 1650, 1520 |
| 2 (l) | 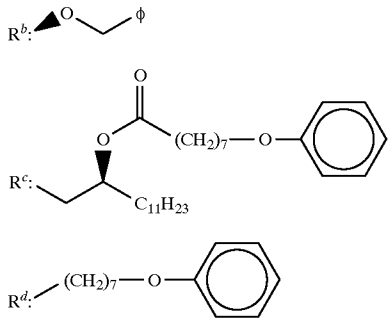 | benzyl 2-deoxy-2-[3S-(8-phenoxyoctanloxy) tetradecanoyl]amino-3-O-(8-phenoxyoctanoyl)-4,6-O-isopropylidene-β-D-glucopyranoside | Reference Example 1 (a) | Rf 0.69 (EtOAc | ν (liquid film) 3300, 2920, 2850, 1730, 1660, 1600 |

TABLE IV-continued

| No. | $R^b$, $R^c$, $R^d$ | Name | Starting Material | TLC | IR ($cm^{-1}$) |
|---|---|---|---|---|---|
| 2 (m) | 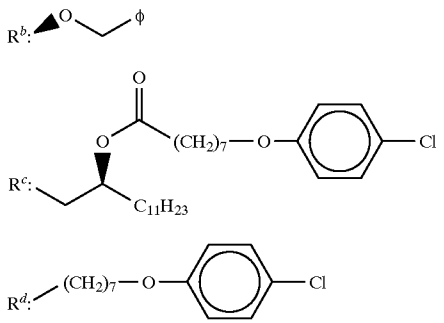 | benzyl 2-deoxy-2-[3S-[8-(4-chlorophenoxy) octanoyloxy]tetradecanoyl]amino-3-O-[8-(4-chlorophenoxy)octanoyl]-4,6-O-isopropylidene-β-D-glucopyranoside | Reference Example 1 (a) | | ν (liquid film) 3320, 2920, 2850, 1730, 1660, 1590 |
| 2 (n) | 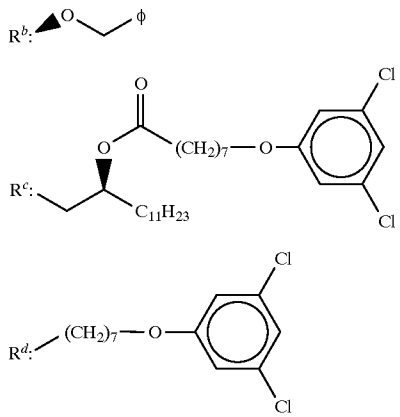 | benzyl 2-deoxy-2-[3S-[8-(3,5-dichlorophenoxy) octadecanoyloxy]tetradecanoyl]amino-3-O-[8-(3,5-dichlorophenoxy)octanoyl]-4,6-O-isopropylidene-β-D-glucopyranoside | Reference Example 1 (a) | Rf 0.65 (EtOAc: n-$C_6H_{14}$ = 3:5) | ν (liquid film) 3270, 2920, 2850, 1730, 1650, 1580, 1560 |

TABLE IV-continued

| No. | $R^b$, $R^c$, $R^d$ | Name | Starting Material | TLC | IR ($cm^{-1}$) |
|---|---|---|---|---|---|
| 2 (o) | 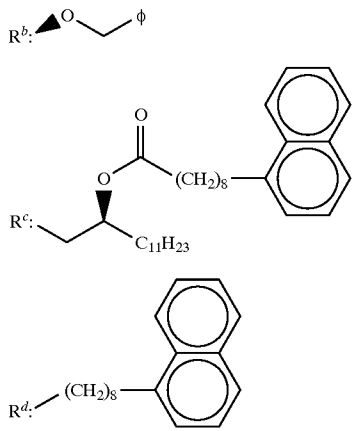 | benzyl 2-deoxy-2-[3S-[9-(1-naphthyl)nonanoyloxy] tetradecanoyl]amino-3-O-]9-(1-naphthyl) nonanoyl]-4,6-O-isopropylidene-β-D-glucopyranoside | Reference Example 1 (a) | Rf 0.79 (EtOAc: n-$C_6H_{14}$ = 3:5) | ν (liquid film) 3280, 2910, 2850, 1730, 1650 |
| 2 (p) | 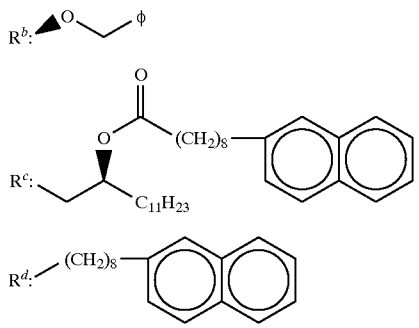 | benzyl 2-deoxy-2-[3S-[9-(2-naphthyl)nonanoyloxy] tetradecanoyl]amino-3-O-[9-(2-naphthyl) nonanoyl]-4,6-O-isopropylidene-β-D-glucopyranoside | Reference Example 1 (a) | | |

TABLE IV-continued

| No. | $R^b$, $R^c$, $R^d$ | Name | Starting Material | TLC | IR ($cm^{-1}$) |
|---|---|---|---|---|---|
| 2 (q) | 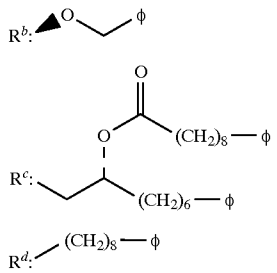 | benzyl 2-deoxy-2-[3R-(9-phenylnonanoyloxy)-9-phenylnonanoyl]amino-3-O-(9-phenylnonanoyl)-4,6-O-isopropylidene-β-D-glucopyranoside | Reference Example 1 (b) | Rf 0.78 (EtOAc: n-$C_6H_{14}$ = 1:1) | ν 3450, 3320, 2920, 2840, 1730, 1650, 1600 |
| 2 (r) | 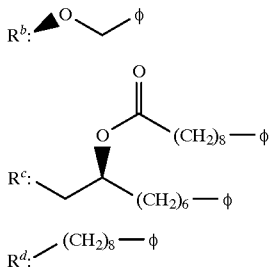 | benzyl 2-deoxy-2-[3S-(9-phenylnonanoyloxy)-9-phenylnonanoyl]amino-3-O-(9-phenylnonanoyl)-4,6-O-isopropylidene-β-D-glucopyranoside | Reference Example 1 (c) | Rf 0.74 (EtOAc: n-$C_6H_{14}$ = 1:1) | ν 3350, 2920, 2850, 1730, 1720, 1650, 1600 |
| 2 (s) | $R^b$: H 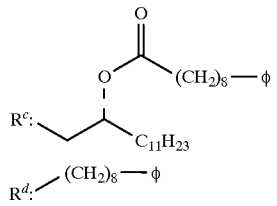 | 2-deoxy-2-[3R-(9-phenylnonanoyloxy) tetradecanoyl]amino-3-O-(9-phenylnonanoyl)-4,6-O-isopropylidene-1,5-anhydro-D-glucitol | Reference Example 1 (d) | Rf 0.25 (EtOAc: n-$C_6H_{14}$ = 1:2) | ν 3400, 2920, 2850, 1740, 1660, 1600, 1510, 1460, 1370 |

TABLE IV-continued

| No. | $R^b$, $R^c$, $R^d$ | Name | Starting Material | TLC | IR ($cm^{-1}$) |
|---|---|---|---|---|---|
| 2 (t) | $R^b$: H<br>$R^c$: 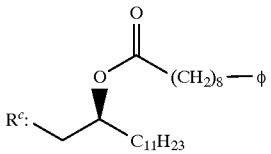 <br>$R^d$: $(CH_2)_8$—ϕ | 2-deoxy-2-[3S-(9-phenylnonanoyloxy) tetradecanoyl]amino-3-O-(9-phenylnonanoyl)-4,6-O-isopropylidene-1,5-anhydro-D-glucitol | Reference Example 1 (e) | Rf 0.25 (EtOAc: n-$C_6H_{14}$ = 1:2) | ν 3400, 2920, 2850, 1740, 1660, 1600, 1510, 1460, 1370 |
| 2 (u) | $R^b$: $OCH_3$<br>$R^c$: 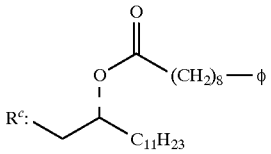 <br>$R^d$: $(CH_2)_8$—ϕ | methyl 2-deoxy-2-[3R-(9-phenylnonanoyloxy) tetradecanoyl]amino-3-O-(9-phenylnonanoyl)-4,6-isopropylidene-β-D-glucopyranoside | Reference Example 1 (f) | Rf 0.52 (EtOAc: n-$C_6H_{14}$ = 1:1) | |
| 2 (v) | $R^b$: H<br>$R^c$: 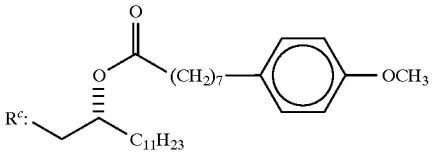 <br>$R^d$: $(CH_2)_7$—ϕ—$OCH_3$ | 2-deoxy-2-[3R-[8-(4-methoxyphenyl)oxtanoyloxy] tetradecanoyl]amino-3-O-[8-(4-methoxyphenyl) octanoyl]-4,6-O-isopropylidene-1,5-anhydro-D-glucitol | Reference Example 1 (d) | Rf 0.78 (EtOAc: n-$C_6H_{14}$ = 1:1) | ν 1730, 1710, 1650, 1600 |

TABLE IV-continued

| No. | $R^b$, $R^c$, $R^d$ | Name | Starting Material | TLC | IR ($cm^{-1}$) |
|---|---|---|---|---|---|
| 2 (w) | $R^b$:—H<br>$R^c$: 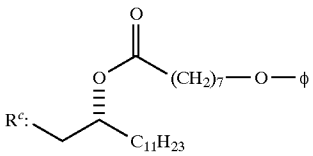 <br>$R^d$:—$(CH_2)_7$—O—ϕ | 2-deoxy-2-[3R-(8-phenoxyoctanoyloxy) tetradecanoyl]amino-3-O-(8-phenoxyoctanoyl)-4,6-O-isopropylidene-1,5-anhydro-D-glucitol | Reference Example 1 (d) | Rf 0.80 (EtOAc: n-$C_6H_{14}$ = 1:1) | ν 1730, 1660, 1600, 1540 |
| 2 (a) | $R^b$:—H | | | | |
| 2 (x) | $R^b$:—H<br>$R^c$: 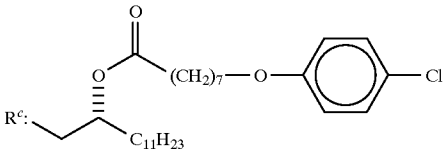 <br>$R^d$: 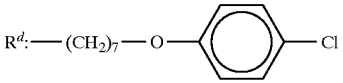 | 2-deoxy-2-[3R-[8-(4-chlorophenoxy)octanoyloxy] tetradecanoyl]amino-3-O-[8-(4-chlorophenoxy) octanoyl]-4,6-O-isopropylidene-1,5-anhydro-D-glucitol | Reference Example 1 (d) | Rf 0.81 (n-$C_6H_{14}$: EtOAc = 1:1) | ν 1730, 1660, 1590 |

TABLE IV-continued

| No. | $R^b$, $R^c$, $R^d$ | Name | Starting Material | TLC | IR ($cm^{-1}$) |
|---|---|---|---|---|---|
| 2 (y) | $R^b$: — H<br>$R^c$: 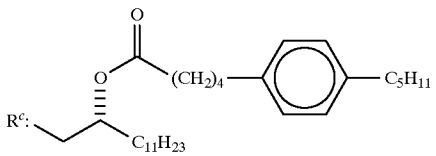 <br>$R^d$: — $(CH_2)_4$ — 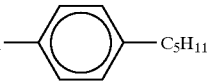 — $C_5H_{11}$ | 2-deoxy-2-[3R-[5-(4-pentylphenyl)pentanoyloxy] tetradecanoyl]amino-3-O-[5-(4-pentylphinyl) pentanoyl]-4,6-O-isopropylidene-1,5-anhydro-D-glucitol | Reference Example 1 (d) | Rf 0.81 (n-$C_6H_{14}$: EtOAc = 3:5) | ν ($CHCl_3$ solution) 1730, 1650, 1520 |
| 2 (z) | $R^b$: — H<br>$R^c$: 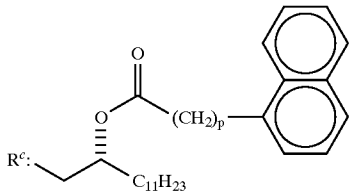 <br>$R^d$: — $(CH_2)_8$ — 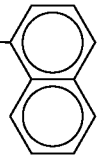 | 2-deoxy-2-[3R-[9-(1-naphthyl)octanoyloxy] tetradecanoyl]amino-3-O-[9-(1-naphthyl) nonanoyl]-4,6-O-isopropylidene-1,5-anhydro-D-glucitol | Reference Example 1 (d) | Rf 0.24 (n-$C_6H_{14}$: EtOAc = 2:1) | ($CHCl_3$ solution) ν 3270, 1730, 1652, 1543, 860, 780 |

REFERENCE EXAMPLE 3

Synthesis of benzyl 2-deoxy-2-[3R-(4-phenylbutyryloxy) tetradecanoyl]amino-3-O-(4-phenylbutyryl)-β-D-glucopyranoside

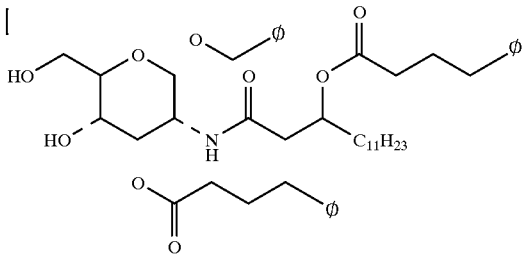

-continued

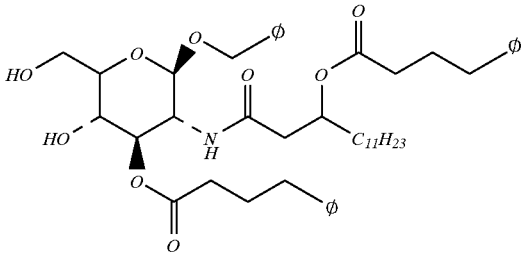

Water (3 ml) and acetic acid (9 ml) were added to a solution of the compound (764 mg) prepared in reference example 2 dissolved into THF (9 ml). The mixture was refluxed for 5.5 hrs. The solution was concentrated and toluene was added to the residue. The solution was concentrated to give the title compound having the following physical data.

TLC: Rf 0.2 ($CH_2Cl_2$:$CH_3OH$=98:2);

TABLE V

| No. | $R^b$, $R^c$, $R^d$ | Name | Starting Material | TLC | IR ($cm^{-1}$) |
|---|---|---|---|---|---|
| 3 (a) | 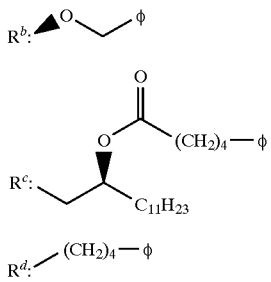 | benzyl 2-deoxy-2-[3S-(5-phenylpentanoyloxy) tetradecanoyl]amino-3-O-(5-phenylpenta-noyl)-β-D-glucopyranoside | Reference Example 2 (a) | | |
| 3 (b) | 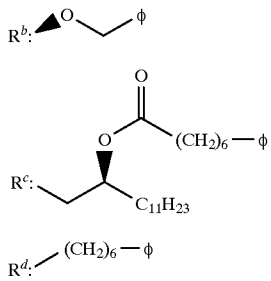 | benzyl 2-deoxy-2-[3S-(7-phenylheptanoyloxy) tetradecanoyl]amino-3-O-(7-phenylhepta-noyl)-β-D-glucopyranoside | Reference Example 2 (b) | | |
| 3 (c) | 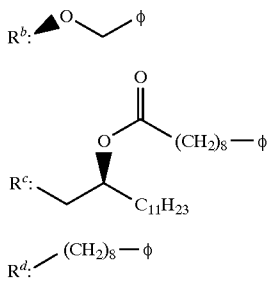 | benzyl 2-deoxy-2-[3S-(9-phenylnonanoyloxy) tetradecanoyl]amino-3-O-(9-phenylnonanoyl)-β-D-glucopyranoside | Reference Example 2 (c) | | |

TABLE V-continued

| No. | $R^b$, $R^c$, $R^d$ | Name | Starting Material | TLC | IR ($cm^{-1}$) |
|---|---|---|---|---|---|
| 3 (d) | 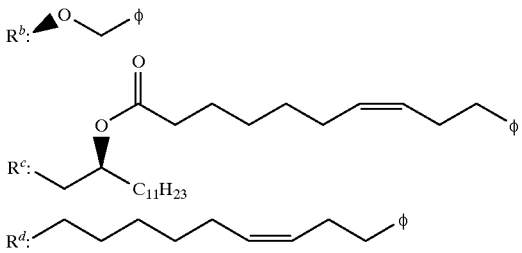 | benzyl 2-deoxy-2-[3S-(10-phenyl-7Z-decanoyloxy)tetradecanoyl]amino-3-O-(10-phenyl-7Z-decanoyl)-β-D-glucopyranoside | Reference Example 2 (d) | | |
| 3 (e) | 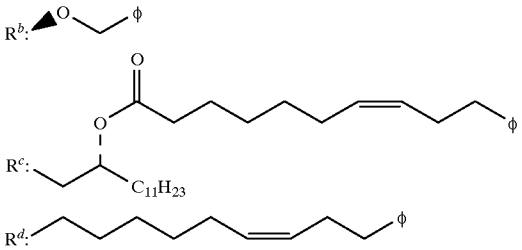 | benzyl 2-deoxy-2-[3R-(10-phenyl-7Z-decanoyloxy)tetradecanoyl]amino-3-O-(10-phenyl-7Z-decanoyl)-β-D-glucopyranoside | Reference Example 2 (e) | | |
| 3 (f) | 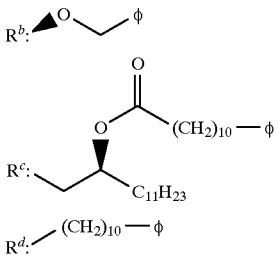 | benzyl 2-deoxy-2-[3S-(11-phenylundecanoyloxy)tetradecanoyl]amino-3-O-(11-phenylundecanoyl)-β-D-glucopyranoside | Reference Example 2 (f) | | |

TABLE V-continued

| No. | $R^b$, $R^c$, $R^d$ | Name | Starting Material | TLC | IR ($cm^{-1}$) |
|---|---|---|---|---|---|
| 3 (g) | 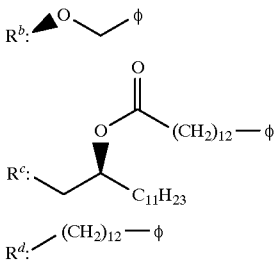 | benzyl 2-deoxy-2-[3S-(13-phenyltrideca-noyloxy)tetradecanoyl]amino-3-O-(13-phenyltridecanoyl)-β-D-glucopyranoside | Reference Example 2 (g) | | |
| 3 (h) | 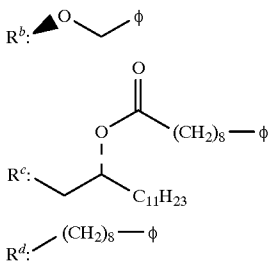 | benzyl 2-deoxy-2-[3R-(9-phenylnonanoyl-oxy)tetradecanoyl]amino-3-O-(9-phenylnonanoyl)-β-D-glucopyranoside | Reference Example 2 (h) | Rf 0.18 (EtOAc: n-$C_6H_{14}$ = 3:5) | ν 3450, 3270, 2920, 2850, 1730, 1650, 1550 |
| 3 (i) | 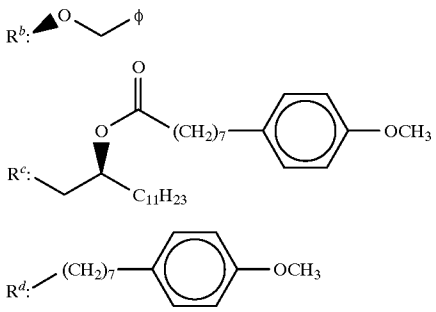 | benzyl 2-deoxy-2-[3S-[8-(4-methoxyphenyl) octanoyloxy]tetradecanoyl]amino-3-O-[8-(4-methoxyphenyl)octanoyl]-β-D-glucopyranoside | Reference Example 2 (i) | Rf 0.07 (EtOAc: n-$C_6H_{14}$ = 1:1) | |

TABLE V-continued

| No. | $R^b$, $R^c$, $R^d$ | Name | Starting Material | TLC | IR ($cm^{-1}$) |
|---|---|---|---|---|---|
| 3 (j) | 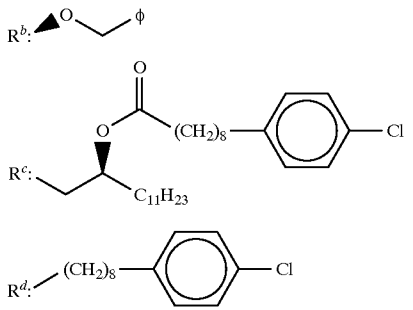 | benzyl 2-deoxy-2-[3S-[9-(4-chlorophenyl) nonanoyloxy]tetradecanoyl]amino-3-O-[9-(4-chlorophenyl)nonanoyl]-β-D-glucopyranoside | Reference Example 2 (j) | Rf 0.06 (EtOAc: n-$C_6H_{14}$ = 3:5) | |
| 3 (k) | 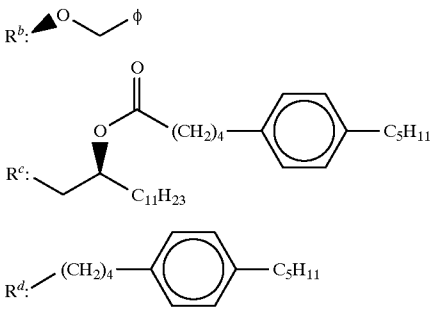 | benzyl 2-deoxy-2-[3S-[5-(4-pentylphenyl) pentanoyloxy]tetradecanoyl]amino-3-O-[5-(4-pentylphenyl)pentanoyl]-β-D-glucopyranoside | Reference Example 2 (k) | Rf 0.04 (EtOAc: n-$C_6H_{14}$ = 3:5) | |
| 3 (l) | 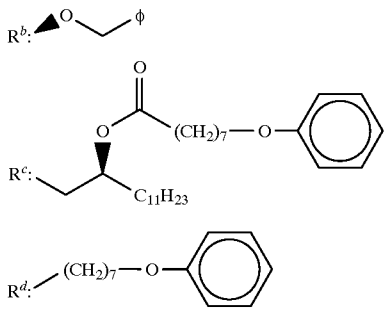 | benzyl 2-deoxy-2-[3S-(8-phenoxyocta-noyloxy)tetradecanoyl]amino-3-O-(8-phenoxyoctanoyl)-β-D-glucopyranoside | Reference Example 2 (l) | Rf 0.06 (EtOAc: n-$C_6H_{14}$ = 3:5) | |

TABLE V-continued

| No. | $R^b$, $R^c$, $R^d$ | Name | Starting Material | TLC | IR ($cm^{-1}$) |
|---|---|---|---|---|---|
| 3 (m) | 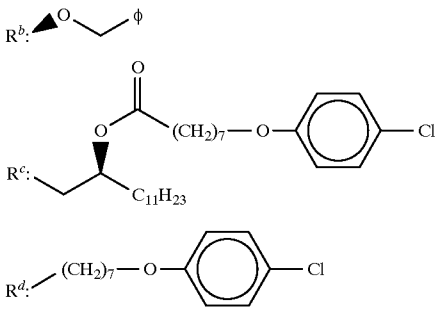 | benzyl 2-deoxy-2-[3S-[8-(4-chlorophenoxy) octanoyloxy]tetradecanoyl]amino-3-O-(8-(4-chlorophenoxy)octanoyl]-β-D-glucopyranoside | Reference Example 2 (m) | Rf 0.03 (EtOAc: n-$C_6H_{14}$ = 3:5) | |
| 3 (n) | 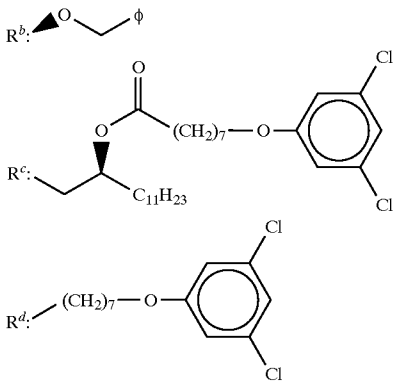 | benzyl 2-deoxy-2-[3S-[8-(3,5-dichloro-phenoxy) octanoyloxy]tetradecanoyl]amino-3-O-[8-(3,5-dichlorophenoxy)octanoyl] β-D-glucopyranoside | Reference Example 2 (n) | Rf 0.05 (EtOAc: n-$C_6H_{14}$ = 3:5) | |

TABLE V-continued
| No. | $R^b$, $R^c$, $R^d$ | Name | Starting Material | TLC | IR ($cm^{-1}$) |
|---|---|---|---|---|---|
| 3 (o) | 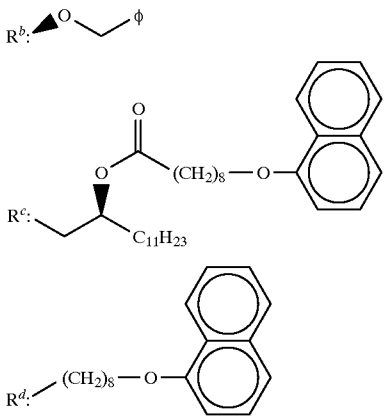 | benzyl 2-deoxy-2-[3S-[9-(1-naphthyl)-nonanoyloxy]tetradecanoyl]amino-3-O-[9-(1-naphthyl)nonanoyl]-β-D-glucopyranoside | Reference Example 2 (o) | Rf 0.03 (EtOAc: n-$C_6H_{14}$ = 3:5) | |
| 3 (p) | 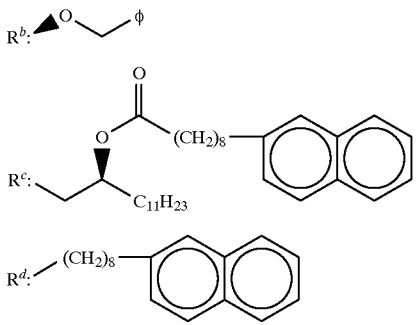 | benzyl 2-deoxy-2-[3S-[9-(2-naphthyl)-nonanoyloxy]tetradecanoyl]amino-3-O-[9-(2-naphthyl)nonanoyl]-β-D-glucopyranoside | Reference Example 2 (p) | Rf 0.06 (EtOAc: n-$C_6H_{14}$ = 3:5) | |

TABLE V-continued

| No. | $R^b$, $R^c$, $R^d$ | Name | Starting Material | TLC | IR ($cm^{-1}$) |
|---|---|---|---|---|---|
| 3 (q) | 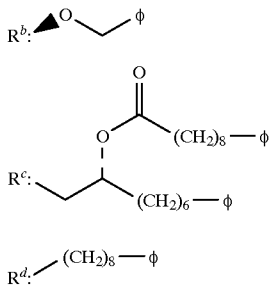 | benzyl 2-deoxy-2-[3R-(9-phenylnonanoyl-oxy)-9-phenylnonanoyl]amino-3-O-(9-phenyl-nonanoyl)-β-D-glucopyranoside | Reference Example 2 (q) | Rf 0.13 (EtOAc: n-$C_6H_{14}$ = 1:2) | |
| 3 (r) | 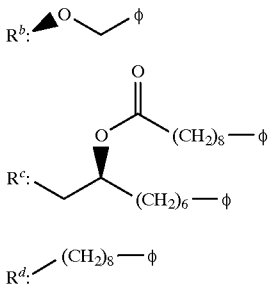 | benzyl 2-deoxy-2-[3S-(9-phenylnonanoyl-oxy)-9-phenylnonanoyl]amino-3-O-(9-phenyl-nonanoyl)-β-D-glucopyranoside | Reference Example 2 (r) | Rf 0.15 (EtOAc: n-$C_6H_{14}$ = 1:2) | |
| 3 (s) | $R^b$: H 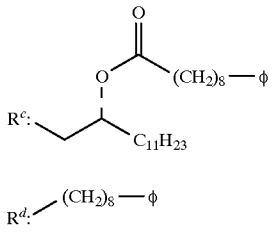 | 2-deoxy-2-[3R-(9-phenylnonanoyloxy) tetradecanoyl]amino-3-O-(9-phenylnonanoyl)-1,5-anhydro-D-glucitol | Reference Example 2 (s) | Rf 0.38 ($CH_2Cl_2$: $CH_3OH$ = 9:1) | |

TABLE V-continued

| No. | $R^b$, $R^c$, $R^d$ | Name | Starting Material | TLC | IR ($cm^{-1}$) |
|---|---|---|---|---|---|
| 3 (t) | $R^b$: H<br>$R^c$: 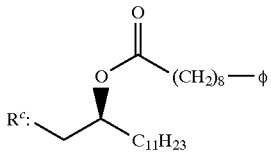 <br>$R^d$: $(CH_2)_8$—ϕ | 2-deoxy-2-[3S-(9-phenylnonanoyloxy) tetradecanoyl]amino-3-O-(9-phenylnonanoyl)-1,5-anhydro-D-glucitol | Reference Example 2 (t) | Rf 0.38 ($CH_2Cl_2$: $CH_3OH$ = 9:1) | |
| 3 (u) | $R^b$: $OCH_3$<br>$R^c$: 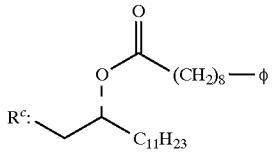 <br>$R^d$: $(CH_2)_8$—ϕ | methyl 2-deoxy-2-[3R-(9-phenylnonanoyloxy) tetradecanoyl]amino-3-O-(9-phenyl-nonanoyl)-β-D-glucopyranoside | Reference Example 2 (u) | Rf 0.55 ($CH_2Cl_2$: $CH_3OH$ = 9:1) | |
| 3 (v) | $R^b$: H<br>$R^c$: 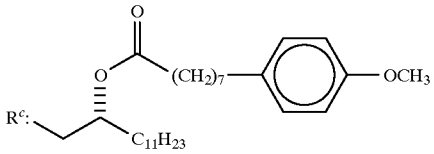 <br>$R^d$: $(CH_2)_7$—ϕ—$OCH_3$ | 2-deoxy-2-[3R-[8-(4-methoxyphenyl)octa-noyloxy]tetradecanoyl]amino-3-O-[8-(4-methoxyphenyl)octanoyl]-1,5-anhydro-D-glucitol | Reference Example 2 (v) | Rf 0.06 (EtOAc: n-$C_6H_{14}$ = 1:1) | |

TABLE V-continued

| No. | $R^b$, $R^c$, $R^d$ | Name | Starting Material | TLC | IR ($cm^{-1}$) |
|---|---|---|---|---|---|
| 3 (w) | $R^b$: — H<br>$R^c$: 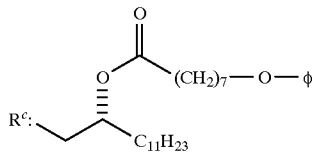 <br>$R^d$: — $(CH_2)_7$ — O — ϕ | 2-dexoy-2-[3R-(8-phenoxyoctanoyloxy) tetradecanoyl]amino-3-O-(8-phenoxy-octanoyl)-1,5-anhydro-D-glucitol | Reference Example 2 (w) | Rf 0.07 (EtOAc: n-$C_6H_{14}$ = 1:1) | |
| 3 (x) | $R^b$: — H<br>$R^c$: 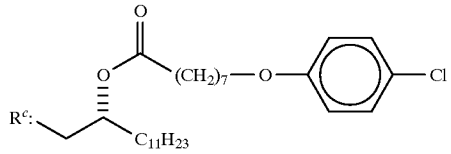 <br>$R^d$: — $(CH_2)_7$ — O — 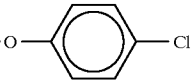 Cl | 2-deoxy-2-[3R-[8-(4-chlorophenoxy)octa-noyloxy]tetradecanoyl]amino-3-O-[8-(4-chlorophenoxy)octanoyl]-1,5-anhydro-D-glucitol | Reference Example 2 (x) | | |

TABLE V-continued

| No. | $R^b$, $R^c$, $R^d$ | Name | Starting Material | TLC | IR ($cm^{-1}$) |
|---|---|---|---|---|---|
| 3 (y) | $R^b$: — H<br>$R^c$: 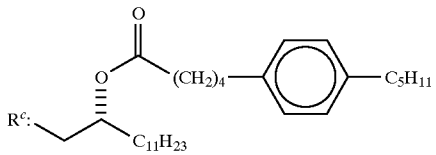 <br>$R^d$: — $(CH_2)_4$ — 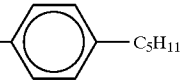 — $C_5H_{11}$ | 2-deoxy-2-[3R-[5-(4-pentylphenyl)penta-noyloxy]tetradecanoyl]amino-3-O-[5-(4-pentylphenyl)pentanoyl]-1,5-anhydro-D-glucitol | Reference Example 2 (y) | | |
| 3 (z) | $R^b$: — H<br>$R^c$: 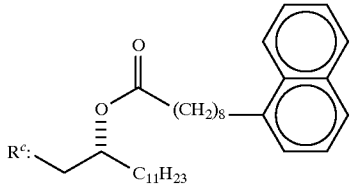 <br>$R^d$: — $(CH_2)_8$ — 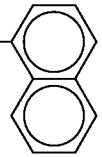 | 2-deoxy-2-[3R-[9-(1-naphthyl)nonanoyloxy]tetradecanoyl]amino-3-O-[9-(1-naphthyl)-nonanoyl]-1,5-anhydro-D-glucitol | Reference Example 2 (z) | Rf 0.55 ($n$-$C_6H_{14}$: EtOAc = 3:1) | |

IR: ν 3300, 2940, 2860, 1725, 1660, 1540, 1450, 1370, 1250, 1170, 1080, 1040, 730, 690 $cm^{-1}$.

REFERENCE EXAMPLES 3(a)~3(z)

By the same procedure as in reference example 3, using the starting materials specified, the following compounds having the physical data shown in Table V were prepared.

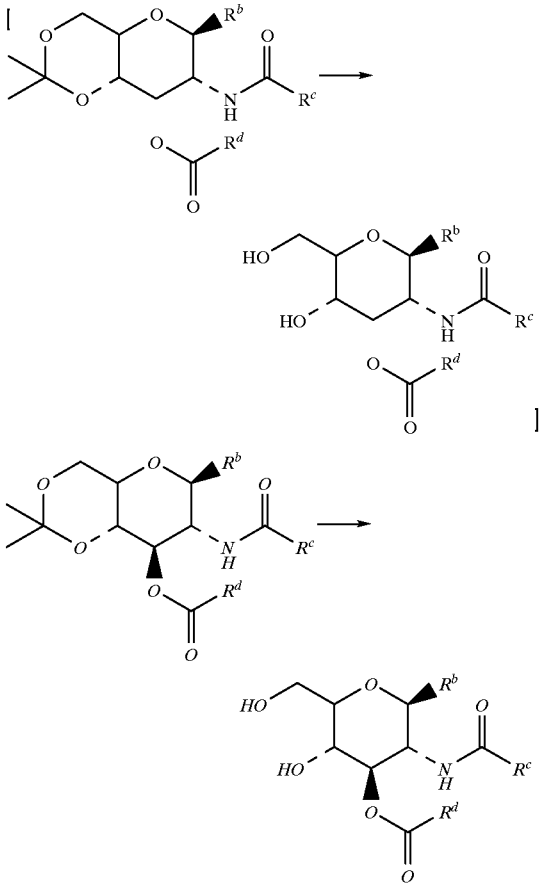

REFERENCE EXAMPLE 4

Synthesis of benzyl 2-deoxy-2-[3R-(4-phenylbutyryloxy)tetradecanoyl]amino-3-O-(4-phenylbutyryl)-6-O-t-butyldimethylsilylglucopyranoside

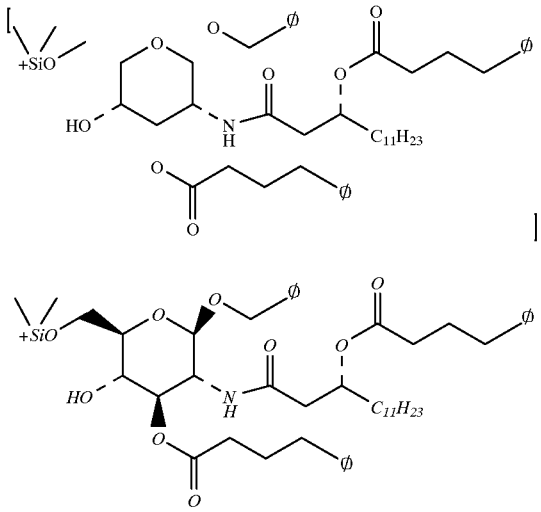

t-Butyldimethylsilyl chloride (338 mg) and 4-(N,N-dimethylamino)pyridine (11 mg) were added to a solution of the compound (691 mg) prepared in reference example 3 dissolved into dry pyridine (15 ml). The mixture was stirred for 7.5 hrs in an atmosphere of nitrogen at room temperature. The reaction solution was evaporated. The residue was purified by column chromatography on silica gel ($CH_2Cl_2$:$CH_3OH$=98.2) to give the title compound (936 mg) having the following physical data.

TABLE VI

| No. | $R^b$, $R^c$, $R^d$ | Name | Starting Material | TLC | IR ($cm^{-1}$) |
|---|---|---|---|---|---|
| 4 (a) | 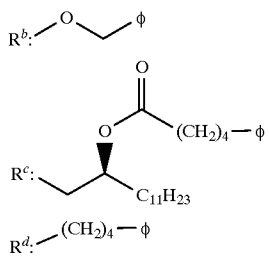 | benzyl 2-deoxy-2-[3S-(5-phenyl-pentanoyloxy)tetradecanoyl]amino-3-O-(5-phenylpentanoyl)-6-O-t-butyl-dimethylsilyl-β-D-glucopyranoside | Reference Example 3 (a) | Rf 0.75 ($CH_2Cl_2$: $CH_3OH$ = 97:3) | |
| 4 (b) | 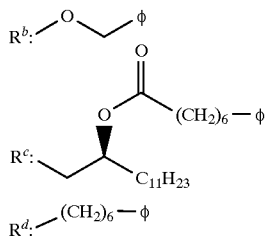 | benzyl 2-deoxy-2-[3S-(7-phenyl-heptanoyloxy)tetradecanoyl]amino-3-O-(7-phenylheptanoyl)-6-O-t-butyl-dimethylsilyl-β-D-glucopyranoside | Reference Example 3 (b) | Rf 0.80 ($CH_2Cl_2$: $CH_3OH$ = 97:3) | |
| 4 (c) | 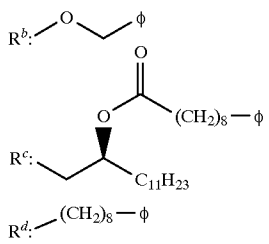 | benzyl 2-deoxy-2-[3S-(9-phenyl-nonanoyloxy)tetradecanoyl]amino-3-O-(9-phenylnonanoyl)-6-O-t-butyl-dimethylsilyl-β-D-glucopyranoside | Reference Example 3 (c) | Rf 0.85 (EtOAc n-$C_6H_{14}$ = 1:1) | |

TABLE VI-continued

| No. | $R^b$, $R^c$, $R^d$ | Name | Starting Material | TLC | IR ($cm^{-1}$) |
|---|---|---|---|---|---|
| 4 (d) | 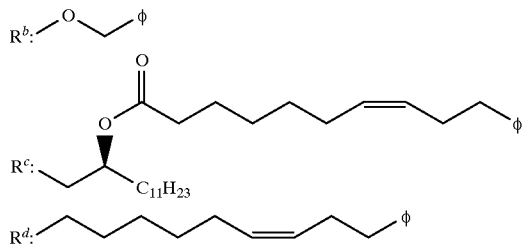 | benzyl 2-deoxy-2-[3S-(10-phenyl-7Z-decenoyloxy)tetradecanoyl]amino-3-O-(10-phenyl-7Z-decenoyl)-6-O-t-butyl-dimethylsilyl-β-D-glucopyranoside | Reference Example 3 (d) | Rf 0.94 ($CH_2Cl_2$: EtOAc = 97:3) | |
| 4 (e) | 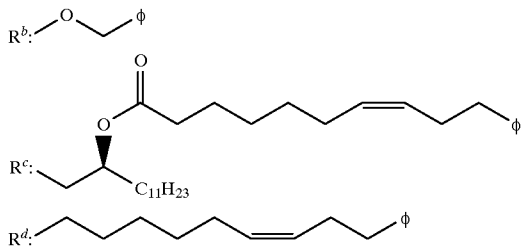 | benzyl 2-deoxy-2-[3R-(10-phenyl-7Z-decenoyloxy)tetradecanoyl]amino-3-O-(10-phenyl-7Z-decenoyl)-6-O-t-butyl-dimethylsilyl-β-D-glucopyranoside | Reference Example 3 (e) | | ν 3460, 2940, 2860, 1730, 1690, 1510, 1460, 1370, 1320, 1260, 1160, 1130, 1080, 840, 700 |
| 4 (f) | 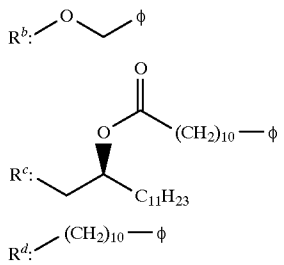 | benzyl 2-deoxy-2-[3S-(11-phenyl-undecanoyloxy)tetradecanoyl]amino-3-O-(11-phenylundecanoyl)-6-O-t-butyl-dimethylsilyl-β-D-glucopyranoside | Reference Example 3 (f) | | |

TABLE VI-continued

| No. | $R^b$, $R^c$, $R^d$ | Name | Starting Material | TLC | IR ($cm^{-1}$) |
|---|---|---|---|---|---|
| 4 (g) | 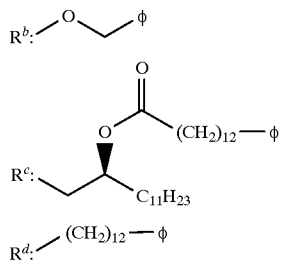 | benzyl 2-deoxy-2-[3S-(13-phenyl-tridecanoyloxy)tetradecanoyl]amino-3-O-(13-phenyltridecanoyl)-6-O-t-butyl-dimethylsilyl-β-D-glucopyranoside | Reference Example 3 (g) | Rf 0.84 ($CH_2Cl_2$: n-$C_6H_{14}$ = 1:1) | |
| [4 (h) | 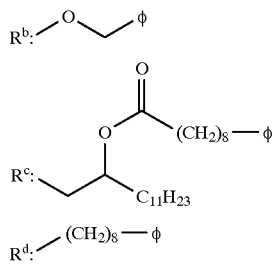 ] | | | | |
| *4 (h)* | 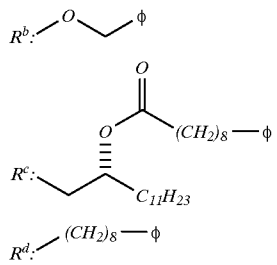 | benzyl 2-deoxy-2-[3R-(9-phenyl-nonanoyloxy)tetradecanoyl]amino-3-O-(9-phenylnonanoyl)-6-O-t-butyl-dimethylsilyl-β-D-glucopyranoside | Reference Example 3 (h) | | ν 3470, 3250, 2920, 2850, 1730, 1650, 1550 |

TABLE VI-continued

| No. | $R^b$, $R^c$, $R^d$ | Name | Starting Material | TLC | IR ($cm^{-1}$) |
|---|---|---|---|---|---|
| 4 (i) | 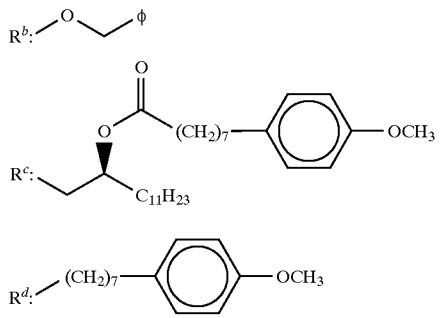 | benzyl 2-deoxy-2-[3S-[8-(4-methoxyphenyl)octanoyloxy]tetradecanoyl]amino-3-O-[8-(4-methoxyphenyl)octanoyl]-6-O-t-butyldimethylsilyl-β-D-glucopyranoside | Reference Example 3 (i) | Rf 0.74 (EtOAc: n-$C_6H_{14}$ = 3:5) | ν 3500, 3290, 2920, 2850, 1730, 1650, 1610 |
| 4 (j) | 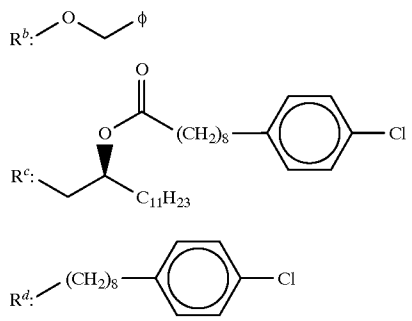 | benzyl 2-deoxy-2-[3S-[9-(4-chlorophenyl)nonanoyloxy]tetradecanoyl]amino-3-O-[9-(4-chlorophenyl)nonanoyl]-6-O-t-butyldimethylsilyl-β-D-glucopyranoside | Reference Example 3 (j) | Rf 0.70 (EtOAc: n-$C_6H_{14}$ = 3:5) | ν (liquid film) 3500, 3270, 2910, 2840, 1730, 1650, 1540 |
| 4 (k) | 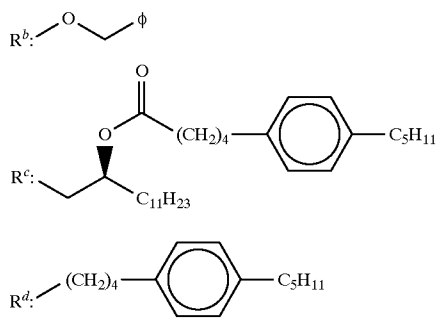 | benzyl 2-deoxy-2-[3S-[5-(4-pentylphenyl)pentanoyloxy]tetradecanoyl]amino-3-O-(5-(4-pentylphenyl)pentanoyl]-6-O-t-butyldimethylsilyl-β-D-glucopyranoside | Reference Example 3 (k) | Rf 0.81 (EtOAc: n-$C_6H_{14}$ = 3:5) | |

TABLE VI-continued

| No. | $R^b$, $R^c$, $R^d$ | Name | Starting Material | TLC | IR ($cm^{-1}$) |
|---|---|---|---|---|---|
| 4 (l) | 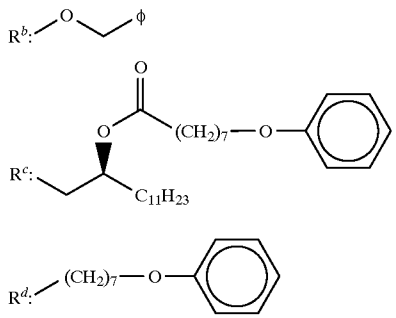 | benzyl 2-deoxy-2-[3S-(8-phenoxy-octanoyloxy)tetradecanoyl]amino-3-O-(8-phenoxyoctanoyl)-6-O-6-butyl-dimethylsilyl-β-D-glucopyranoside | Reference Example 3 (l) | Rf 0.72 (EtOAc: n-$C_6H_{14}$ = 3:5) | ν (liquid film) 3450, 3270, 2910, 2850, 1730, 1650, 1600 |
| 4 (m) | 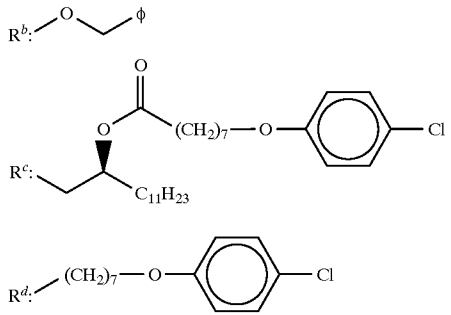 | benzyl 2-deoxy-2-[3S-[8-(4-chloro-phenoxy)octanoyloxy]tetradecanoyl] amino-3-O-[8-(4-chlorophenoxy) octanoyl]-6-O-t-butyldimethylsilyl-β-D-glucopyranoside | Reference Example 3 (m) | Rf 0.75 (EtOAc: n-$C_6H_{14}$ = 3:5) | ν (liquid film) 3300, 2920, 2850, 1730, 1650, 1540, 1490, 1460 |

TABLE VI-continued

| No. | $R^b$, $R^c$, $R^d$ | Name | Starting Material | TLC | IR ($cm^{-1}$) |
|---|---|---|---|---|---|
| 4 (n) | 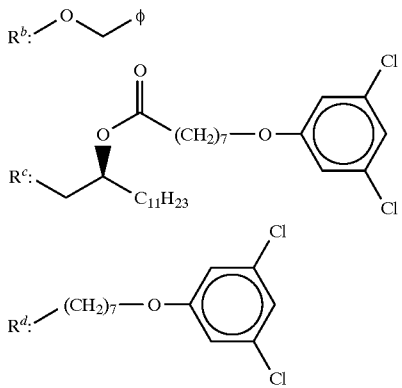 | benzyl 2-deoxy-2-[3S-[8-(3,5-dichloro-phenoxy)octanoyloxy]tetradecanoyl] amino-3-O-[8-(3,5-dichlorophenoxy) octanoyl]-6-O-t-butyldimethylsilyl-β-D-glucopyranoside | Reference Example 3 (n) | Rf 0.59 (EtOAc: n-$C_6H_{14}$ = 3:5) | ν (liquid film) 3300, 2920, 2860, 1730, 1650, 1590, 1570 |
| 4 (o) | 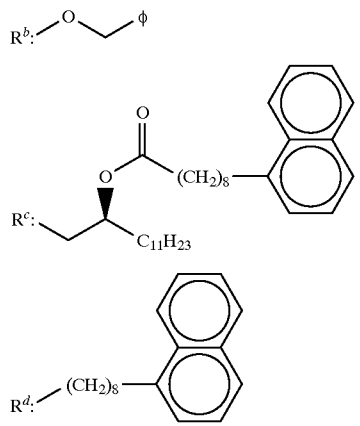 | benzyl 2-deoxy-2-[3S-[9-(1-naphthyl) nonanoyloxy]tetradecanoyl]amino-3-O-[9-(1-naphthyl)nonanoyl]-6-O-t-butyl-dimethylsilyl-β-D-glucopyranoside | Reference Example 3 (o) | Rf 0.62 (EtOAc: n-$C_6H_{14}$ = 3:5) | ν (liquid film) 3450, 3280, 2910, 2850, 1730, 1660 |

TABLE VI-continued

| No. | $R^b$, $R^c$, $R^d$ | Name | Starting Material | TLC | IR ($cm^{-1}$) |
|---|---|---|---|---|---|
| 4 (p) | 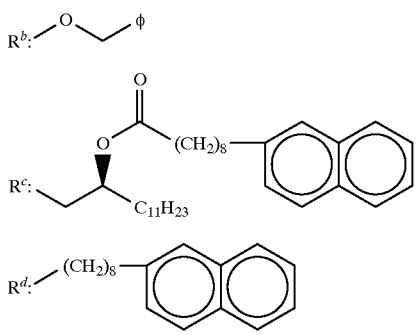 | benzyl 2-deoxy-2-[3S-[9-(2-naphthyl)-nonanoyloxy]tetradecanoyl]amino-3-O-[9-(2-naphthyl)nonanoyl]-6-O-t-butyl-dimethylsilyl-β-D-glucopyranoside | Reference Example 3 (p) | | ν (liquid film) 3300, 2910, 2820, 1730, 1650, 1540 |
| 4 (q) | 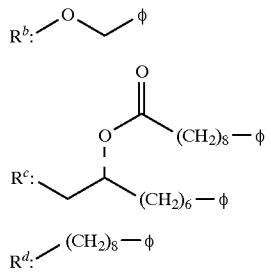 | benzyl 2-deoxy-2-[3R-(9-phenyl-nonanoyloxy)-9-phenylnonanoyl]amino-3-O-(9-phenylnonanoyl)-6-O-t-butyl-dimethylsilyl-β-D-glucopyranoside | Reference Example 3 (q) | Rf 0.68 (EtOAc: n-$C_6H_{14}$ = 1:2) | ν (liquid film) 3500, 3280, 2920, 2850, 1730, 1650, 1640 |
| 4 (r) | 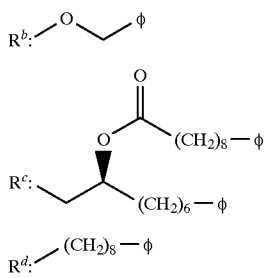 | benzyl 2-deoxy-2-[3S-(9-phenyl-nonanoyloxy)-9-phenylnonanoyl]amino-3-O-(9-phenylnonanoyl)-6-O-t-butyl-dimethylsilyl-β-D-glucopyranoside | Reference Example 3 (r) | Rf 0.75 (EtOAc: n-$C_6H_{14}$ = | ν (liquid film) 3500, 3400, 2910, 1720, 1650, 1600 |

TABLE VI-continued

| No. | $R^b$, $R^c$, $R^d$ | Name | Starting Material | TLC | IR ($cm^{-1}$) |
|---|---|---|---|---|---|
| 4 (s) | 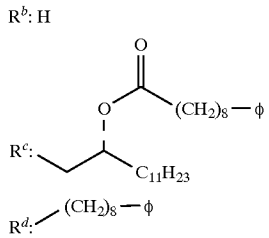 | 2-deoxy-2-[3R-(9-phenylnonanoyloxy) tetradecanoyl]amino-3-O-(9-phenyl-nonanoyl)-6-O-t-butyldimethylsilyl-1,5-anhydro-D-glucitol | Reference Example 3 (s) | Rf 0.17 (n-$C_6H_{14}$: EtOAc = 3:1) | |
| 4 (t) | 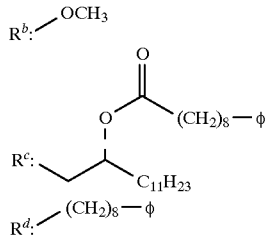 | methyl 2-deoxy-2-[3R-(9-phenyl-nonanoyloxy)tetradecanoyl]amino-3-O-(9-phenylnonanoyl)-6-O-t-butyl-dimethylsilyl-β-D-glucopyranoside | Reference Example 3 (u) | Rf 0.41 (n-$C_6H_{14}$: EtOAc = 2:1) | |
| 4 (u) | 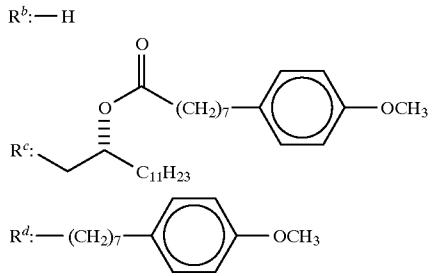 | 2-deoxy-2-[3R-[8-(4-methoxy-phenyl)octanoyloxy]tetradecanoyl] amino-3-O-[8-(4-methoxyphenyl) octanoyl]-6-O-t-butyldimethylsilyl-1,5-anhydro-D-glucitol | Reference Example 3 (v) | Rf 0.19 (n-$C_6H_{14}$: EtOAc = 3:1) | ν 3500, 1730, 1650, 1610 |

TABLE VI-continued

| No. | $R^b$, $R^c$, $R^d$ | Name | Starting Material | TLC | IR ($cm^{-1}$) |
|---|---|---|---|---|---|
| 4 (v) | $R^b$:—H<br>$R^c$: 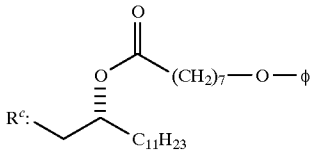 <br>$R^d$:—$(CH_2)_7$—O—ϕ | 2-deoxy-2-[3R-(8-phenoxyoctanoyloxy) tetradecanoyl]amino-3-O-(8-phenoxy-octanoyl)-6-O-t-butyldimethylsilyl-1,5-anhydro-D-glucitol | Reference Example 3 (w) | Rf 0.20 (n-$C_6H_{14}$: EtOAc = 3:1) | ν 3430, 1728, 1650, 1600 |
| 4 (w) | $R^b$:—H<br>$R^c$: 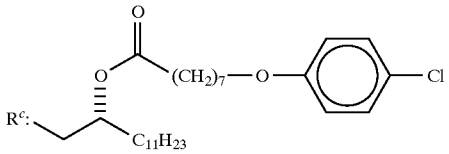 <br>$R^d$:—$(CH_2)_7$—O— 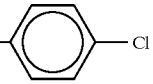 Cl | 2-deoxy-2-[3R-[8-(4-chlorophenoxy) octanoyloxy]tetradecanoyl]amino-3-O-[8-(4-chlorophenoxy)octanoyl]-6-O-t-butyldimethylsilyl-1,5-anhydro-D-glucitol | Reference Example 3 (x) | Rf 0.21 (n-$C_6H_{14}$: EtOAc = 3:1) | ν ($CHCl_3$ solution) 3300, 1730, 1650, 1540 |

TABLE VI-continued

| No. | $R^b$, $R^c$, $R^d$ | Name | Starting Material | TLC | IR ($cm^{-1}$) |
|---|---|---|---|---|---|
| 4 (x) | $R^b$: — H<br>$R^c$: 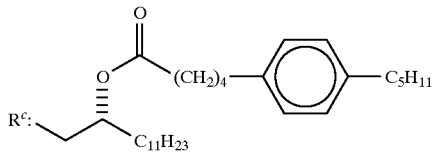 <br>$R^d$: — $(CH_2)_4$ — $C_5H_{11}$ | 2-deoxy-2-[3R-[5-(4-pentylphenyl) pentanoyloxy]tetradecanoyl]amino-3-O-[5-(4-pentylphenyl)pentanoyl]-6-O-t-butyldimethylsilyl-1,5-anhydro-D-glucitol | Reference Example 3 (y) | Rf 0.22 (n-$C_6H_{14}$: EtOAc = 3:1) | ν ($CHCl_3$ solution) 3430, 1730, 1652, 1550 |
| 4 (z) | $R^b$: — H<br>$R^c$: 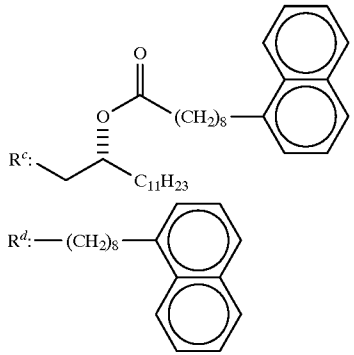 <br>$R^d$: — $(CH_2)_8$ | 2-deoxy-2-[3R-[9-(1-naphthyl) nonanoyloxy]tetradecanoyl]amino-3-O-[9-(1-naphthyl)nonanoyl]-6-O-t-butyl-dimethylsilyl-1,5-anhydro-D-glucitol | Reference Example 3 (z) | Rf 0.19 (n-$C_6H_{14}$: EtOAc = 3:1) | ν ($CHCl_3$ solution) 3432, 1732, 1652, 1543, 840, 785 |

TLC: Rf 0.85 ($CH_2Cl_2$:$CH_3OH$=97:3);

IR: ν 3350, 2940, 2860, 1720, 1680, 1490, 1450, 1360, 1250, 1130, 1070, 830, 690 $cm^{-1}$.

REFERENCE EXAMPLES 4(a)~4(z)

By the same procedure as in reference example 4, using the starting materials specified, the following compounds having the physical data shown in Table VI were prepared:

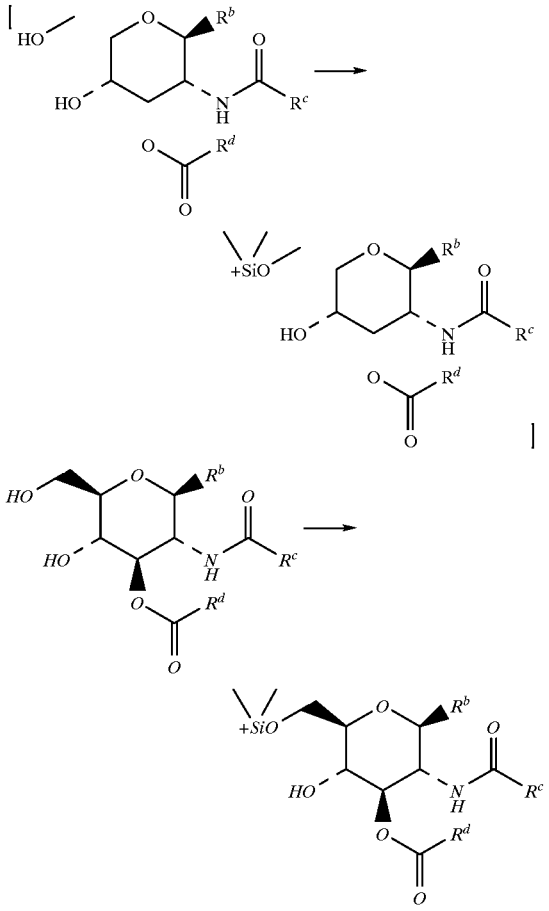

REFERENCE EXAMPLE 5

Synthesis of 2-deoxy-2-[3R-(4-phenylbutyryloxy) tetradecanoyl]amino-3-O-(4-phenylbutyryl)-6-O-t-butyldimethylsilyl-D-glucopyranose

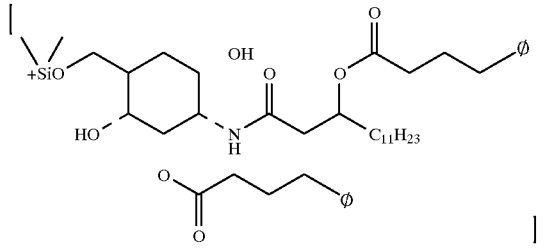

-continued

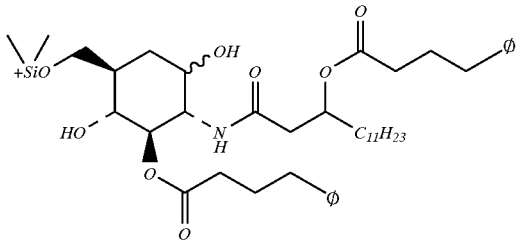

To a stirring solution of the compound (736 mg) prepared in reference example 4 dissolved into THF, palladium-carbon (content 10%; 368 mg) was added in small portions. In an atmosphere of hydrogen, the mixture was stirred vigorously for 24 hrs at 50° C. After reaction, the reaction mixture was filtered. The filtrate was evaporated to give the title compound (653 mg) having the following physical data.

TLC: Rf 0.64 ($CH_2Cl_2$:$CH_3OH$=9:1);

IR: ν 3350, 2920, 2840, 1720, 1640, 1540, 1440, 1250, 1130, 1070, 1050, 800, 740, 690 $cm^{-1}$.

REFERENCE EXAMPLES 5(a)~5(p)

By the same procedure as reference example 5, using the starting materials specified, the following compounds having the physical data shown in Table VII were prepared:

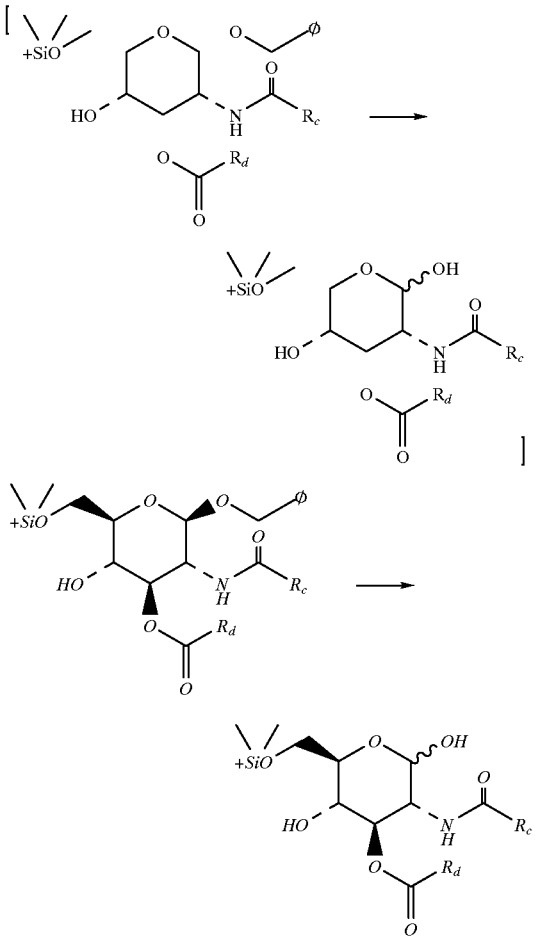

TABLE VII

| No. | $R^c$, $R^d$ | Name | Starting Material | TLC | IR ($cm^{-1}$) |
|---|---|---|---|---|---|
| 5 (a) | 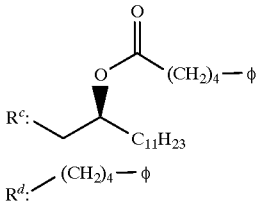 | 2-deoxy-2-[3S-(5-phenylpentanoyloxy) tetradecanoyl]amino-3-O-(5-phenylpentanoyl)-6-O-t-butyldimethylsilyl-D-glucopyranose | Reference Example 4 (a) | Rf 0.36 ($CH_2Cl_2$: $CH_3OH$ = 97:3) | |
| 5 (b) | 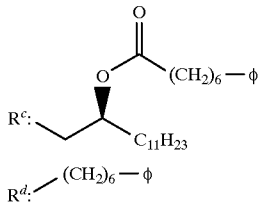 | 2-deoxy-2-[3S-(7-phenylheptanoyloxy) tetradecanoyl]amino-3-O-(7-phenylheptanoyl)-6-O-t-butyldimethylsilyl-D-glucopyranose | Reference Example 4 (b) | Rf 0.34 ($CH_2Cl_2$: $CH_3OH$ = 97:3) | |
| 5 (c) | 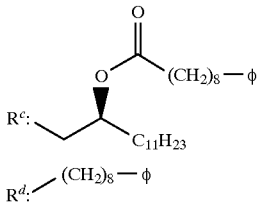 | 2-deoxy-2-[3S-(9-phenylnonanoyloxy) tetradecanoyl]amino-3-O-(9-phenylnonanoyl)-6-O-t-butyldimethylsilyl-D-glucopyranose | Reference Example 4 (c) | Rf 0.46 ($CH_2Cl_2$: EtOAc = 9:1) | |
| 5 (d) | 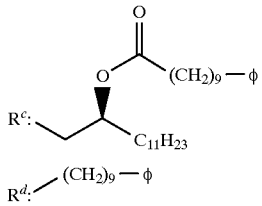 | 2-dexoy-2-[3S-(10-phenyldecanoyloxy) tetradecanoyl]amino-3-O-(10-phenyldecanoyl)-6-O-t-butyldimethylsilyl-D-glucopyranose | Reference Example 4 (d) | Rf 0.42 ($CH_2Cl_2$: $CH_3OH$ = 97:3) | |

TABLE VII-continued

| No. | $R^c$, $R^d$ | Name | Starting Material | TLC | IR ($cm^{-1}$) |
|---|---|---|---|---|---|
| 5 (e) | 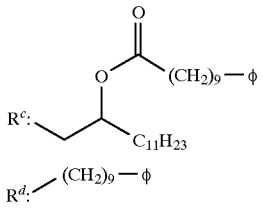 | 2-deoxy-2-[3R-(10-phenyldecanoyloxy) tetradecanoyl]amino-3-O-(10-phenyldecanoyl)-6-O-t-butyldimethylsilyl-D-glucopyranose | Reference Example 4 (e) | | ν 3460, 2930, 2860, 1720, 1670, 1500, 1450, 1260, 1090, 840 |
| 5 (f) | 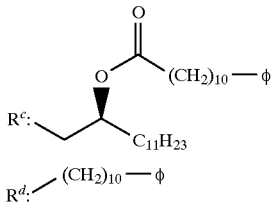 | 2-deoxy-2-[3S-(11-phenylundecanoyloxy) tetradecanoyl]amino-3-O-(11-phenylundecanoyl)-6-O-t-butyldimethylsilyl-D-glucopyranose | Reference Example 4 (f) | Rf 0.36 ($CH_2Cl_2$: EtOAc = 9:1) | |
| 5 (g) | 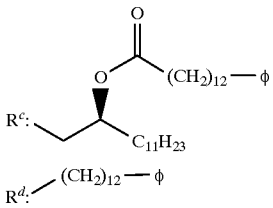 | 2-deoxy-2-[3S-(13-phenyltridecanoyloxy) tetradecanoyl]amino-3-O-(13-phenyltridecanoyl)-6-O-t-butyldimethylsilyl-D-glucopyranose | Reference Example 4 (g) | Rf 0.43 ($CH_2Cl_2$: $CH_3OH$ = 9:1) | |
| 5 (h) | 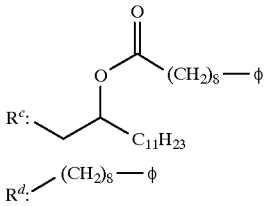 | 2-deoxy-2-[3R-(9-phenylnonanoyloxy) tetradecanoyl]amino-3-O-(9-phenylnonanoyl)-6-O-t-butyldimethylsilyl-D-glucopyranose | Reference Example 4 (h) | Rf 0.56 (EtOAc: n-$C_6H_{14}$ = 3:5) | |

TABLE VII-continued

| No. | $R^c$, $R^d$ | Name | Starting Material | TLC | IR ($cm^{-1}$) |
|---|---|---|---|---|---|
| 5 (i) | 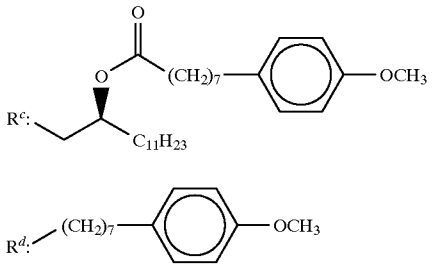 | 2-deoxy-2-[3S-[8-(4-methoxyphenyl)octanoyloxy] tetradecanoyl]amino-3-O-[8-(4-methoxyphenyl) octanoyl]-6-O-t-butyldimethylsilyl-D-glucopyranose | Reference Example 4 (i) | Rf 0.53 (EtOAc: n-$C_6H_{14}$ = 3:5) | |
| 5 (j) | 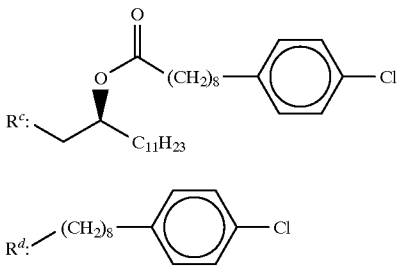 | 2-deoxy-2-[3S-[9-(4-chlorophenyl)nonanoyloxy] tetradecanoyl]amino-3-O-[9-(4-chlorophenyl) nonanoyl]-6-O-t-butyldimethylsilyl-D-glucopyranose | Reference Example 4 (j) | | |
| 5 (k) | 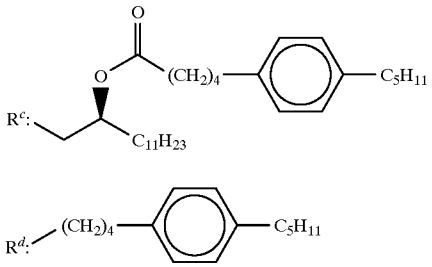 | 2-deoxy-2-[3S-[5-(4-pentylphenyl)pentanoyloxy] tetradecanoyl]amino-3-O-[5-(4-pentylphenyl) pentanoyl]-6-O-t-butyldimethylsilyl-β-D-glucopyranose | Reference Example 4 (k) | Rf 0.67 ($CH_2CH_2$: $CH_3OH$ = 6:1) | |

TABLE VII-continued

| No. | $R^c$, $R^d$ | Name | Starting Material | TLC | IR ($cm^{-1}$) |
|---|---|---|---|---|---|
| 5 (l) | 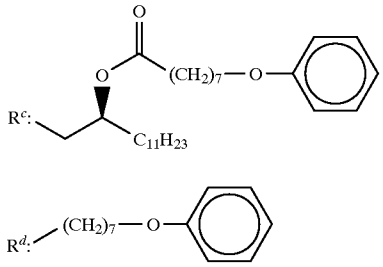 | 2-deoxy-2-[3S-(8-phenoxyoctanoyloxy) tetradecanoyl]amino-3-O-(8-phenoxyoctanoyl-6-O-t-butyldimethylsilyl-D-glucopyranose | Reference Example 4 (l) | Rf 0.53 (EtOAc: n-$C_6H_{14}$ = 3:5) | |
| 5 (m) | 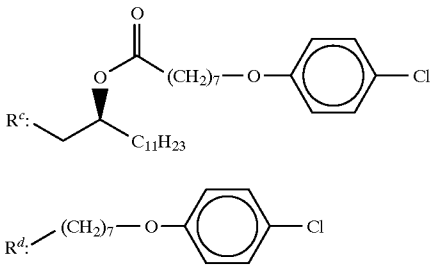 | 2-deoxy-2-[3S-[8-(4-chlorophenoxy)octanoyloxy] tetradecanoyl]amino-3-O-[8-(4-chlorophenoxy) octanoyl]-6-O-t-butyldimethylsilyl-D-glucopyranose | Reference Example 4 (m) | | |
| 5 (n) | 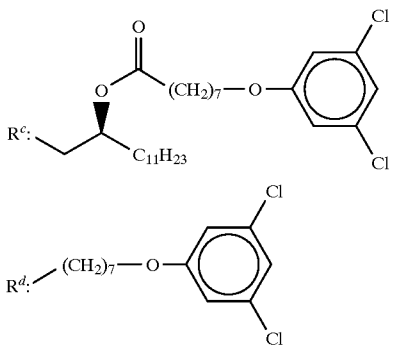 | 2-deoxy-2-[3S-[8-(3,5-dichlorophenoxy) octanoyloxy]tetradecanoyl]amino-3-O-[8-(3,5-dichlorophenoxy)octanoyl]-6-O-t-butyldimethylsilyl-D-glucopyranose | Reference Example 4 (n) | | |

TABLE VII-continued
| No. | $R^c$, $R^d$ | Name | Starting Material | TLC | IR ($cm^{-1}$) |
|---|---|---|---|---|---|
| 5 (o) | 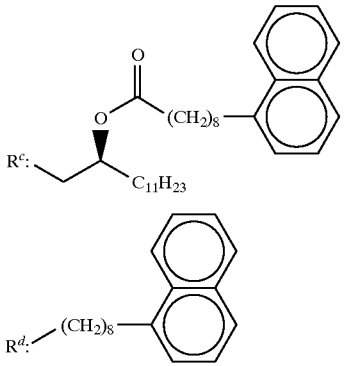 | 2-deoxy-2-[3S-[9-(1-naphthyl)nonanoyloxy] tetradecanoyl]amino-3-O-[9-(1-naphthyl) nonanoyl]-6-O-t-butyldimethylsilyl-D-glucopyranose | Reference Example 4 (o) | Rf 0.50 (EtOAc: n-$C_6H_{14}$ = 3:5) | |
| 5 (p) | 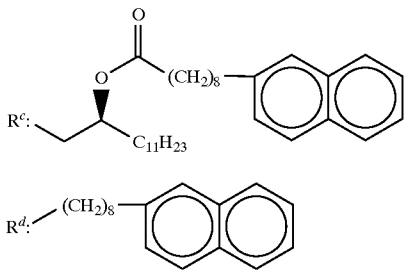 | 2-deoxy-2-[3S-[9-(2-naphthyl)nonanoyloxy] tetradecanoyl]amino-3-O-[9-(2-naphthyl) nonanoyl]-6-O-t-butyldimethylsilyl-D-glucopyranose | Reference Example 4 (p) | | |

TABLE VII-continued

| No. | $R^c$, $R^d$ | Name | Starting Material | TLC | IR ($cm^{-1}$) |
|---|---|---|---|---|---|
| 5 (q) | 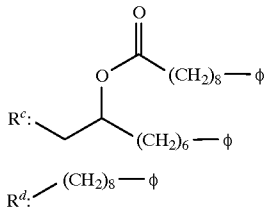 | 2-deoxy-2-[3R-(9-phenylnonanoyloxy)-9-phenylnonanoyl]amino-3-O-(9-phenylnonanoyl)-6-O-t-butyldimethylsilyl-D-glucopyranose | Reference Example 4 (q) | Rf 0.57 (EtOAc: n-$C_6H_{14}$ = 1:2) | ν (liquid film) 3450, 3350, 2910, 2850, 1720, 1650, 1600 |
| 5 (r) | 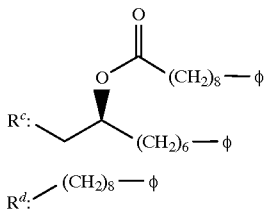 | 2-deoxy-2-[3S-(9-phenylnonanoyloxy)-9-phenylnonanoyl]amino-3-O-(9-phenylnonanoyl)-6-O-t-butyldimethylsilyl-D-glucopyranose | Reference Example 4 (r) | Rf 0.40 (EtOAc: n-$C_6H_{14}$ = 1:2) | |

REFERENCE EXAMPLE 6

Synthesis of *Pyridine Salt of* 2-deoxy-2-[3R-(4-phenylbutyryloxy)tetradecanoyl]amino-3-O-(4-phenylbutyryl)-4-O-sulfo-6-O-t-butyldimethylsilyl-D-glucopyranose

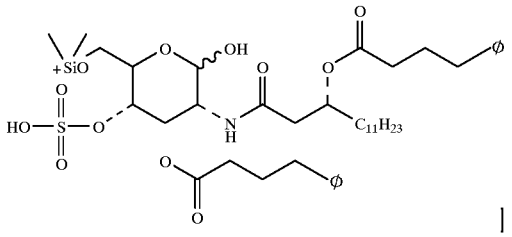

-continued

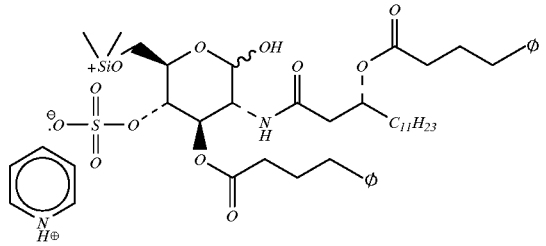

In an atmosphere of nitrogen, sulfur trioxide-pyridine complex (230 mg) was added to a solution of the compound (653 mg) prepared in reference example 5 dissolved into dry pyridine. The mixture was stirred for 4 hrs at room temperature, and concentrated. To the reside, toluene was added and the solution was evaporated to give the title compounds.

TABLE VIII

| No. | $R^c$,$R^d$ | Name - *Pyridine Salts of:* | Starting Material | TLC |
|---|---|---|---|---|
| [6 (a) | 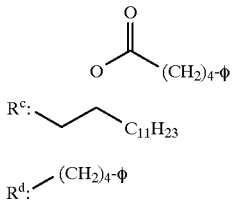 | ] 2-deoxy-2-[3S-(5-phenylpentanoyloxy) tetradecanoyl]amino-3-O-(5-phenylpentanoyl)-4-O-sulfo-6-O-t-butyldimethylsilyl-D-glucopyranose | Reference Example 5 (a) | |
| *6 (a)* | 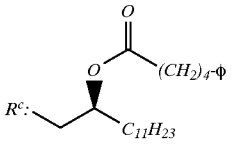 | | | |
| [6 (b) | 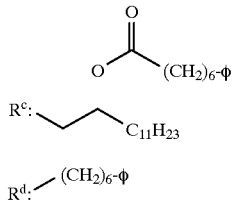 | ] 2-deoxy-2-[3S-(7-phenylheptanoyloxy) tetradecanoyl]amino-3-O-(7-phenylheptanoyl)-4-O-sulfo-6-O-t-butyldimethylsilyl-D-glucopyranose | Reference Example 5 (b) | |
| *6 (b)* | 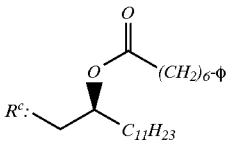 | | | |

TABLE VIII-continued

| No. | $R^c$,$R^d$ | Name - *Pyridine Salts of:* | Starting Material | TLC |
|---|---|---|---|---|
| [6 (c) | 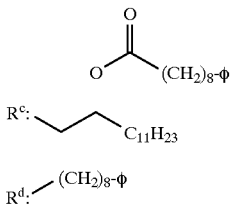 | 2-deoxy-2-[3S-(9-phenylnonanoyloxy) tetradecanoyl]amino-3-O-(9-phenylnonanoyl)-4-O-sulfo-6-O-t-butyldimethylsilyl-D-glucopyranose ] | Reference Example 5 (c) | |
| *6 (c)* | 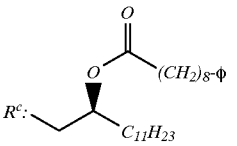 | | | |
| [6 (d) | 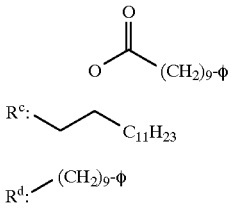 | 2-deoxy-2-[3S-(10-phenyldecanoyloxy) tetradecanoyl]amino-3-O-(10-phenyldecanoyl)-4-O-sulfo-6-O-t-butyldimethylsilyl-D-glucopyranose ] | Reference Example 5 (d) | |
| *6 (d)* | 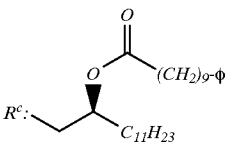 | | | |
| 6 (e) | 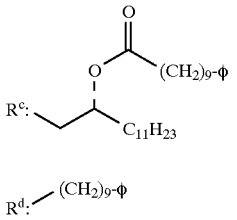 | 2-deoxy-2-[3R-(10-phenyldecanoyloxy) tetradecanoyl]amino-3-O-(10-phenyldecanoyl)-4-O-sulfo-6-O-t-butyldimethylsilyl-D-glucopyranose | Reference Example 5 (e) | |
| 6 (f) | 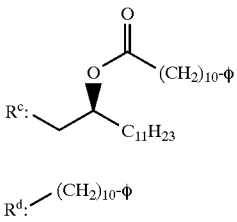 | 2-deoxy-2-[3S-(11-phenylundecanoyloxy) tetradecanoyl]amino-3-O-(11-phenylundecanoyl)-4-O-sulfo-6-O-t-butyldimethylsilyl-D-glucopyranose | Reference Example 5 (f) | |
| 6 (g) | 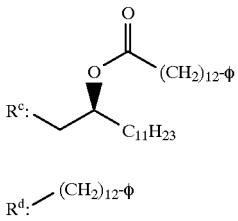 | 2-deoxy-2-[3S-(13-phenyltridecanoyloxy) tetradecanoyl]amino-3-O-(13-phenyltridecanoyl)-4-O-sulfo-6-O-t-butyldimethylsilyl-D-glucopyranose | Reference Example 5 (g) | |

TABLE VIII-continued

| No. | $R^c$,$R^d$ | Name - *Pyridine Salts of:* | Starting Material | TLC |
|---|---|---|---|---|
| 6 (h) | 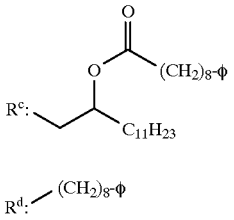 | 2-deoxy-2-[3R-(9-phenylnonanoyloxy) tetradecanoyl]amino-3-O-(9-phenylnonanoyl)-4-O-sulfo-6-O-t-butyldimethylsilyl-D-glucopyranose | Reference Example 5 (h) | |
| [6 (i) | 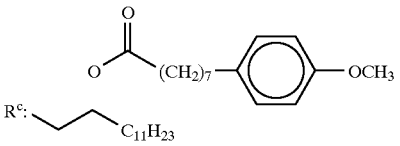 ] | 2-deoxy-2-[3S-[8-(4-methoxyphenyl)octanoyloxy] tetradecanoyl]amino-3-O-[8-(4-methoxyphenyl) octanoyl]-4-O-sulfo-6-O-t-butyldimethylsilyl-D-glucopyranose | Reference Example 5 (i) | Rf 0.41 (EtOAc: n-$C_6H_{14}$ = 1:6) |
| *6 (i)* | 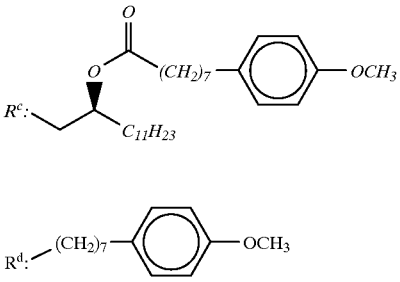 | | | |
| [6 (j) | 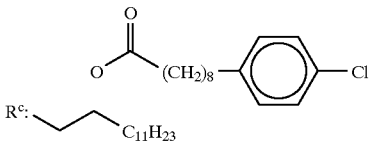 ] | 2-deoxy-2-[3S-[9-(4-chlorophenyl)nonanoyloxy] tetradecanoyl]amino-3-O-[9-(4-chlorophenyl) nonanoyl]-4-O-sulfo-6-O-t-butyldimethylsilyl-D-glucopyranose | Reference Example 5 (j) | |
| *6 (j)* | 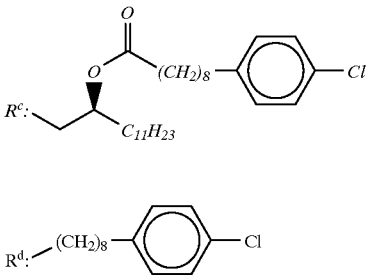 | | | |
| [6 (k) | 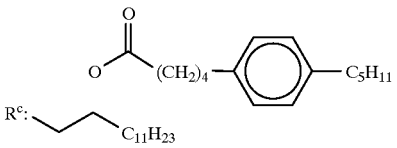 ] | 2-deoxy-2-[3S-[5-(4-pentylphenyl)pentanoyloxy] tetradecanoyl]amino-3-O-[5-(4-pentylphenyl) pentanoyl]-4-O-sulfo-6-O-t-butyldimethylsilyl-D-glucopyranose | Reference Example 5 (k) | Rf 0.30 ($CH_2Cl_2$: $CH_3OH$ = 6:1) |
| *6 (k)* | 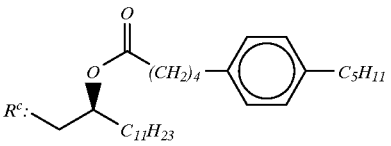 | | | |

TABLE VIII-continued

| No. | $R^c$,$R^d$ | Name - *Pyridine Salts of:* | Starting Material | TLC |
|---|---|---|---|---|
| | $R^d$: $(CH_2)_4$ — $C_5H_{11}$ | | | |
| [6 (l) | O, O, $(CH_2)_7$ — O, $R^c$: $C_{11}H_{23}$ | ] 2-deoxy-2-[3S-(8-phenoxyoctanoyloxy) tetradecanoyl]amino-3-O-(8-phenoxyoctanoyl)-4-O-sulfo-6-O-t-butyldimethylsilyl-D-glucopyranose | Reference Example 5 (l) | Rf 0.61 ($CH_2Cl_2$: $CH_3OH$ = 6:1) |
| *6 (l)* | *O*, *O*, $(CH_2)_7$ — *O*, $R^c$: $C_{11}H_{23}$ | | | |
| | $R^d$: $(CH_2)_7$ — O | | | |
| [6 (m) | O, O, $(CH_2)_7$ — O, Cl, $R^c$: $C_{11}H_{23}$ | ] 2-deoxy-2-[3S-[8-(4-chlorophenoxy)octanoyloxy] tetradecanoyl]amino-3-O-[8-(4-chlorophenoxy) octanoyl]-4-O-sulfo-6-O-t-butyldimethylsilyl-D-glucopyranose | Reference Example 5 (m) | |
| *6 (m)* | *O*, *O*, $(CH_2)_7$ — *O*, *Cl*, $R^c$: $C_{11}H_{23}$ | | | |
| | $R^d$: $(CH_2)_7$ — O, Cl | | | |
| [6 (n) | O, O, $(CH_2)_7$ — O, Cl, Cl, $R^c$: $C_{11}H_{23}$ | ] 2-deoxy-2-[3S-[8-(3,5-dichlorophenoxy) octanoyloxy]tetradecanoyl]amino-3-O-[8-(3,5-dichlorophenoxy)octanoyl]-4-O-sulfo-6-O-t-butyldimethylsilyl-D-glucopyranose | Reference Example 5 (n) | |
| *6 (n)* | *O*, *O*, $(CH_2)_7$ — *O*, *Cl*, *Cl*, $R^c$: $C_{11}H_{23}$ | | | |

TABLE VIII-continued

| No. | $R^c$,$R^d$ | Name - *Pyridine Salts of:* | Starting Material | TLC |
|---|---|---|---|---|
| | 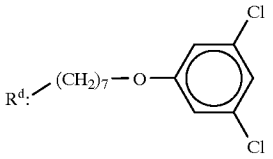 | | | |
| [6 (o) | 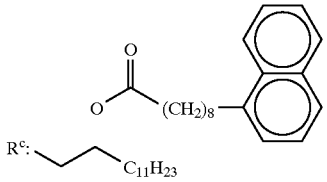 | ] 2-deoxy-2-[3S-[9-(1-naphthyl)nonanoyloxy] tetradecanoyl]amino-3-O-[9-(1-naphthyl) nonanoyl]-4-O-sulfo-6-O-t-butyldimethylsilyl-D-glucopyranose | Reference Example 5 (o) | Rf 0.69 ($CH_2CL_2$: $CH_3OH$ = 9:2) |
| *6 (o)* | 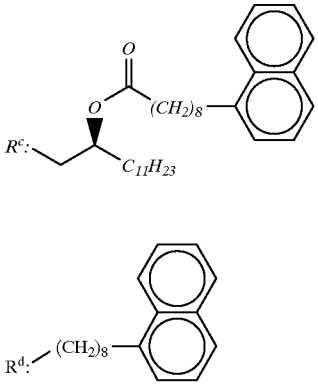 | | | |
| [6 (p) | 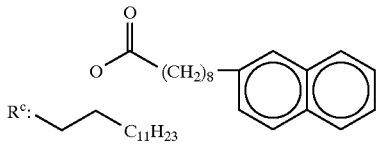 | ] 2-deoxy-2-[3S-[9-(2-naphthyl)nonanoyloxy] tetradecanoyl]amino-3-[9-(2-naphthyl) nonanyl]-4-O-sulfo-6-O-t-butyldimethylsilyl-D-glucopyranose | Reference Example 5 (p) | |
| *6 (p)* | 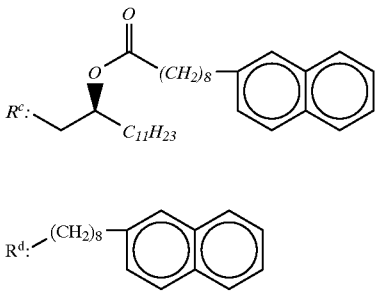 | | | |
| 6 (q) | 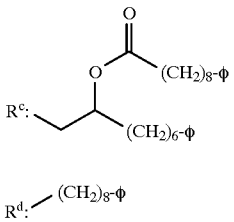 | 2-deoxy-2-[3R-[9-phenylnonanoyloxy-9-phenylnonanoyl]amino-3-O-(9-phenylnonanoyl)-4-O-sulfo-6-O-t-butyldimethylsilyl-D-glucopyranose | Reference Example 5 (q) | |

TABLE VIII-continued

| No. | $R^c$,$R^d$ | Name - *Pyridine Salts of:* | Starting Material | TLC |
|---|---|---|---|---|
| 6 (r) | 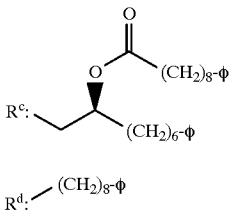 | 2-deoxy-2-[3S-(9-phenylnonanoyloxy-9-phenylnonanoyl]amino-3-O-(9-phenylnonanoyl)-4-O-sulfo-6-O-t-butyldimethylsilyl-D-glucopyranose | Reference Example 5 (r) | Rf 0.43 ($CH_2Cl_2$: $CH_3OH$ = 9:1) |

REFERENCE EXAMPLE 6(a)~[6(p)] *6(r)*

By the same procedure as in reference example 6, using the starting materials specified, the following compounds having the physical data shown in Table VIII were prepared:

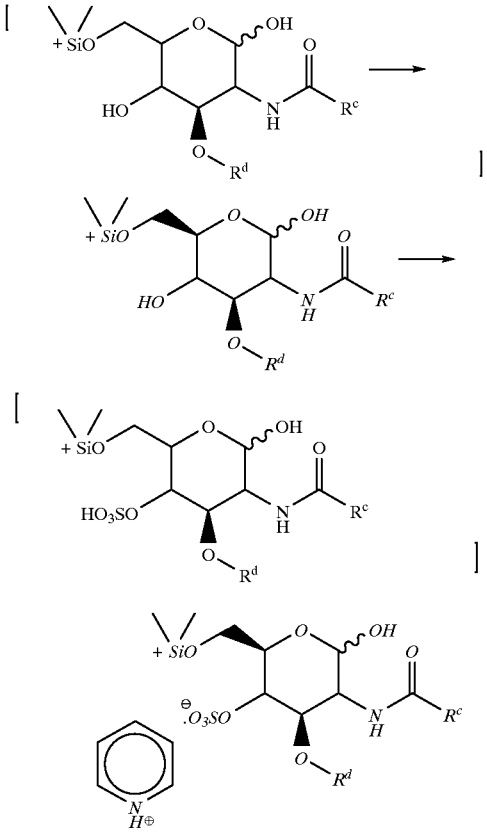

REFERENCE EXAMPLES 6(s)~6(y)

By the same procedure as in reference example 6, using the starting materials specified the following compounds having the physical data shown in Table IX were prepared:

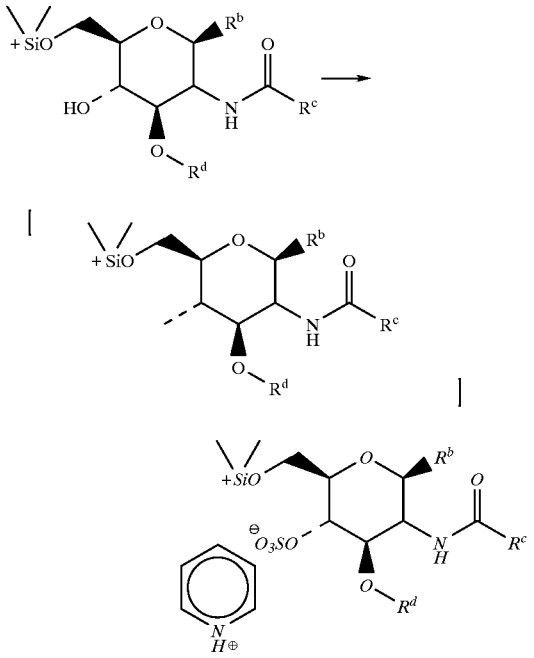

TABLE IX

| No. | $R^b$,$R^c$,$R^d$ | Name - *Pyridine Salts of:* | Starting Material | TLC |
|---|---|---|---|---|
| 6 (s) | $R^b$: H<br>$R^c$: 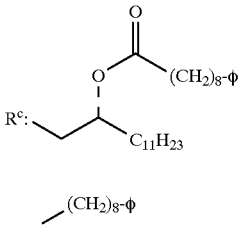 | 2-deoxy-2-[3R-(9-phenylnonanoyloxy) tetradecanoyl]amino-3-O-(9-phenylnonanoyl)-4-O-sulfo-6-O-t-butyldimethylsilyl-D-glucitol | Reference Example 4 (s) | Rf 0.22 ($CH_2Cl_2$: $CH_3OH$ = 9:1) |
| 6 (t) | $R^b$: 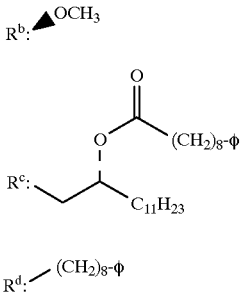 <br>$R^d$: $(CH_2)_8$-ϕ | methyl 2-deoxy-2-[3R-(9-phenylnonanoyloxy) tetradecanoyl]amino-3-O-(9-phenylnonanoyl)-4-O-sulfo-6-O-t-butyldimethylsilyl-β-D-glucopyranoside | Reference Example 4 (t) | Rf 0.20 ($CH_2Cl_2$: $CH_3OH$ = 9:1) |
| 6 (u) | $R^b$: H<br>$R^c$: 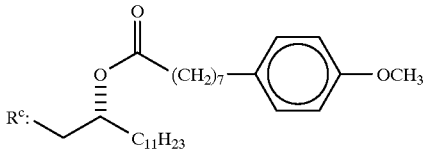 <br>$R^d$: 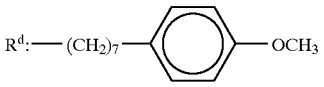 | 2-deoxy-2-[3R-[8-(4-methoxyphenyl) octanoyloxy]tetradecanoyl]amino-3-O-[8-(4-methoxyphenyl)octanoyl]-4-O-sulfo-6-O-t-butyldimethylsilyl-1,5-anhydro-D-glucitol | Reference Example 4 (u) | Rf 0.21 ($CH_2Cl_2$: $CH_3OH$ = 9:1) |
| 6 (v) | $R^b$: H<br>$R^c$: 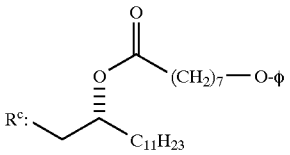 <br>$R^d$: $(CH_2)_7$—O-ϕ | 2-deoxy-2-(3R-(8-phenoxyoctanoyloxy) tetradecanoyl]amino-3-O-(8-phenoxyoctanoyl)-4-O-sulfo-6-O-t-butyldimethylsilyl-1,5-anhydro-D-glucitol | Reference Example 4 (v) | Rf 0.20 ($CH_2Cl_2$: $CH_3OH$ = 9:1) |
| 6 (w) | $R^b$: H<br>$R^c$: 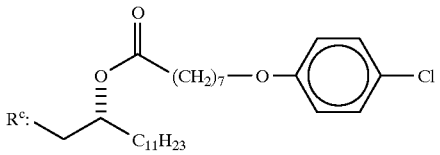 <br>$R^d$: 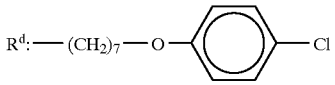 | 2-deoxy-2-[3R-[8-(4-chlorophenoxy)octanoyloxy] tetradecanoyl]amino-3-O-[8-(4-chlorophenoxy) octanoyl]-4-O-sulfo-6-O-t-butyldimethylsilyl-1,5-anhydro-D-glucitol | Reference Example 4 (w) | Rf 0.21 ($CH_2Cl_2$: $CH_3OH$ = 9:1) |

TABLE IX-continued

| No. | $R^b$,$R^c$,$R^d$ | Name - *Pyridine Salts of:* | Starting Material | TLC |
|---|---|---|---|---|
| 6 (x) | $R^b$: — H<br>$R^c$: 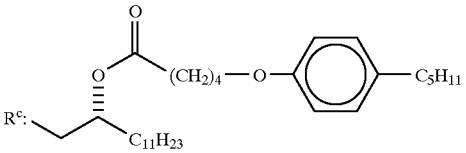 <br>$R^d$: — $(CH_2)_4$ — 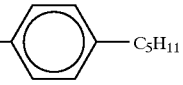 $C_5H_{11}$ | 2-deoxy-2-[3R-[5-(4-pentylphenyl)pentanoyloxy] tetradecanoyl]amino-3-O-[5-(4-pentylphenyl) pentanoyl]-4-O-sulfo-6-O-t-butyldimethylsilyl-1,5-anhydro-D-glucitol | Reference Example 4 (x) | Rf 0.21 ($CH_2Cl_2$: $CH_3OH$ = 9:1) |
| 6 (y) | $R^b$: — H<br>$R^c$: 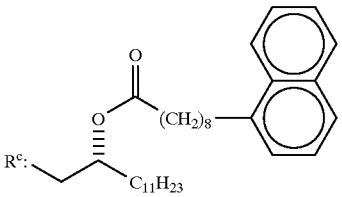 <br>$R^d$: — $(CH_2)_8$ — 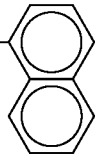 | 2-deoxy-2-[3R-[9-(1-naphthyl)nonanoyloxy] tetradecanoly]amino-3-O-[9-(1-naphthyl) nonanoyl]-4-O-sulfo-6-O-t-butyldimethylsilyl-1,5-anhydro-D-glucitol | Reference Example 4 (y) | Rf 0.21 ($CH_2Cl_2$: $CH_3OH$ = 9:1) |

REFERENCE EXAMPLE 7

Synthesis of 2-deoxy-2-[3S-(9-phenylnonanoyloxy) tetradecanoyl]amino-3-O-(9-phenylnonanoyl)-6-tosyl-1,5-anhydro-D-glucitol

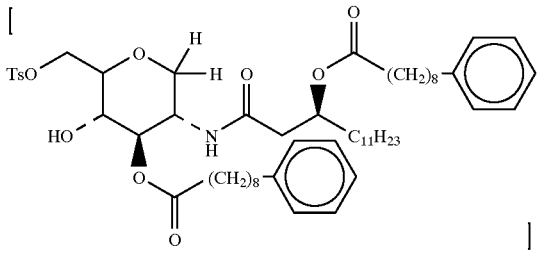

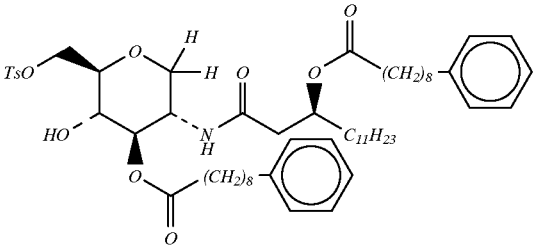

A mixture of the compound (597 mg) prepared in reference example 3(t), tosyl chloride (146 mg) and pyridine (3 ml) was stirred overnight at room temperature. After reaction, toluene was added to the reaction mixture, and the mixture was azeotropically evaporated. To the residue, water and methylene chloride were added. The organic layer separated was washed with an aqueous saturated solution of copper sulfate, water and brine, successively, dried and evaporated. The residue was purified by column chromatography on silica gel (n-$C_6H_{14}$:EtOAc=2:1) to give the title compound (461 mg) having the following physical data.

TLC: Rf 0.49 (n-$C_6H_{14}$:EtOAc32 1:1).

REFERENCE EXAMPLE 8

Synthesis of 2-deoxy-2-[3S-(9-phenylnonanoyloxy) tetradecanoyl]amino-3-O-(9-phenylnonanoyl)-6-deoxy-6-iodo-1,5-anhydro-D-glucitol

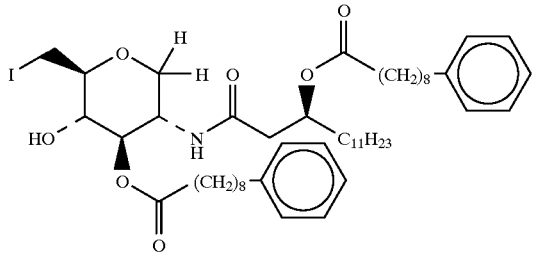

A mixture of the compound (461 mg) prepared in reference example 7, sodium iodide (1.42 g) and acetone (7 ml) was refluxed for 4 hrs. After reaction, to the reaction mixture, water and methylene chloride were added. The organic layer separated was washed, dried and evaporated. The residue was purified by column chromatography on silica gel (n-$C_6H_{14}$:EtOAc=4:1) to give the title compound (232 mg) having the following physical data.

TLC: Rf 0.35 (n-$C_6H_{14}$:EtOAc=2:1);

IR (liquid film): ν 3600~3150, 2920, 2850, 1730, 1650, 1530, 1450, 1370 $cm^{-1}$.

REFERENCE EXAMPLE 9

Synthesis of 2,6-dideoxy-2-[3S-(9-phenylnonanoyloxy)tetradecanoyl]amino-3-O-(9-phenylnonanoyl)-1,5-anhydro-D-glucitol

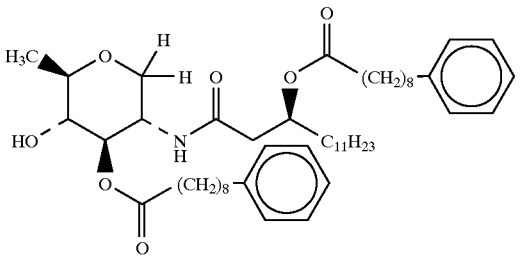

A mixture of the compound (230 mg) prepared in reference example 8, tri-n-butylstanane (133 μl), α,α'-azobisisobutyronitrile (AIBH; a small amount) and toluene (4 ml) was irradiated by high-voltage mercury light for 1.5 hrs with ice-cooling. The reaction mixture was purified by column chromatography on silica gel (n-$C_6H_{14}$:EtOAc=2:1) to give the title compound (215 mg) having the following physical data.

TLC: Rf 0.39 (n-$C_6H_{14}$:EtOAc=6:4).

REFERENCE EXAMPLE 10

Synthesis of benzyl 2-deoxy-2-[9-(1-naphthyl) nonanoyl]amino-3-O-[9-(1-naphthyl)nonanoyl]-4,6-O-isopropylidene-β-D-glucopyranoside

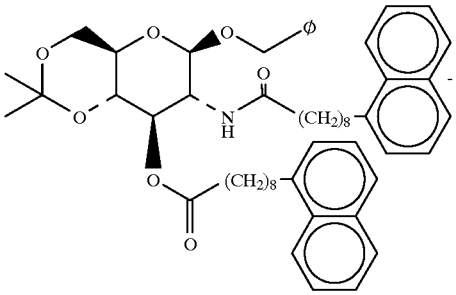

A mixture of benzyl 2-deoxy-2-amino-4,6-O-isopropylidene-β-D-glucopyranoside (248 mg), 9-(1-naphthyl)nonanoic acid (550 mg), 2-chloro-1-methylpyridinium iodide (450 mg), triethylamine (0.34 ml), 4-(N,N-dimethylamino)pyridine (98 mg) and methylene chloride (20 ml) was stirred for 2 hrs at room temperature. To the reaction mixture, brine and ethyl acetate were added. The organic layer separated was dried and purified by column chromatography on silica gel (n-$C_6H_{14}$:EtOAc=4:1) to give the title compound (611 mg) having the following physical data.

TLC: Rf 0.59 (EtOAc:n-$C_6H_{14}$=3:5);

IR (liquid film): ν 3480, 3380, 2920, 2850, 1730, 1650, 1590 $cm^{-1}$.

REFERENCE EXAMPLE 10(a)

Synthesis of benzyl 2-deoxy-2-[9-(2-naphthyl) nonanoyl]amino-3-O-[9-(2-naphthyl)nonanoyl]-4,6-O-isopropylidene-β-D-glucopyranoside

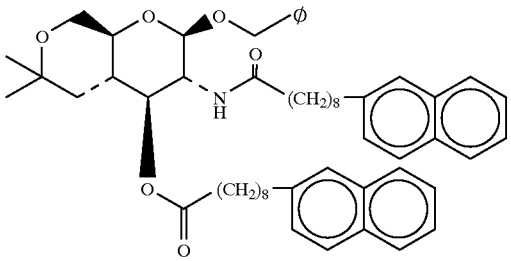

By the same procedure as in reference example 10, using 9-(2-naphthyl)nonanoic acid instead of 9-(1-naphthyl) nonanoic acid, the title compound having the following physical data was prepared:

TLC: Rf 0.80 (EtOAc:n-$C_6H_{14}$=3:5);

IR: ν 3350, 2920, 2840, 1730, 1650, 1520 $cm^{-1}$.

REFERENCE EXAMPLE 11

Synthesis of benzyl 2-deoxy-2-[9-(1-naphthyl) nonanoyl]amino-3-O-[9-(1-naphthyl)nonanoyl]-β-D-glucopyranoside

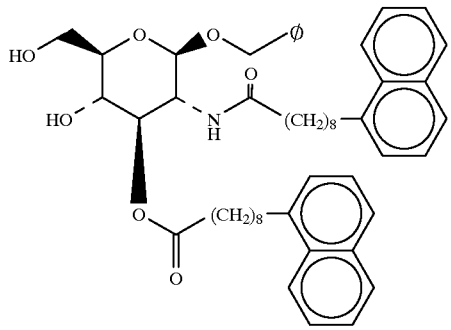

By the same procedure as in reference example 3, using the compound (611 mg) prepared in reference example 10, the title compound having the following physical data was prepared:

TLC: Rf 0.05 (EtOAc:n-$C_6H_{14}$=3:5).

REFERENCE EXAMPLE 11(a)

Synthesis of 2-deoxy-2-[9-(2-naphthyl)nonanoyl] amino-3-O-[9-(2-naphthyl)nonanoyl]-β-D-glucopyranoside

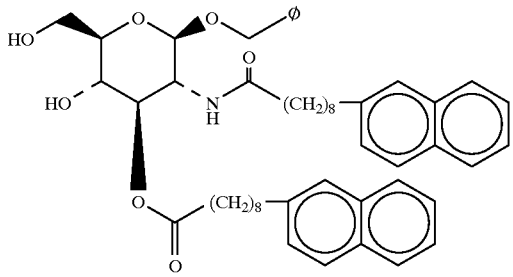

By the same procedure as in reference example 11, using the compound prepared in reference example 10(a), the title compound was prepared:

REFERENCE EXAMPLE 12

Synthesis of benzyl 2-deoxy-2-[9-(1-naphthyl) nonanoyl]amino-3-O-[9-(1-naphthyl)nonanoyl]-6-O-t-butyldimethylsilyl-β-D-glucopyranoside

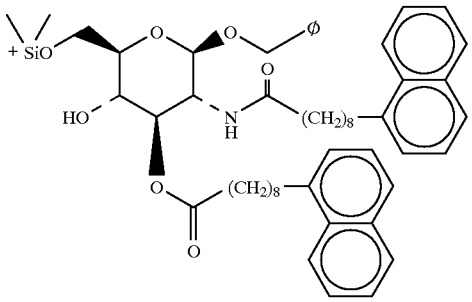

By the same procedure as in reference example 4, using the compound prepared in reference example 11, the title compound (493 mg) having the following physical data was prepared:

TLC: Rf 0.55 (EtOAc:n-$C_6H_{14}$=3:5);

IR: ν 3430, 3250, 3050, 2920, 2850, 1730, 1710, 1640, 1540 $cm^{-1}$.

REFERENCE EXAMPLE 12(a)

Synthesis of benzyl 2-deoxy-2-[9-(2-naphthyl) nonan oyl]amino-3-O-[9-(2-naphthyl)nonanoyl]-6-O-t-butyldimethylsilyl-β-D-glucopyranoside

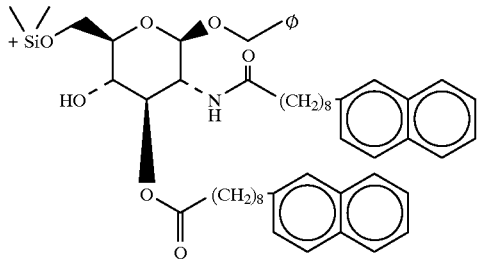

By the same procedure as in reference example 12, using the compound prepared in reference example 11(a), the title compound having the following physical data was prepared:

IR: ν 3450, 2920, 2850, 1730, 1710, 1640, 1540 $cm^{-1}$.

REFERENCE EXAMPLE 13

Synthesis of 2-deoxy-2-[9-(1-naphthyl)nonanoyl] amino-3-O-[9-(1-naphthyl)nonanoyl]-6-O-t-butyldimethylsilyl-D-glucopyranose

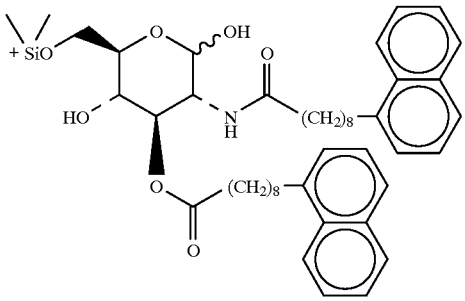

By the same procedure as in reference example 5, using the compound (493 mg) prepared in reference example 12, the title compound having the following physical data was prepared:

TLC: Rf 0.33 (EtOAc:n-$C_6H_{14}$=3:5).

REFERENCE EXAMPLE 13(a)

Synthesis of 2-deoxy-2-[9-(2-naphthyl)nonanoyl] amino-3-O-[9-(2-naphthyl)nonanoyl]-6-O-t-butyldimethylsilyl-D-glucopyranose

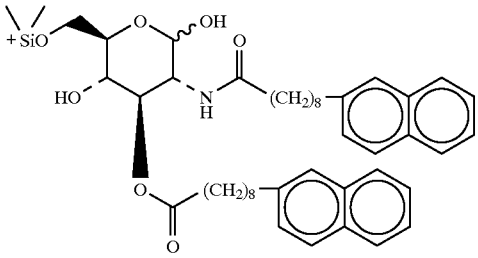

By the same procedure as in reference example 13, using the compound prepared in reference example 12(a), the title compound having the following physical data was prepared:

TLC: Rf 0.59 (EtOAc:n-$C_6H_{14}$=3:5).

REFERENCE EXAMPLE 14

Synthesis of *pyridine salt of* 2-deoxy-2-[9-(1-naphthyl)nonanoyl]amino-3-O-[9-(1-naphthyl) nonanoyl]-4-O-sulfo-6-O-t-butyldimethylsilyl-D-glucopyranose

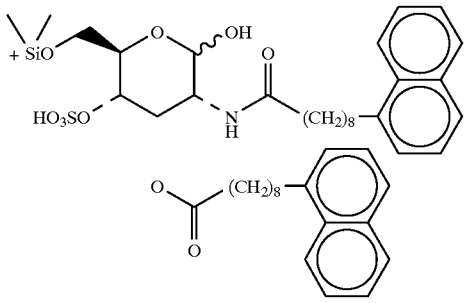

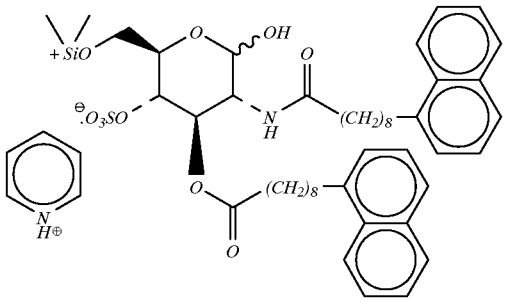

By the same procedure as in reference example 6, using the compound prepared in reference example 13, the title compound was prepared:

REFERENCE EXAMPLE 14(a)

Synthesis of *pyridine salt of* 2-deoxy-2-[9-(2-naphthyl)nonanoyl]amino-3-O-[9-(2-naphthyl)nonanoyl]-4-O-sulfo-6-O-t-butyldimethylsilyl-D-glucopyranose

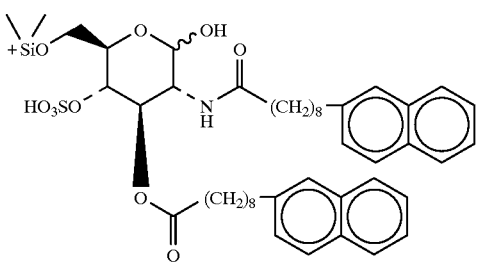

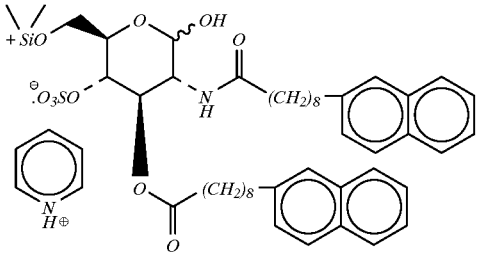

By the same procedure as in reference example 14, using with the compound prepared in reference example 13(a), the title compound having the following physical data was prepared:

TLC: Rf 0.73 ($CH_3OH$:$CH_2Cl_2$=2:9).

EXAMPLE 1

Synthesis of *salt form of* 2-deoxy-2-[3R-(4-phenylbutyryloxy)tetradecanoyl]amino-3-O-(4-phenybutyryl)-4-O-sulfo-D-glucopyranose

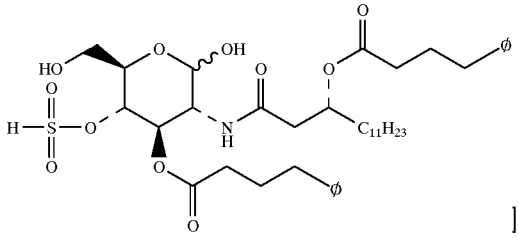

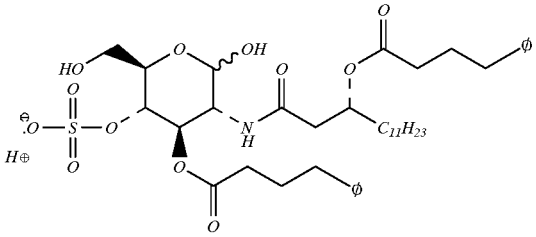

A solution of the compound (550 mg) prepared in reference example 6 dissolved in a mixed solvent of methanol (4 ml) and acetic acid (3 ml) was stirred for 9 hrs at room temperature. The reaction solution was evaporated, and toluene was added to the residue. The solution was evaporated. The residue was purified by column chromatography on silica gel ($CH_2Cl_2$:$CH_3OH$=88:12). To the compound obtained, dry dioxan was added, and the solution was freeze-dried to give the title compound (514 mg) having the following physical data. *The title compound was obtained in the pyridine salt form, but a part of the pyridine salt was converted into a mixture of calcium, sodium and magnesium salts by salt-exchanging with calcium, sodium and magnesium ions which were present in the silica gel as impurities. M⊕ denotes this mixture in this and the following Examples.*

TLC: Rf 0.37 ($CH_2Cl_2$:$CH_3OH$=9:1);

IR: ν 3350, 2920, 2840, 1720, 1640, 1530, 1450, 1240, 1130, 1080, 1000, 820, 740, 700, 580 $cm^{-1}$.

EXAMPLES 1(a)~1(aa)

By the same procedure as in example 1, using the starting materials specified, the following compounds having the physical data shown in Table X were prepared[:]. *The title compounds were obtained in the pyridine salt form, but a part of the pyridine salt in each example was converted into a mixture of calcium, sodium and magnesium salts by salt-exchanging with calcium, sodium and magnesium ions which were present in the silica gel as impurities.*

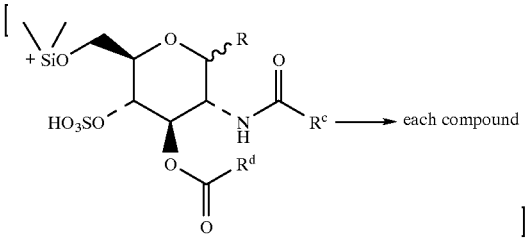

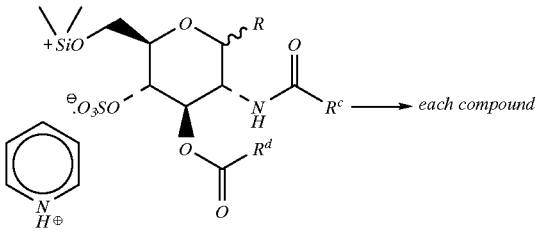

TABLE X
| No. | Structural Formula | Name - *salt form of:* | Starting Material | TLC | IR ($cm^{-1}$) |
|---|---|---|---|---|---|
| [1 (a) | 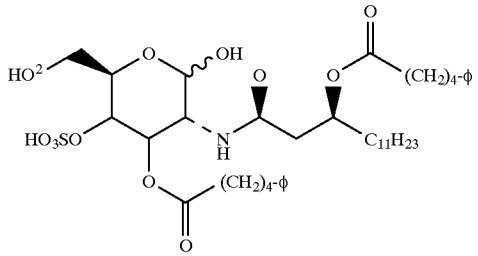 | ] 2-deoxy-2-[3S-(5-phenylpentanoyloxy) tetradocanoyl]amino-3-O-(5-phenylpentanoyl)-4-O-sulfo-D-glucopyranose | Reference Example 6 (a) | Rf 0.27 ($CH_2Cl_2$: $CH_3OH$ = 85:15) | ν3400, 2920, 2850, 1720, 1650, 1520, 1450, 1360, 1240, 1120, 1050, 990, 960, 820, 760, 740, 690, 580 |
| *1 (a)* | 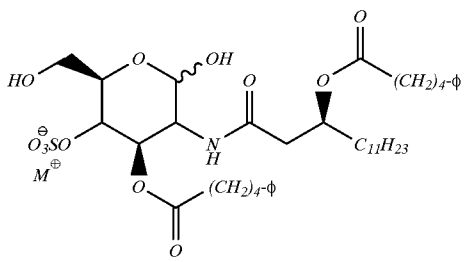 | | | | |
| [1 (b) | 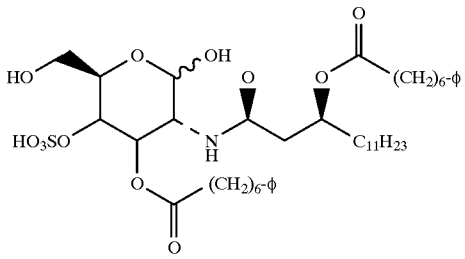 | ] 2-deoxy-2-[3S-(7-phenylheptanoyloxy) tetradocanoyl]amino-3-O-(7-phenylheptanoyl)-4-O-sulfo-D-glucopyranose | Reference Example 6 (b) | Rf 0.27 ($CH_2Cl_2$: $CH_3OH$ = 85:15) | ν3400, 2920, 2850, 1720, 1650, 1520, 1450, 1360, 1240, 1120, 1050, 990, 960, 820, 760, 740, 690, 580 |

TABLE X-continued
| No. | Structural Formula | Name - *salt form of:* | Starting Material | TLC | IR ($cm^{-1}$) |
|---|---|---|---|---|---|
| *1 (b)* | 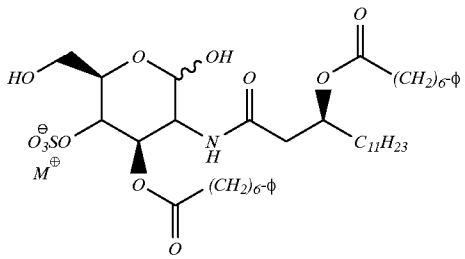 | | | | |
| [1 (c) | 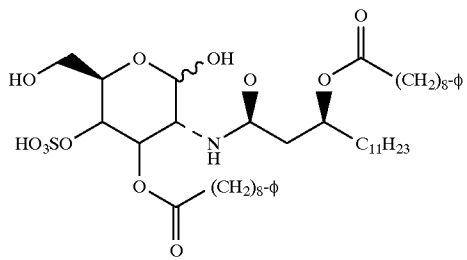 | ] 2-deoxy-2-[3S-(9-phenylnonanoyloxy) tetradecanoyl]amino-3-O-(9-phenylnonanoyl)-4-O-sulfo-D-glucopyranose | Reference Example 6 (c) | Rf 0.35 ($CH_2Cl_2$: $CH_3OH$ = 85:15) | ν3500-3330, 2940, 2855, 1730, 1670, 1460, 1265, 1170, 1120, 1045, 1000 |
| *1 (c)* | 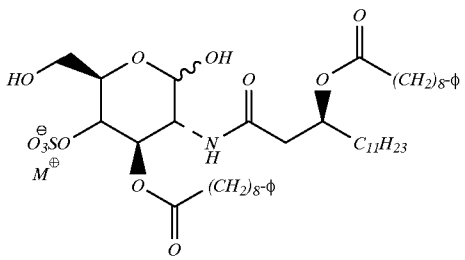 | | | | |

TABLE X-continued
| No. | Structural Formula | Name - *salt form of:* | Starting Material | TLC | IR ($cm^{-1}$) |
|---|---|---|---|---|---|
| [1 (d) | 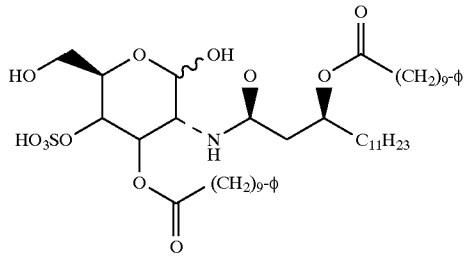 | ] 2-deoxy-2-[3S-(10-phenyldecanoyloxy) tetradecanoyl]amino-3-O-(10-phenyldecanoyl)-4-O-sulfo-D-glucopyranose | Reference Example 6 (d) | Rf 0.17 ($CH_2Cl_2$: $CH_3OH$ = 85:15) | ν3400, 2930, 2850, 1720, 1660, 1540, 1480, 1270, 1170, 1120, 1040, 1000, 820, 690, 590 |
| *1 (d)* | 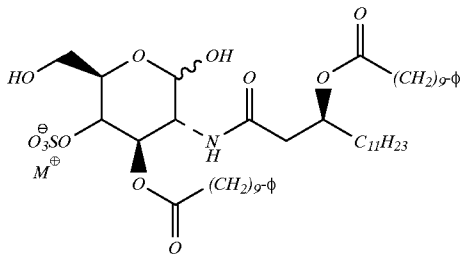 | | | | |
| [1 (e) | 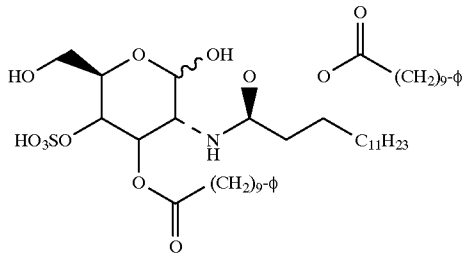 | ] 2-deoxy-2-[3R-(10-phenyldecanoyloxy) tetradecanoyl]amino-3-O-(10-phenyldecanoyl)-4-O-sulfo-D-glucopyranose | Reference Example 6 (e) | Rf 0.17 ($CH_2Cl_2$: $CH_3OH$ = 85:15) | ν3400, 2930, 1720, 1660, 1540, 1480, 1270, 1170, 1120, 1040, 1000, 820, 590 |

TABLE X-continued
| No. | Structural Formula | Name - *salt form of:* | Starting Material | TLC | IR ($cm^{-1}$) |
|---|---|---|---|---|---|
| *1 (e)* | 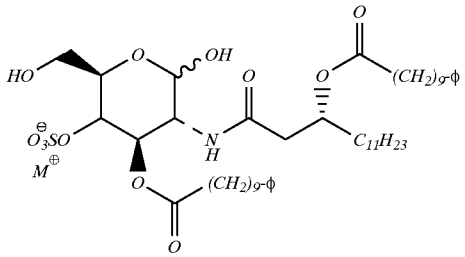 | | | | |
| [1 (f) | 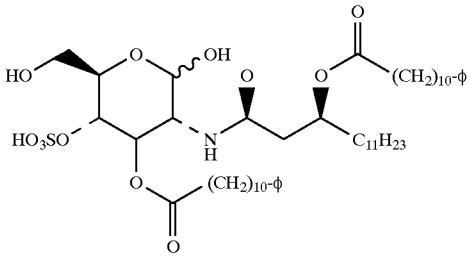 | ] 2-deoxy-2-[3S-(11-phenylundecanoyloxy) tetradecanoyl]amino-3-O-(11-phenylundecanoyl)-4-O-sulfo-D-glucopyranose | Reference Example 6 (f) | Rf 0.35 ($CH_2Cl_2$: $CH_3OH$ = 85:15) | ν3400, 2930, 2840, 1720, 1640, 1530, 1450, 1270, 1220, 1110, 1030, 990, 820, 740, 690 |
| *1 (f)* | 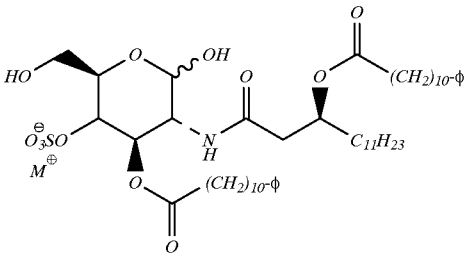 | | | | |

TABLE X-continued

| No. | Structural Formula | Name - *salt form of:* | Starting Material | TLC | IR ($cm^{-1}$) |
|---|---|---|---|---|---|
| [1 (g) | 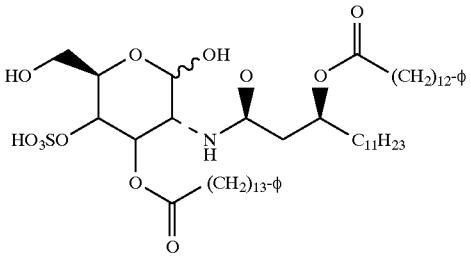 | ] 2-deoxy-2-[3S-(13-phenyltridecanoyloxy) tetradecanoyl]amino-3-O-(13-phenyltridecanoyl)-4-O-sulfo-D-glucopyranose | Reference Example 6 (g) | Rf 0.35 ($CH_2Cl_2$: $CH_3OH$ = 85:15) | ν3400, 2940, 2850, 1720, 1650, 1460, 1270, 1120, 1050, 1000, 820, 700 |
| *1 (g)* | 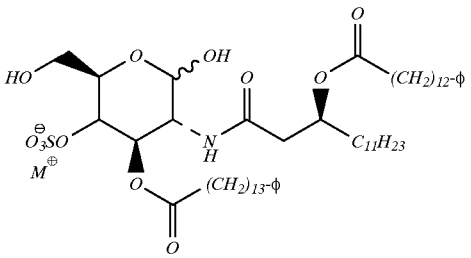 | | | | |
| [1 (h) | 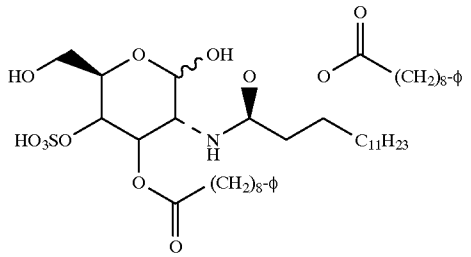 | ] 2-deoxy-2-[3R-(9-phenylnonanoyloxy) tetradecanoyl]amino-3-O-(9-phenylnonanoyl)-4-O-sulfo-D-glucopyranose | Reference Example 6 (h) | Rf 0.45 ($CH_2Cl_2$: $CH_3OH$ = 6:1) | ν3400, 2920, 2850, 1720, 1640, 1540, 1450, 1370, 1250, 1120, 1040, 990 |

TABLE X-continued
| No. | Structural Formula | Name - *salt form of:* | Starting Material | TLC | IR ($cm^{-1}$) |
|---|---|---|---|---|---|
| *1 (h)* | 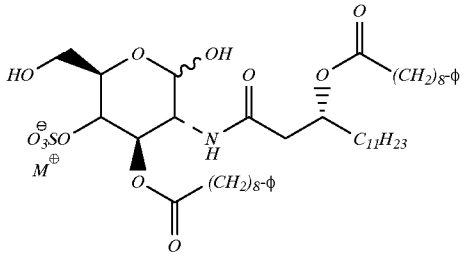 | | | | |
| [1 (i) | 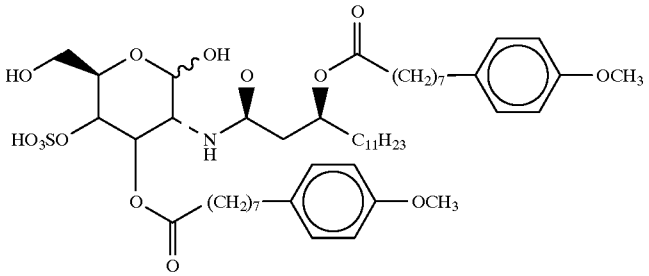 | ] 2-deoxy-2-[3S-[8-(4-methoxyphenyl)octanoyloxy] tetradecanoyl]amino-3-O-[8-(4-methoxyphenyl) octanoyl]-4-O-sulfo-D-glucopyranose | Reference Example 6 (i) | Rf 0.23 (AcOH: $CH_3OH$ = 6:1) | ν3430, 3300, 2910, 2840, 1720, 1640, 1610, 1510, 1450, 1240 |
| *1 (i)* | 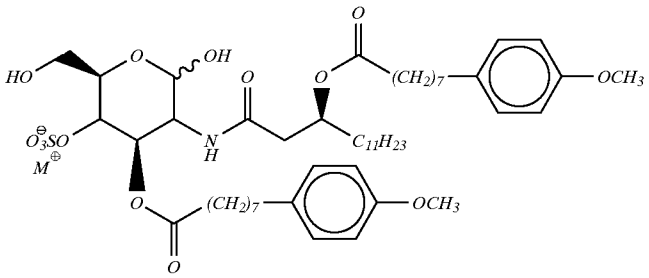 | | | | |

TABLE X-continued

| No. | Structural Formula | Name - *salt form of:* | Starting Material | TLC | IR ($cm^{-1}$) |
|---|---|---|---|---|---|
| [1 (j) | 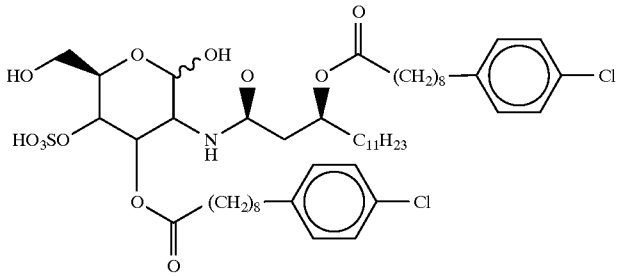 | ] 2-deoxy-2-[3S-[9-(4-chlorophenyl)nonanoyloxy] tetradecanoyl]amino-3-O-[9-(4-chlorophenyl) nonanoyl]-4-O-sulfo-D-glucopyranose | Reference Example 6 (j) | Rf 0.28 ($CH_2Cl_2$: $CH_3OH$ = 6:1) | ν3350, 2930, 2850, 1720, 1650, 1540, 1450 |
| *1 (j)* | 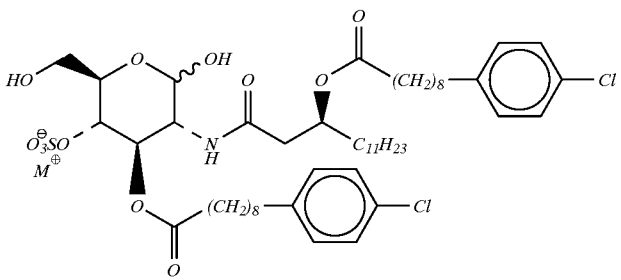 | | | | |
| [1 (k) | 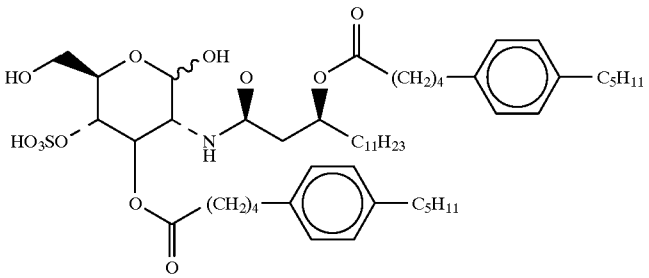 | ] 2-deoxy-2-[3S-[5-(4-pentylphenyl)pentanoyloxy] tetradecanoyl]amino-3-O-[5-(4-pentylphenyl) pentanoyl]-4-O-sulfo-D-glucopyranose | Reference Example 6 (k) | Rf 0.25 ($CH_2Cl_2$: $CH_3OH$ = 6:1) | ν3300, 2920, 2860, 1730, 1650, 1540, 1510, 1450 |

TABLE X-continued
| No. | Structural Formula | Name - *salt form of:* | Starting Material | TLC | IR ($cm^{-1}$) |
|---|---|---|---|---|---|
| *1 (k)* | 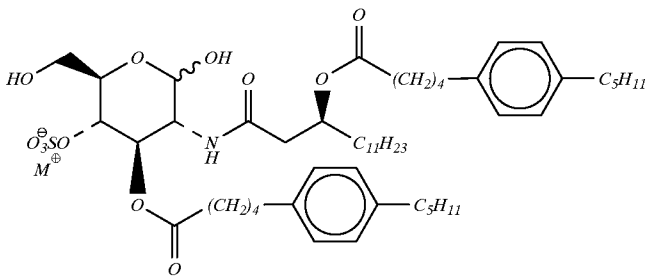 | | | | |
| [1 (l) | 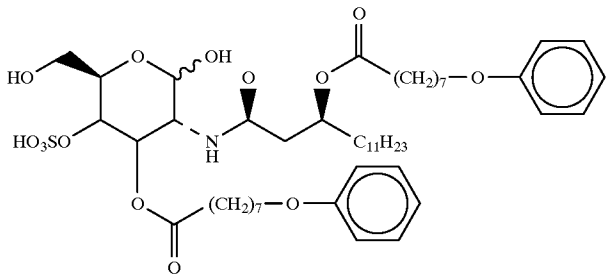 | ] 2-deoxy-2-[3S-(8-phenoxyoctanoyloxy) tetradecanoyl]amino-3-O-(8-phenoxyoctanoyl)-4-O-sulfo-D-glucopyranose | Reference Example 6 (l) | Rf 0.22 ($CH_2Cl_2$: $CH_3OH$ = 6:1) | ν3450, 3320, 2920, 2850, 1720, 1650, 1590, 1490, 1240 |
| *1 (l)* | 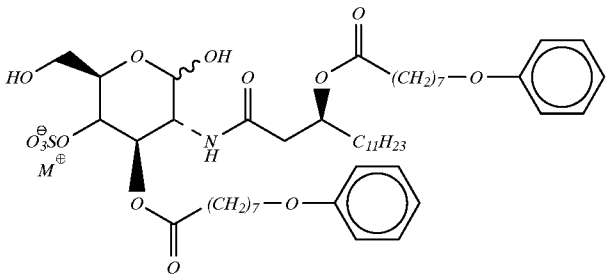 | | | | |

TABLE X-continued

| No. | Structural Formula | Name - *salt form of:* | Starting Material | TLC | IR ($cm^{-1}$) |
|---|---|---|---|---|---|
| [1 (m) | 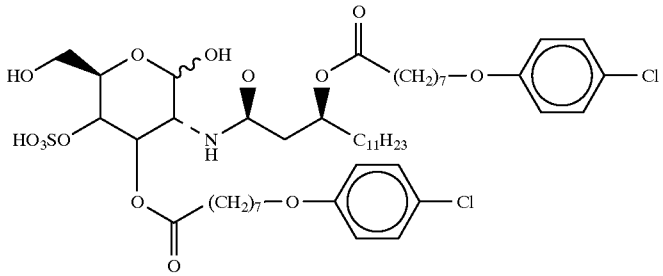 ] | 2-deoxy-2-[3S-[8-(4-chlorophenoxy)octanoyloxy] tetradecanoyl]amino-3-O-[8-(4-chlorophenoxy) octanoyl]-4-O-sulfo-D-glucopyranose | Reference Example 6 (m) | Rf 0.40 ($CH_2Cl_2$: $CH_3OH$ = 6:1) | ν3400, 2920, 2850, 1730, 1650, 1600, 1580, 1530, 1490, 1470, 1390, 1240, 1170, 1110, 1050, 820, 750 |
| *1 (m)* | 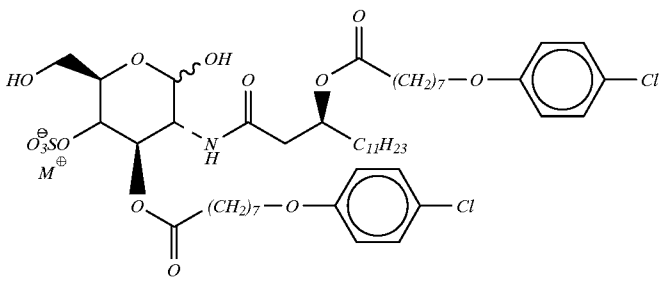 | | | | |
| [1 (n) | 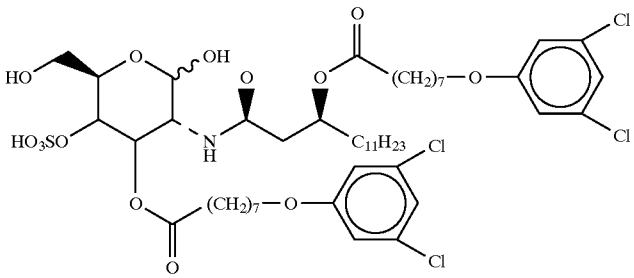 ] | 2-deoxy-2-[3S-[8-(3,5-dichlorophenoxy) octanoyloxy]tetradecanoyl]amino-3-O-[8-(3,5-dichlorophenoxy)octanoyl]-4-O-sulfo-D-glucopyrnaose | Reference Example 6 (n) | Rf 0.28 ($CH_2Cl_2$: $CH_3OH$ = 10.1) | ν3400, 2920, 2850, 1730, 1650, 1590, 1570, 1440, 1420, 1380, 1260, 1220, 1100, 1030, 990, 830, 800 |

TABLE X-continued
| No. | Structural Formula | Name - *salt form of:* | Starting Material | TLC | IR ($cm^{-1}$) |
|---|---|---|---|---|---|
| *1 (n)* | 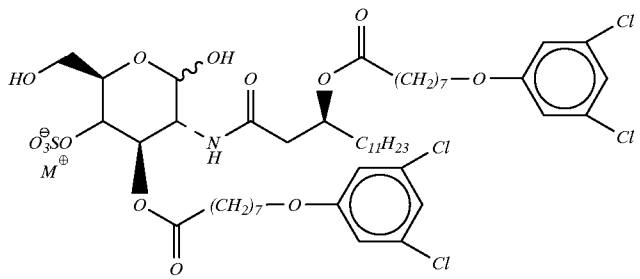 | | | | |
| [1 (o) | 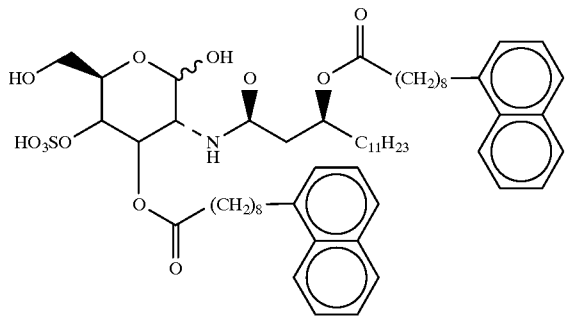 | ] 2-deoxy-2-[3S-[9-(1-naphthyl)nonanoyloxy] tetradecanoyl]amino-3-O-[9-(1-naphthyl) nonanoyl]-4-O-sulfo-D-glucopyranose | Reference Example 6 (o) | Rf 0.20 ($CH_2Cl_2$: $CH_3OH$ = 9:2) | ν3400, 2910, 2840, 1720, 1650, 1530, 1450, 1370, 1230, 1120, 1040, 1000, 920, 770 |
| *1 (o)* | 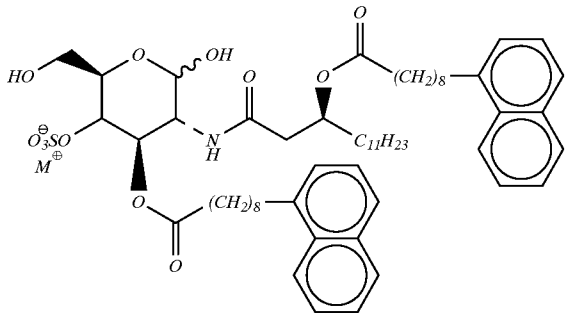 | | | | |

TABLE X-continued

| No. | Structural Formula | Name - *salt form of:* | Starting Material | TLC | IR ($cm^{-1}$) |
|---|---|---|---|---|---|
| [1 (p) | 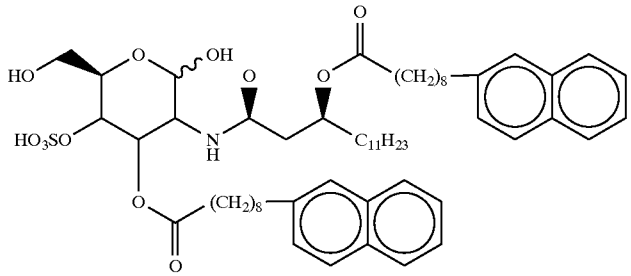 | ] 2-deoxy-2-[3S-[9-(2-naphthyl)nonanoyloxy] tetradecanoyl]amino-3-O-[9-(2-naphthyl) nonanoyl]-4-O-sulfo-D-glucopyranose | Reference Example 6 (p) | Rf 0.31 ($CH_2Cl_2$: $CH_3OH$ = 5:1) | ν3400, 2920, 2850, 1720, 1640, 1540, 1450, 1230, 1110 |
| *1 (p)* | 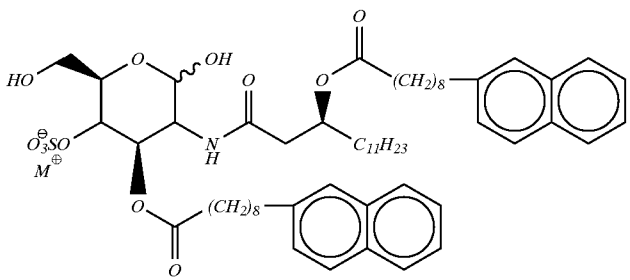 | | | | |
| [1 (q) | 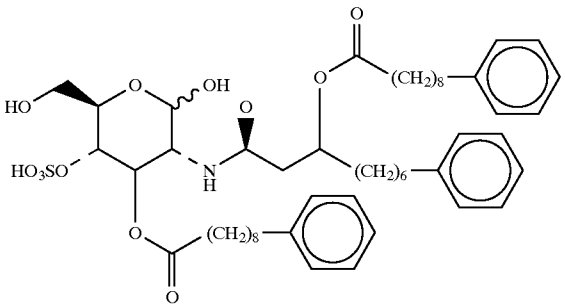 | ] 2-deoxy-2-[3R-(9-phenylnonanoyloxy)-9-phenylnonanoyl]amino-3-O-(9-phenylnonanoyl)-4-O-sulfo-D-glucopyranose | Reference Example 6 (q) | Rf 0.10 ($CH_2Cl_2$: $CH_3OH$ = 9:1) | ν3400, 2920, 2840, 1720, 1650, 1530, 1450 |

TABLE X-continued
| No. | Structural Formula | Name - *salt form of:* | Starting Material | TLC | IR ($cm^{-1}$) |
|---|---|---|---|---|---|
| *1 (q)* | 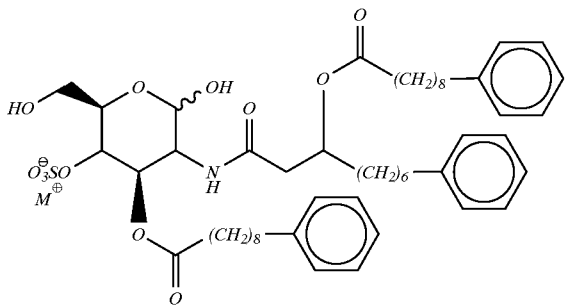 | | | | |
| [1 (r) | 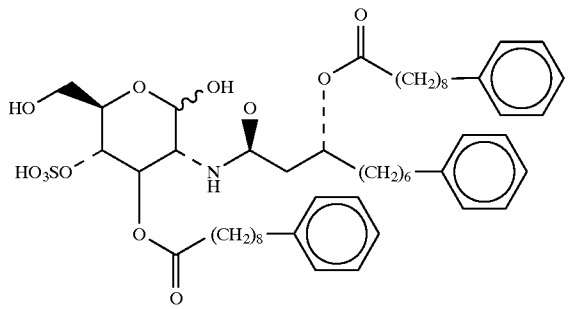 | ] 2-deoxy-2-[3S-(9-phenylnonanoyloxy)-9-phenylnonanoyl]amino-3-O-(9-phenylnonanoyl)-4-O-sulfo-D-glucopyranose | Reference Example 6 (r) | Rf 0.10 ($CH_2Cl_2$: $CH_3OH$ = 9:1) | ν3400, 3340, 2920, 2850, 1720, 1650, 1540, 1440, 1210, 1140, 980, 690 |
| *1 (r)* | 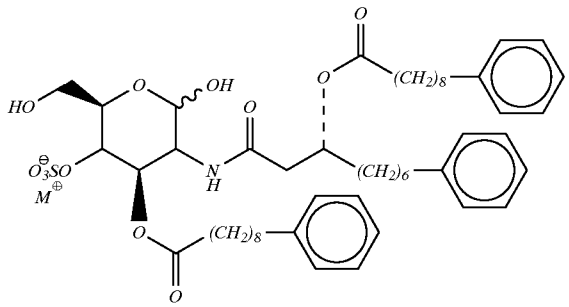 | | | | |

TABLE X-continued

| No. | Structural Formula | Name - *salt form of:* | Starting Material | TLC | IR ($cm^{-1}$) |
|---|---|---|---|---|---|
| [1 (s) | 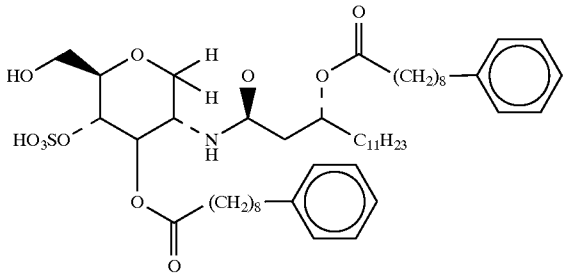 | ] 2-deoxy-2-[3R-(9-phenylnonanoyloxy) tetradecanoyl]amino-3-O-(9-phenylnonanoyl)-4-O-sulfo-1,5-anhydro-D-glucitol | Reference Example 6 (s) | Rf 0.35 ($CH_2Cl_2$: $CH_3OH$ = 5:1) | ν3430, 2930, 2850, 1730, 1660, 1555, 1460, 1245 |
| *1 (s)* | 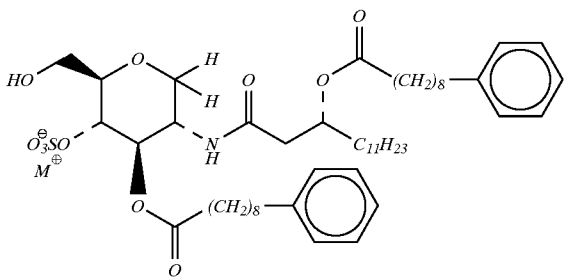 | | | | |
| [1 (t) | 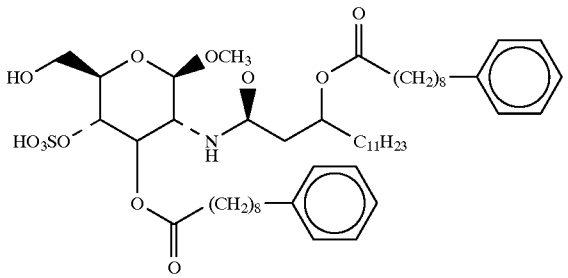 | ] 2-methyl-2-deoxy-2-[3R-(9-phenylnonanoyloxy) tetradecanoyl]amino-3-O-(9-phenylnonanoyl)-4-O-sulfo-β-D-glucopyranoside | Reference Example 6 (t) | Rf 0.30 ($CH_2Cl_2$: $CH_3OH$ = 6:1) | ν3450, 2925, 2850, 1735, 1650, 1540, 1460, 1380, 1240, 1040, 995 |

TABLE X-continued
| No. | Structural Formula | Name - *salt form of:* | Starting Material | TLC | IR ($cm^{-1}$) |
|---|---|---|---|---|---|
| *1 (t)* | 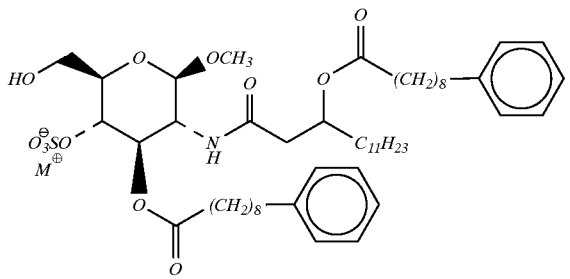 | | | | |
| [1 (u) | 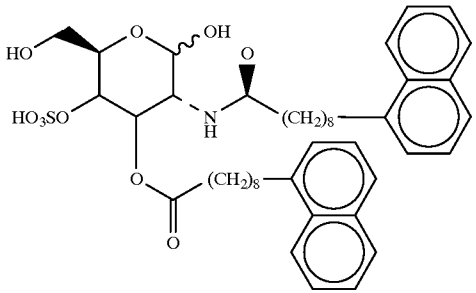 | ] 2-deoxy-2-[9-(1-naphthyl)nonanoyl]amino-3-O-[9-(1-naphthyl)nonanoyl]-4-O-sulfo-D-glucopyranose | Reference Example 14 | Rf 0.19 ($CH_3OH$: $CH_2Cl_2$ = 2:9) | ν3400, 2940, 2860, 1730, 1660, 1530, 1260, 1010 |
| *1 (u)* | 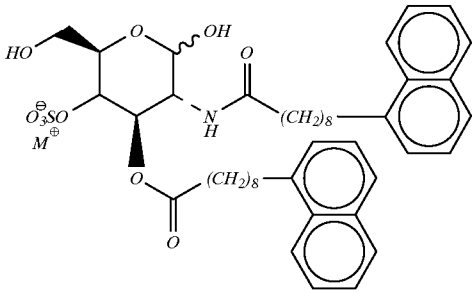 | | | | |

TABLE X-continued
| No. | Structural Formula | Name - *salt form of:* | Starting Material | TLC | IR ($cm^{-1}$) |
|---|---|---|---|---|---|
| [1 (v) | 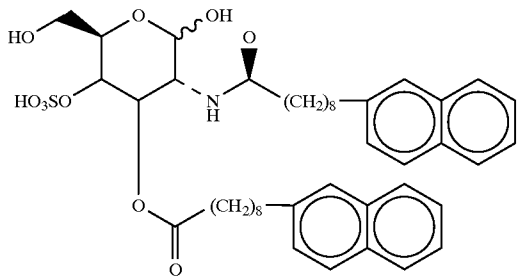 | ] 2-deoxy-2-[9-(2-naphthyl)nonanoyl]amino-3-O-[9-(2-naphthyl)nonanoyl]-4-O-sulfo-D-glucopyranose | Reference Example 14 (a) | Rf 0.34 ($CH_3OH$: $CH_2Cl_2$ = 1:10) | ν3450, 3350, 2910, 2850, 1720, 1650, 1630, 1540, 1450 |
| *1 (v)* | 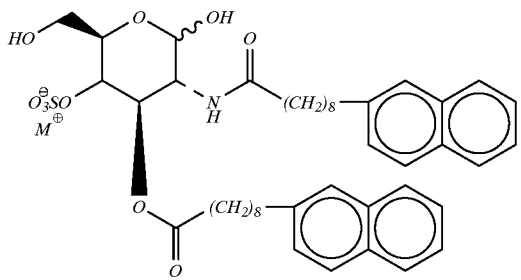 | | | | |
| [1 (w) | 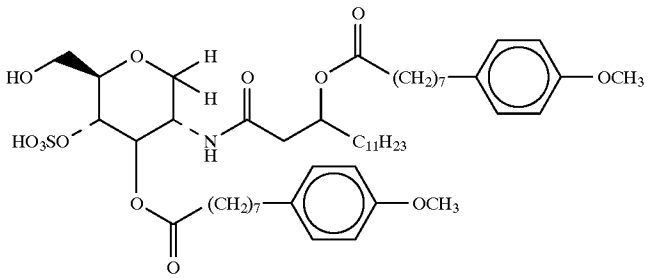 | ] 2-deoxy-2-[3R-[8-(4-methoxyphenyl)octanoyloxy]tetradecanoyl]amino-3-O-[8-(1-methoxyphenyl)octanoyl]-4-O-sulfo-1,5-anhydro-D-glucitol | Reference Example 6 (u) | Rf 0.34 ($CH_2Cl_2$: $CH_3OH$ = 5:1) | ν3430, 1730, 1660, 1550 |

TABLE X-continued
| No. | Structural Formula | Name - *salt form of:* | Starting Material | TLC | IR ($cm^{-1}$) |
|---|---|---|---|---|---|
| *1 (w)* | 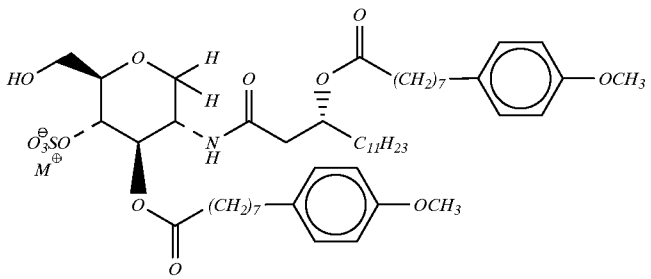 | | | | |
| [1 (x) | 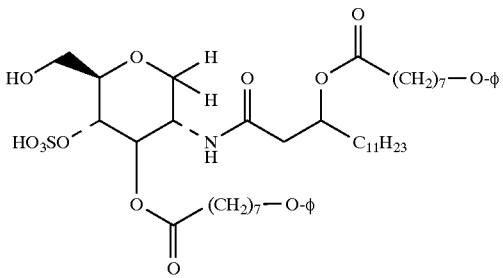 | ] 2-deoxy-2-[3R-(8-phenoxyoctanoyloxy) tetraecanoyl]amino-3-O-(8-phenoxyoctanoyl)-4-O-sulfo-1,5-anhydro-D-glucitol | Reference Example 6 (v) | Rf 0.30 ($CH_2Cl_2$: $CH_3OH$ = 5:1) | ν3510, 1728, 1650, 1600, 1538 |
| *1 (x)* | 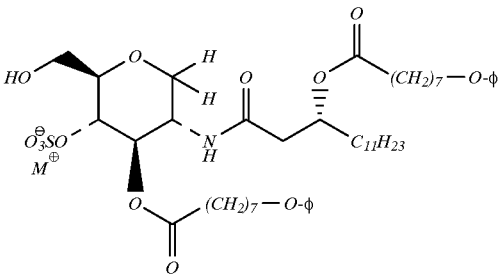 | | | | |

TABLE X-continued

| No. | Structural Formula | Name - *salt form of:* | Starting Material | TLC | IR ($cm^{-1}$) |
|---|---|---|---|---|---|
| [1 (y) | 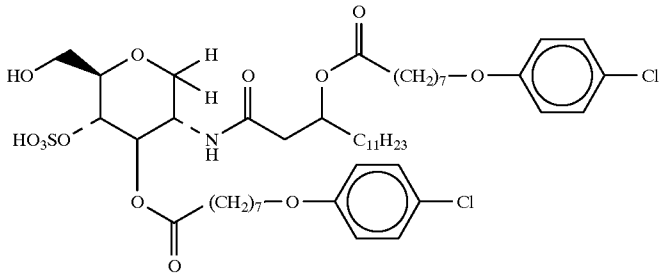 ] | 2-deoxy-2[3R-[8-(4-chlorophenoxy)octanoyloxy] tetradecanoyl]amino-3-O-[8-(4-chlorophenoxy) octanoyl]-4-O-sulfo-1,5-anhydro-D-glucitol | Reference Example 6 (w) | Rf 0.29 ($CH_2Cl_2$: $CH_2OH$ = 5:1) | ν3510, 1730, 1651, 1600, 1540 |
| *1 (y)* | 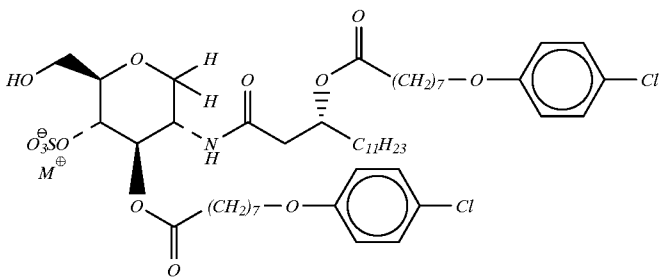 | | | | |
| [1 (z) | 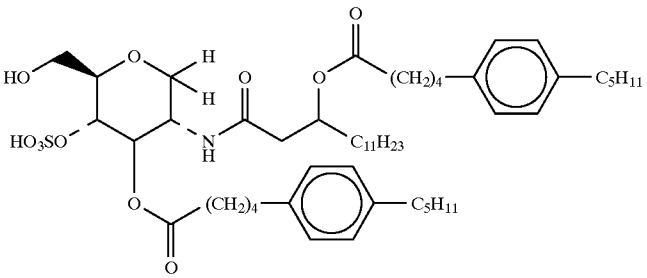 ] | 2-deoxy-2-[3R-[5-(4-pentylphenyl)pentanoyloxy] tetradecanoyl]amino-3-O-[5-(4-pentylphenyl) pentanoyl]-4-O-sulfo-1,5-anhydro-D-glucitol | Reference Example 6 (a) | Rf 0.30 ($CH_2Cl_2$: $CH_3OH$ = 5:1) | ν3520, 1730, 1645, 1600, 1540 |

TABLE X-continued
| No. | Structural Formula | Name - *salt form of:* | Starting Material | TLC | IR ($cm^{-1}$) |
|---|---|---|---|---|---|
| *1 (z)* | 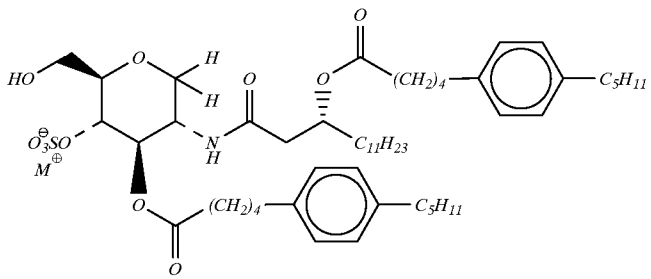 | | | | |
| [1 (aa) | 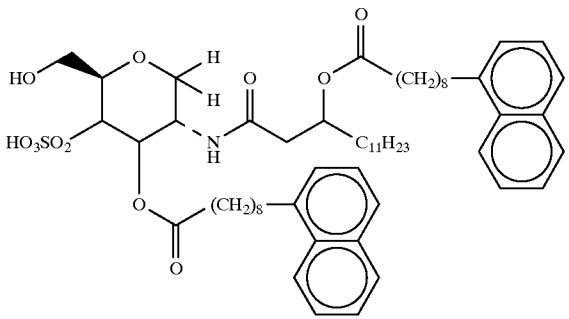 | ] 2-deoxy-2-[3R-[9-(1-naphthyl)nonanoyloxy] tetradecanoyl]amino-3-O-[9-(1-naphthyl) nonanoyl]-4-O-sulfo-1,5-anhydro-D-glucitol | Reference Example 6 (y) | Rf 0.29 ($CH_2Cl_2$: $CH_3OH$ = 5:1) | ν3380, 1725, 1653, 1539, 780 |
| *1 (aa)* | 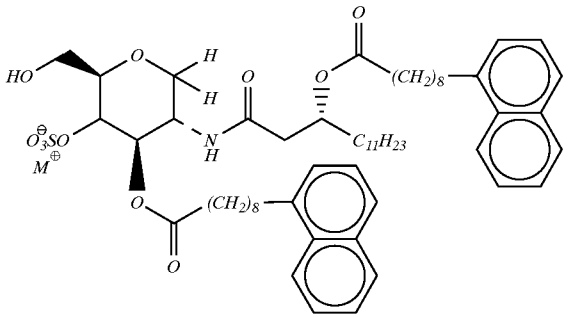 | | | | |

EXAMPLE 2

Synthesis of *salt form of* 2,6-deoxy-2-[3S-(9-phenylnonanoyloxy)tetradecanoyl]amino-3-O-(9-phenynonanoyl)-4-O-sulfo-1,5-anhydro-D-glucitol

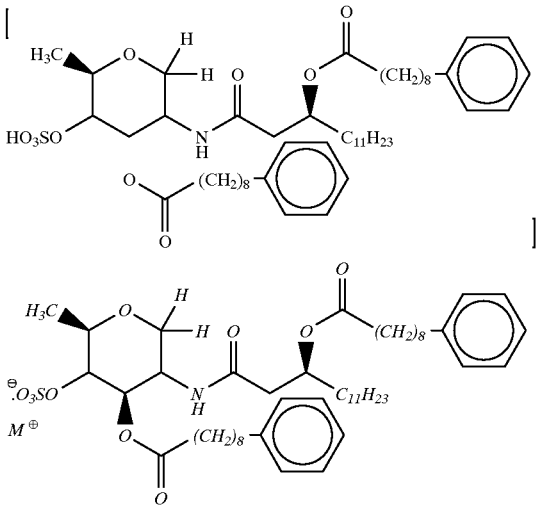

A mixture of the compound (213 mg) prepared in reference example 9, sulfur trioxide-pyridine complex (126 mg) and pyridine (2 ml) was stirred for 2.5 hrs at room temperature. After reaction, toluene and ethanol were added to the reaction mixture and the mixture was evaporated azeotropically. The solution was evaporated. The residue was purified by column chromatography on silica gel ($CH_2Cl_2$:$CH_3OH$=15:1). To the compound obtained, dry dioxan was added, and the solution was freeze-dried to give the title compound (180 mg) having the following physical data[:]. *The title compound was obtained in the pyridine salt form, but a part of the pyridine salt was converted into a mixture of calcium, sodium and magnesium salts by salt-exchanging with calcium, sodium and magnesium ions which were present in the silica gel as impurities.*

TLC: Rf 0.25 ($CH_2Cl_2$:$CH_3OH$=7:1);

IR: ν 3430, 2930, 2850, 1710, 1650, 1565, 1450, 1265–1225, 1065, 995 $cm^{-1}$.

REFERENCE EXAMPLE 15

Synthesis of 2-deoxy-2-(3-hydroxytetradecanoyl) amino-4-O-benzyl-1,5-anhydro-D-xylitol

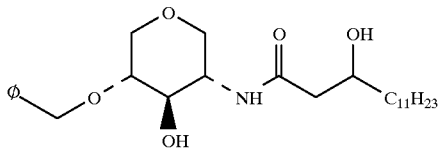

A solution of ethyl acetate of 2,2'-dipyridyldisulfide (2.54 g) was added slowly a the suspension of 2-deoxy-2-amino-4-O-benzyl-1,5-anhydro-D-xylitol (1.07 g), triphenylphosphine (3.02 g) and 3-hydroxymiristic acid (1.23 g).

The mixture was stirred for 5 hours at room temperature, and then the reaction solution was washed with successively, water, 1N aqueous solution of sodium hydroxide and a saturated aqueous solution of sodium chloride, and dried and evaporated.

The residue was purified by column chromatography on silica gel ($CH_2Cl_2$:AcOEt=1:1) to give the title compound (1.74 g) having the following physical data:

TLC: Rf 0.33 ($CH_2Cl_2$:MeOH=1:20);

IR: ν 3400, 3280, 2900, 2840, 1730, 1650, 1460 $cm^{-1}$.

REFERENCE EXAMPLES 15(a)~15(b)

By the same procedure as in reference example 15, following compounds having the physical data shown in Table XI were prepared:

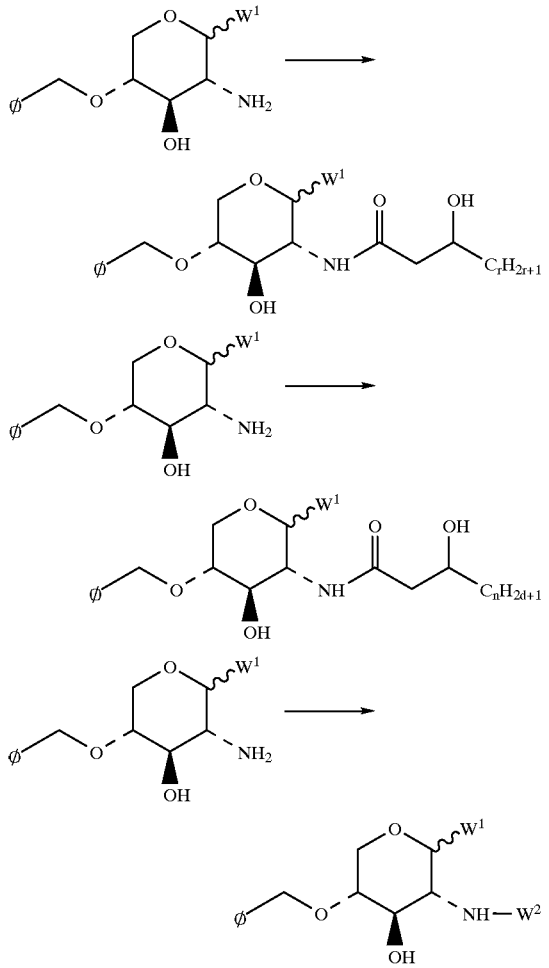

TABLE XI

| No. | $W^1$,$W^2$ | Name | TLC | IR ($cm^{-1}$) |
|---|---|---|---|---|
| 15 (a) | $W^1$: — H<br>$W^2$: 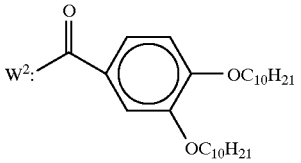 | 2-deoxy-2-(3,4-didecyloxybenzoyl) amino-4-O-benzyl-1,5-anhydro-D-xylitol | 0.42 (AcOEt: n-hexane 1:1) | ν 3400, 3260, 2910, 2840, 1615, 1595, 1575, 1500, 1455, 1260, 1215, 1090 |
| 15 (b) | $W^1$: - - $OCH_3$<br>$W^1$: 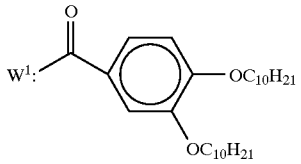 | Methyl 2-deoxy-2-(3,4-didecyloxy benzoyl)amino-4-O-benzyl-1,5-anhydro-α-D-xyloside | | |

REFERENCE EXAMPLE 16

Synthesis of 2-deoxy-2-[3-(9-phenylnonanoyl) oxytetradecanoyl]amino-3-O-(9-phenylnonanoyl)-4-O-benzyl-1,5-anhydro-D-xylitol

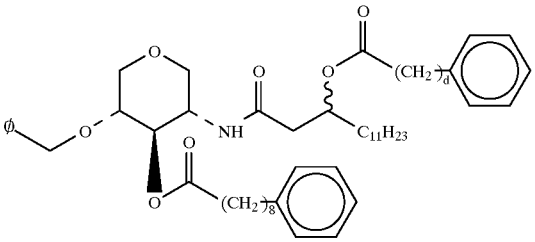

Triethylamine (0.47 ml) was added to a suspension of the compound (500 mg) prepared in reference example 15, phenylnonanoic acid (635 mg) and 2-chloro-1-methyl-pyridiniumiodide (710 mg) in methylene chloride (15 ml), and further 4-(N,N'-dimethylamino)pyridine (135 mg) was added thereto, and the mixture was reacted overnight at room temperature.

The reaction solution was diluted with ethylacetate, washed with successively, water, 1N aqueous solution of sodium hydroxide and a saturated aqueous solution of sodium chloride, dried and evaporated. The residue was purified by column chromatography on silica gel (n-hexane:AcOEt=1:1), and further twice purification using column chromatography on the same condition was carried out to give the title compound (more polar: 261 mg) having the following physical data.

TLC: Rf 0.26 (AcOEt:n-hexane=1:2).

REFERENCE EXAMPLES 16(a)~16(f)

By the same procedure as in reference example 16, using the starting material specified, the following compounds having the physical data shown in Tables XIIa and XIIb were prepared.

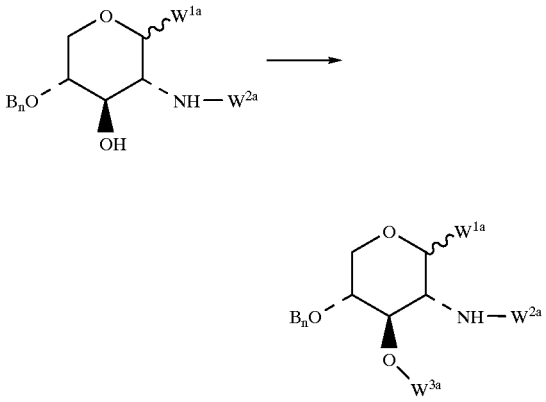

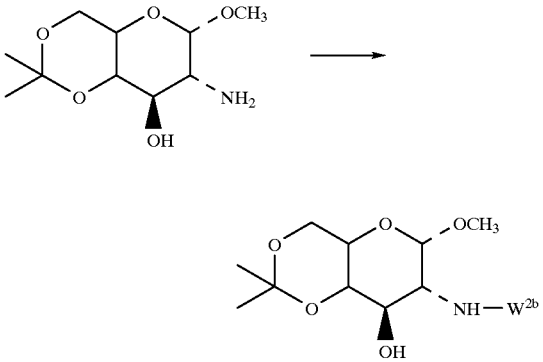

TABLE XIIa

| No. | $W^{1a}$, $W^{2a}$, $W^{3a}$ | Name | Starting material | TLC | IR ($cm^{-1}$) |
|---|---|---|---|---|---|
| 16 (a) | $W^{1a}$: —H<br>$W^{2a}$: 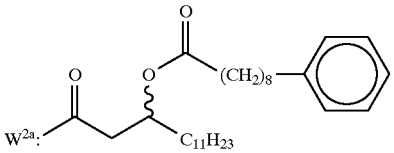 <br>$W^{3a}$: 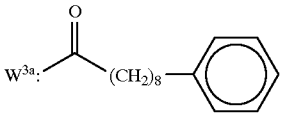 | 2-deoxy-2-[3-(9-phenylnonanoyl)oxytetra-decanoyl]amino-3-O-(9-phenylnonanoyl)-4-O-benzyl-1,5-anhydro-D-xylitol (less polar) | reference example 15 | 0.36 (AcOEt: n-hexane = 1:2) | |
| 16 (b) | $W^{1a}$: —H<br>$W^{2a}$: 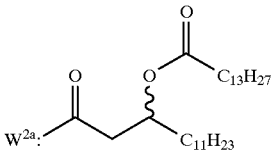 <br>$W^{3a}$: 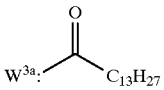 | 2-deoxy-2-[3-tetradecanoyloxytetra-decanoyl]amino-3-O-tetradecanoly-4-O-benzyl-1,5-anhydro-D-xylitol (less polar) | reference example 15 | 0.69 (AcOEt: n-hexane = 3:5) | ν 3290, 2900, 2820, 1720, 1650, 1520 |
| 16 (c) | $W^{1a}$: —H<br>$W^{2a}$: 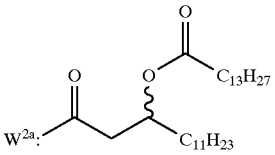 <br>$W^{3a}$: 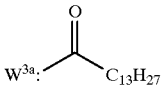 | 2-deoxy-3-(3-tetradecanoyloxytetra-decanol]amino-3-O-tetradecanoly-4-O-benzyl-1,5-anhydro-D-xylitol (more polar) | reference example 15 | 0.65 (AcOEt: n-hexane = 3:5) | ν 3380, 2900, 2830, 7720, 1710, 1640, 1540 |
| 16 (d) | $W^{1a}$: —H<br>$W^{2a}$: 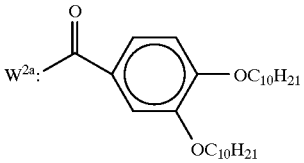 <br>$W^{3a}$: 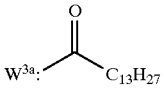 | 2-deoxy-2-(3,4-didecyloxybenzoyl) amino-3-O-tetra-decanoyl-4-O-benzyl-1,5-anhydro-D-xylitol | reference example 15 (a) | 0.63 (AcOEt: n-hexane:chloro-form = 1:4:1) | ν 3350, 2900, 2840, 1720, 1625, 1535, 1505, 1455, 1340, 1270, 1215 |

TABLE XIIa-continued

| No. | $W^{1a}$, $W^{2a}$, $W^{3a}$ | Name | Starting material | TLC | IR ($cm^{-1}$) |
|---|---|---|---|---|---|
| 16 (e) | $W^{1a}$: – –$OCH_3$<br>$W^{2a}$: 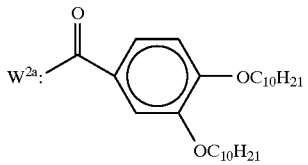 <br>$W^{3a}$: 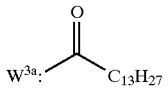 | Methyl 2-deoxy-2-(3,4-didecyloxybenzoyl) amino-3-O-tetra-decanoyl-4-O-benzyl-1,5-anhydro-α-D-xyloside | reference example 15 (b) | | |

TABLE XIIb

| No. | $W^{2b}$ | Name | TLC | IR ($cm^{-1}$) |
|---|---|---|---|---|
| 16 (f) | $W^{2b}$: 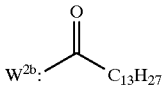 | methyl 2-deoxy-2-tertradecanoyl-4,6-O-isopropilydene-α-D-glucopyranoside | 0.75 ($MeOH:CH_2Cl_2$ = 3:20) | ν 3450, 3320, 2920, 2850, 1640, 1530, 1460 |

REFERENCE EXAMPLE 17

Synthesis of benzyl 2-deoxy-2-(3,4-didecyloxybenzoyl)amino-4,6-O-isopropylidene-β-D-glucopyranoside

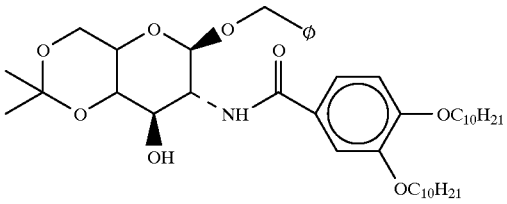

α,α'-dipyridyl disulfide (330 mg) was added to a solution of benzyl 2-deoxy-2-amino-4,6-O-isopropylidene-β-D-glucopyranoside (the compound described in Agric. Biol. Chem., 48(1), 251 (1984); 309 mg), (3,4-didecyloxy) carboxylic acid (521 mg) and triphenylphosphine (393 mg) in ethyl acetate (10 ml), and stirred for 2 hours at room temperature, and further stirred for 2 hours at 50° C. After the reaction, the solution was stirred overnight at room temperature, 4-(N,N-dimethylamino)pyridine (244 mg) was added thereto, and the mixture was stirred for 5 hours at room temperature.

The reaction mixture was diluted with a mixture of hexaneethyl acetate (n-hexane:EtOAc=1:1; 50 ml), and washed with successively, 1N aqueous solution of sodium hydroxide, water, 1N-hydrochloric acid, water and a saturated aqueous solution of sodium chloride, and then dried and evaporated.

The residue was purified by column chromatography on silica gel ($CH_2Cl_2$:EtOAc=7:3) to give the title compounds (612 mg) having the following physical data:

TLC: Rf 0.63 (EtOAc);

IR: ν3520, 3350, 2940, 2860, 1640, 1600, 1592, 1530, 1510, 1475, 1263, 1220, 1113, 1090, 1036, 1010, 853, 804, 758, 728, 690 $cm^{-1}$.

REFERENCE EXAMPLE 17(a)

Synthesis of benzyl 2-deoxy-2-tetradecanoylamino-4,6-O-isopropylidene-β-D-glucopyranoside

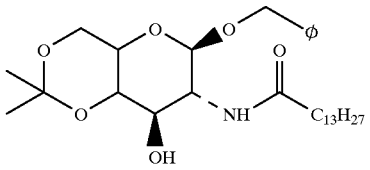

By the same procedure as in reference example 17, the title compound (510 mg) having the following physical data was obtained using the same starting material:

TLC: Rf 0.45 (AcOEt:n-hexane=3:1);

IR: ν3500, 3275, 2400, 2340, 1635, 1540, 1460, 1370, 1265, 1195, 1080 $cm^{-1}$.

REFERENCE EXAMPLE 17(b)

Synthesis of benzyl 2-deoxy-2-[3-(3,4-dioctyloxy) phenylpropionyl]amino-4,6-O-isopropylidene-β-D-glucopyranoside

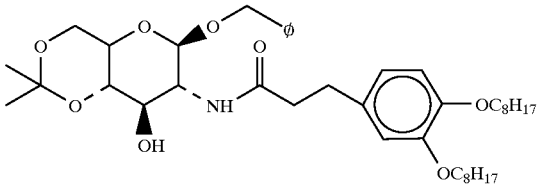

By the same procedure as in reference example 17, the title compound (1.21 g) having the following physical data was obtained using the same starting material:

TLC: Rf 0.67 (AcOEt:n-hexane=3:1);

IR: ν3950, 2910, 2895, 1665, 1585, 1530, 1510, 1260, 1090 $cm^{-1}$.

REFERENCE EXAMPLE 18

Synthesis of methyl 2-deoxy-2-(3,4-didecyloxybenzoyl)amino-4,6-O-isopropylidene-α-D-glucopyranoside

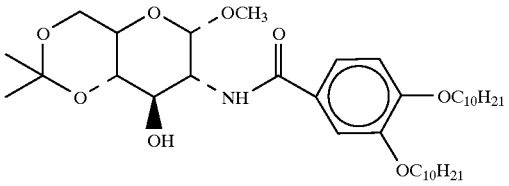

Methyl 2-deoxy-2-amino-4,6-O-isopropylidene-β-D-glucopyranoside (0.5 g), 3,4-di(decyloxy)carboxylic acid (1.21 g) and 1-methyl-2-chloropyridinium iodide (0.93 g) were suspended in methylene chloride, and triethylamine (0.68 ml) was added at room temperature and the mixture reacted overnight.

The reaction solution was diluted with methylene chloride, and then was washed with successively a saturated aqueous solution of sodium bicarbonate and a saturated aqueous solution of sodium chloride, dried and evaporated.

The residue was purified by column chromatography on silica gel ($CH_2Cl_2$:n-hexane:AcOEt=1:1:4) to give the title compound (1.0 g) having the following physical data:

TLC: Rf 0.18 (AcOEt:n-hexane=1:2).

REFERENCE EXAMPLE 18(a)

Synthesis of methyl 2-deoxy-2-[3-(3,4-dioctyloxyphenyl)propenyl]amino-4,6-O-isopropylidene-α-D-glucopyranoside

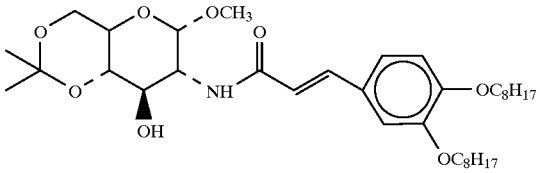

By the same procedure as in reference example 18, the title compound having the following data was obtained using the same starting material.

TLC: Rf 0.75 ($CH_2Cl_2$:MeOH=9:1);

IR: ν3350, 3280, 2920, 2850, 1650, 1610, 1600, 1510 $cm^{-1}$.

REFERENCE EXAMPLE 19

Synthesis of benzyl 2-deoxy-2-(3,4-didecyloxybenzoyl)amino-3-O-(3,4-didecycloxybenzoyl)-4,6-O-isopropylidene-β-D-glucopyranoside

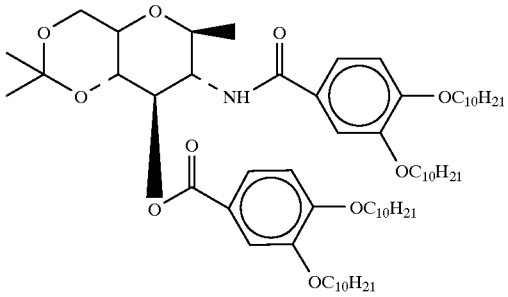

Benzyl 2-deoxy-2-amino-4,6-O-isopropylidene-β-D-glucopyranoside was used as starting material, and the title compound (290 mg) having the following physical data was obtained by the same procedure as in reference example 16.

TLC: Rf 0.8 (AcOEt:n-hexane=3:5);

IR: ν3270, 2930, 2850, 1720, 1640, 1600, 1540, 1510, 1460 $cm^{-1}$.

REFERENCE EXAMPLES 19(a)~19(c)

By the same procedure as in reference example 16, the following compounds having the physical data shown in Table XIII were prepared:

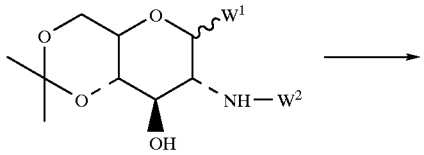

-continued

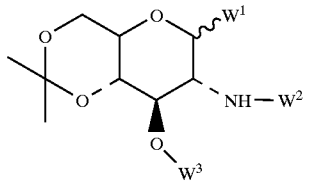

The reaction solution was washed with successively, 1N-hydrochloric acid and water, dried and evaporated to give the title compound having the following physical data.

TLC: Rf 0.64 ($CH_2Cl_2$:EtOAc=10:1).

REFERENCE EXAMPLES 20(a)~20(d)

By the same procedure as in reference example 20, using the starting material specified, the following compounds having the physical data shown in Table XIV were prepared:

TABLE XIII

| No. | $W^1$,$W^2$,$W^3$ | Name | Starting material | TLC | IR ($cm^{-1}$) |
|---|---|---|---|---|---|
| 19 (a) | $W^1$: – –$OCH_3$ 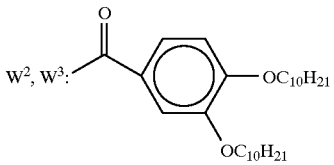 | Methyl 2-deoxy-2-(3,4-didecyloxybenzoyl)amino-3-O-(3,4-didecycloxybenzoyl)-4,6-O-isopropylidene-α-D-glucopyranoside | reference example 18 | 0.56 (AcOEt: n-hexane = 1:2) | ν 3300, 2910, 1710, 1620, 1590, 1570, 1500, 1460, 1420, 1370, 1330, 1270, 1210, 1120, 990 |
| 19 (b) | $W^1$: – –$OCH_3$ 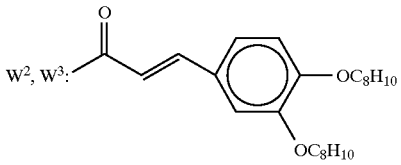 | Methyl 2-deoxy-2-[3-(3,4-dioctyloxyphenyl)propenoyl] amino-3-O-[3-(3,4-diocryloxyphenyl)propenoyl] 4,6-O-isopropylidene-α-D-glucopyranoside | reference example 18 (a) | 0.95 (AcOEt: $CH_2Cl_2$ = 1.5) | ν 3350, 2900, 2850, 1700, 1650, 1620, 1590, 1510, 1460 |
| 19 (c) | $W^1$: – –$OCH_3$ 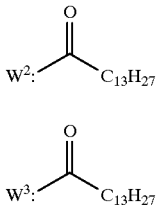 | Methyl 2-deoxy-2-tetradecanoylamino-3-(3-(3,4-dioctyloxyphenyl) propenoyl]-4,6-O-isopropylidene-α-D-glucopyranoside | reference example 16 (f) | 0.80 (AcOEt: $CH_2Cl_2$ = 1:3) | ν 3270, 2930, 2850, 1710, 1640, 1510 |

REFERENCE EXAMPLE 20

Synthesis of benzyl 2-deoxy-2-(3,4-didecyloxybenzoyl)amino-3-O-tetradecanoyl-4,6-O-isopropylidene-β-D-glucopyranoside

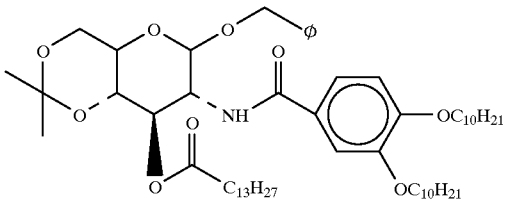

Tetradecanoyl chloride (0.27 ml) was added to a solution of the compound (600 mg) prepared in reference example 17 and pyridine (0.16 ml) in methylene chloride (5 ml) at room temperature. After the mixture was stirred for two hours, methylene chloride (40 ml) was added to this reaction solution.

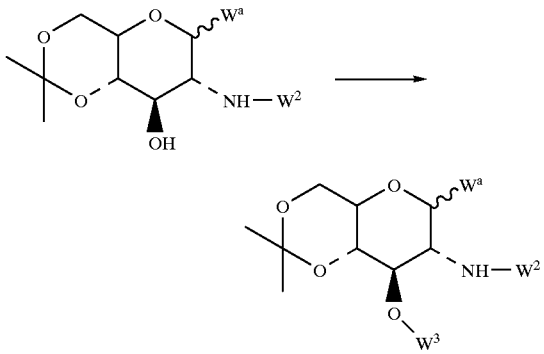

TABLE XIV

| No. | $W^2$,$W^3$,$W^a$ | Name | Starting material | TLC | IR ($cm^{-1}$) |
|---|---|---|---|---|---|
| 20 (a) | 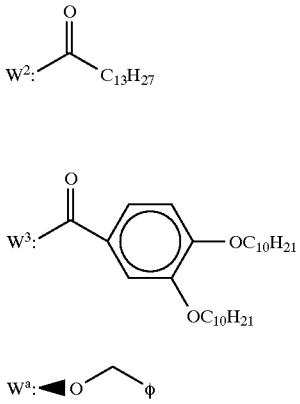 | Benzyl 2-deoxy-2-tetradecanoylamino-3-O-(3,4-didecyloxybenzoyl)-4,6-O-isopropylidene-β-D-glucopyranoside | reference example 17 (a) | 0.72 (AcOEt: chloroform = 1:10) | ν 3340, 2900, 2840, 1705, 1645, 1590, 1510, 1455, 1420, 1260, 1195, 1070 |
| 20 (b) | 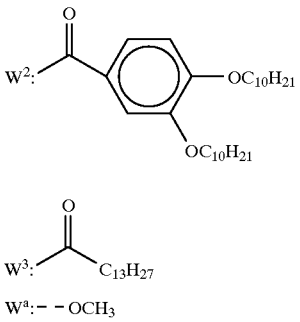 | Methyl 2-deoxy-2-(3,4-didecyloxybenzoyl)amino-3-O-tetradecanoyl-4,6-O-isopropylidene-α-D-glucopyranoside | reference example 18 | 0.49 (AcOEt n-hexane = 1:2) | |
| 20 (c) | 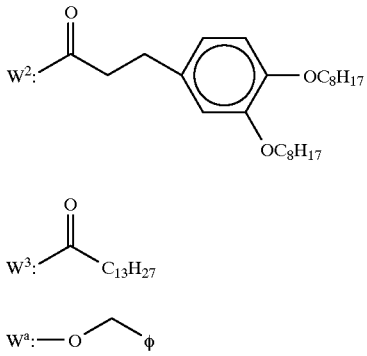 | Benzyl 2-deoxy-2-[3-(3,4-dioctyloxy)phenyl-propionyl]amino-3-O-tetradecanoyl-4,6-O-isopropylidene-β-D-glucopyranoside | reference example 17 (b) | (1,49 (AcOEt n-hexane = 1:3) | ν 3350, 2910, 2845 1710, 1650, 1520, 1470, 1255, 1240 |
| 20 (d) | 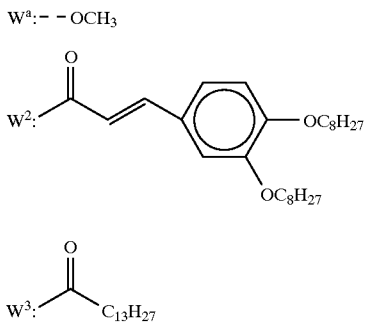 | Methyl 2-deoxy-2-[3-(3,4-dioctyloxyphenyl)propenyl] amino-3-O-tetradecanoyl-4,6-O-isopropylidene-α-D-glucopyranoside | reference example 18 (a) | 0.81 (AcOEt: $CH_2Cl_2$ = 1:5) | ν 3370, 2930, 2850, 1730, 1660, 1620, 1600, 1510 |

REFERENCE EXAMPLE 20-1

Synthesis of methyl 2-deoxy-2-[3-(3,4-dioctyloxyphenyl)propanoyl]amino-3-O-tetradecanoyl-4,6-O-isopropylidene-α-D-glucopyranoside

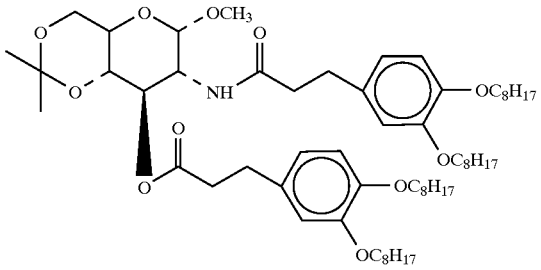

10% Pd-c (0.2 g) was added to a solution of the compound (1 g) prepared in reference example 19(b), of THF (20 ml). Under an atmosphere of hydrogen, the mixture was stirred overnight at room temperature.

After the reaction, the catalyst was filtered off, and the filtrate was evaporated to give the title compound (0.98 g) having the following physical data:

TLC: Rf 0.61 (AcOEt:n-hexane:$CH_2Cl_2$=1:3:1);

IR: ν3270, 2910, 2850, 1730, 1650, 1510, 1460 $cm^{-1}$.

REFERENCE EXAMPLES 20-1(a)~20-1(b)

By the same procedure as in reference example 20-1, using the starting materials specified, the following compounds having the physical data shown in table XV were gprepared:

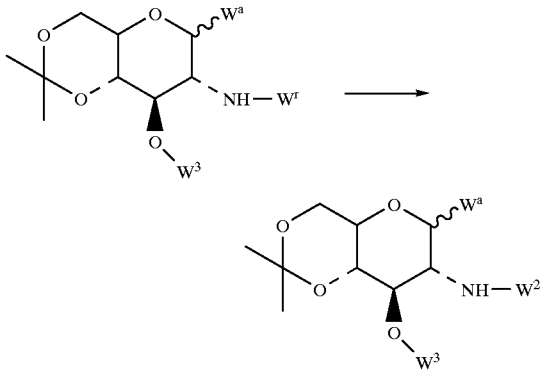

TABLE XV

| No. | $W^a$,$W^{2'}$,$W^{3'}$,$W^2$,$W^3$ | Name | Starting material | TLC | IR ($cm^{-1}$) |
|---|---|---|---|---|---|
| 20-1 (a) | $W^a$: – – $OCH_3$<br>$W^{2'}$: 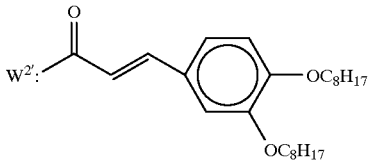 <br>$W^{3'}$: 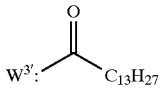 <br>$W^2$: 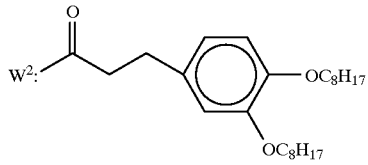 <br>$W^3$: 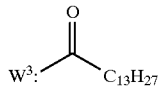 | Methyl 2-deoxy-2-[3-(3,4-dioctyloxyphenyl)propanolyl] amino-3-O-tetradecanoyl-4,6-O-isopropylidene-α-D-glucopyranoside | reference example 20 (d) | 0.61 (AcOEt: $CH_2Cl_2$: n-hexane = 1:1:3) | ν 3370, 2920, 2850, 1730, 1660, 1510, 1460 |

TABLE XV-continued

| No. | $W^a, W^{2'}, W^{3'}, W^2, W^3$ | Name | Starting material | TLC | IR ($cm^{-1}$) |
|---|---|---|---|---|---|
| 20-1 (b) | $W^a$: – –$OCH_3$<br>$W^{2'}$: 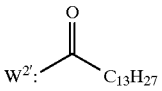 <br>$W^{3'}$: 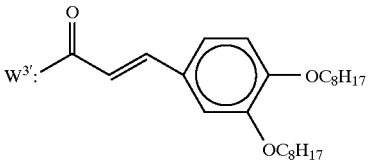 <br>$W^2$: 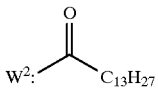 <br>$W^3$: 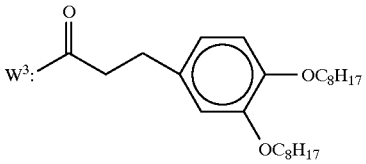 | Methyl 2-deoxy-2-tetradecanoylamono-3-O-[3-(3,4-dioctyloxyphenyl) propanoyl]-4,6-O-isopropylidene-α-D-glucopyranoside | reference example 19 (c) | 0.61 (AcOEt: $CH_2Cl_2$: n-hexane = 1:1:3) | ν 3300, 2910, 2850, 1730, 1640, 1510 |

REFERENCE EXAMPLE 21

Synthesis of benzyl 2-deoxy-2-(3,4-didecyloxybenzoyl)amino-3-O-tetradecanoyl-β-D-glucopyranoside

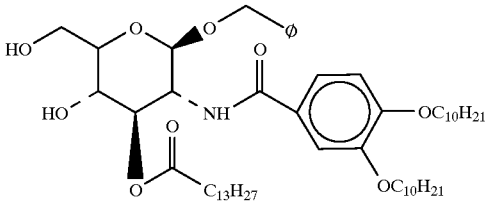

Water (4 ml) and acetic acid (8 ml) were added into a solution of the crude product prepared in reference example 20 in THF (16 ml), and the mixture was stirred for 6 hours under reflux.

The reaction solution was evaporated, and the obtained residue was dissolved in the mixture of ethyl acetate-methylene chloride (4:1; 50 ml), and washed with successively, 1N aqueous solution of sodium hydroxide and water. THF (20 ml) and methylene chloride (20 ml) were added into an organic layer.

This solution was dried, and evaporated to give the crude title compound having the following physical data:

TLC: Rf O ($CH_2Cl_2$:EtOAc=1:10).

REFERENCE EXAMPLES 21(a)~21(h)

By the same procedure as in reference example 21, using the starting materials specified, the following compounds having the physical data shown in Table XVI were prepared:

TABLE XVI

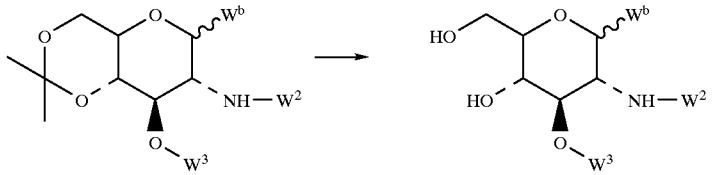

| No. | $W^2$, $W^3$, $W^b$ | Name | Starting material | TLC | IR ($cm^{-1}$) |
|---|---|---|---|---|---|
| 21 (a) | $W^2$: 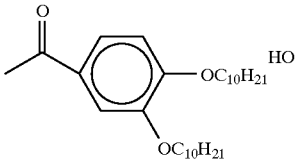 <br>$W^3$: 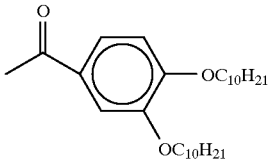 <br>$W^b$: 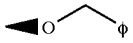 | Benzyl 2-deoxy-2-(3,4-didecyloxybenzoyl)amino-3-O-(3,4-didecyloxybenzoyl)-β-D-Glucopyranoside | reference example 19 | | |
| 21 (b) | $W^2$: 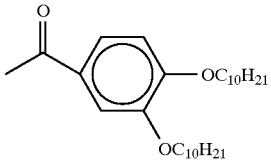 <br>$W^3$: 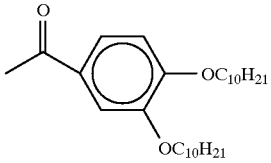 <br>$W^b$: $---OCH_3$ | Methyl 2-deoxy-2-(3,4-didecyloxybenzoyl)amino-3-O-(3,4-didecyloxybenzoyl)-α-D-glucopyranoside | reference example 19 (a) | 0.05 (AcOET:n-hexane = 1:3) | ν3400, 3250, 2900, 2820, 1670, 1620, 1590, 1585, 1500, 1450, 1410, 1370 1320, 1260, 1210, 1120, 1030 |
| 21 (c) | $W^2$: 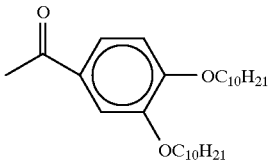 <br>$W^3$: 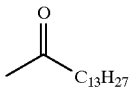 <br>$W^b$: 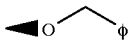 | Benzyl 2-deoxy-2-(3,4-dideclyloxybenzoyl)amino-3-O-tetradecanoyl-β-D-glucopyranoside | reference example 20 | | |
| 21 (d) | $W^2$: 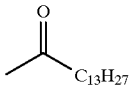 | Benzyl 2-deoxy-2-tetradecanoyl-3-O-(3,4-didecyloxybenzoyl)-β-D-glucopyranoside | reference example 20 (a) | 0.06 (AcOEt:chloroform = 1:10) | ν3380, 3310, 2900, 2845, 1670, 1645, 1590, 1525, 1460, 1270, 1210, 1090 |

TABLE XVI-continued

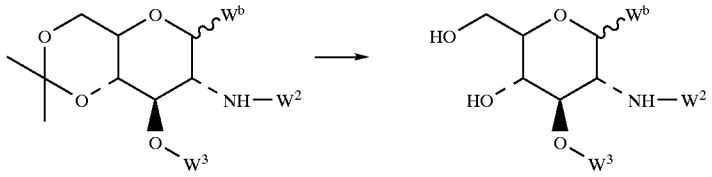

| No. | $W^2$, $W^3$, $W^b$ | Name | Starting material | TLC | IR ($cm^{-1}$) |
|---|---|---|---|---|---|
| | $W^3$: 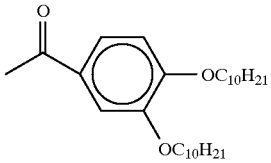 $W^b$: 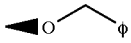 | | | | |
| 21 (e) | $W^2$: 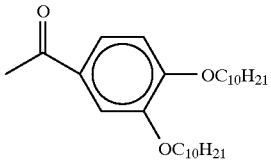 $W^3$: 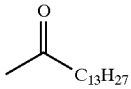 $W^b$: 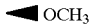 | Methyl 2-deoxy-2-(3,4-didecyloxybenzoyl)amino-3-O-tetradecanoyl-β-D-glucopyranoside | reference example 20 (b) | 0.58 (MeOH:chloroform = 1:9) | ν3440, 2910, 2840, 1710, 1630, 1490, 1260 |
| 21 (f) | $W^2$: 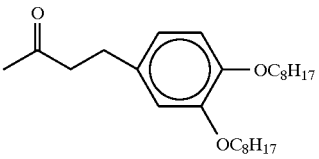 $W^3$: 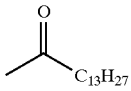 $W^b$: 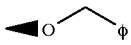 | Benzyl 2-deoxy-2-[3-(3,4-dioctyloxy)phenylpropionyl]amino-3-O-tetradecanoyl-β-D-glucopyranoside | reference example 20 (c) | 0.38 ($AcOEt:CH_2Cl_2$ = 1:2) | ν3450, 2930, 2855, 1730, 1675, 1505 |
| 21 (g) | $W^2$: 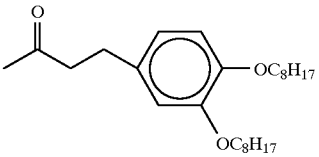 $W^3$: 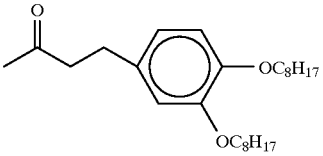 $W^b$:  | Methyl 2-deoxy-2-[3-(3,4-dioctyloxy)propanoyl)amino-3-O-[3-(3,4-dioctyloxy)propanoyl]-α-D-glucopyranoside | reference example 20-1 | 0.30 ($AcOEt:CH_2Cl_2$: n-hexane = 3:1:3) | ν3420, 3370, 2920, 2850, 1720, 1650, 1590, 1510, 1460 |

TABLE XVI-continued

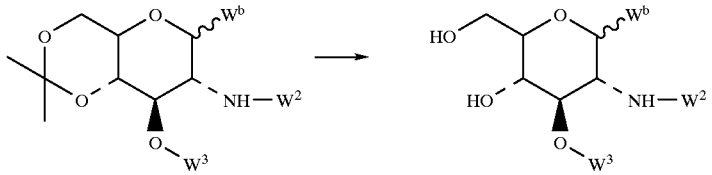

| No. | $W^2$, $W^3$, $W^b$ | Name | Starting material | TLC | IR ($cm^{-1}$) |
|---|---|---|---|---|---|
| 21 (h) | $W^2$: 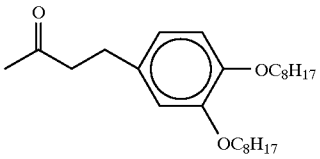 $W^3$: 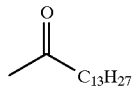 $W^b$: ---$OCH_3$ | Methyl 2-deoxy-2-[3-(3,4-dioctyloxy)propanoyl]amino-3-O-tetradecanoyl-α-D-glucopyranoside | reference example 20-1 (a) | 0.10 ($AcOEt:CH_2Cl_2$: n-hexane = 3:1:3) | ν3350, 3280, 2920, 2860, 1730, 1640 |
| 21 (i) | $W^2$: 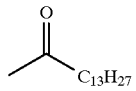 $W^3$: 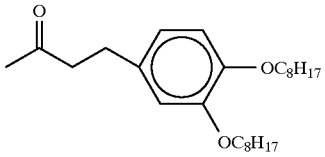 $W^b$: ---$OCH_3$ | Methyl 2-deoxy-2-tetradecanoylamino-3-O-[3-(3,4-dioctyloxy)propanoyl]-α-D-glucopyranoside | reference | ($AcOEt:CH_2Cl_2$: n-hexane = 3:1:3) | ν3370, 3300, 2920, 1730, 1640, 1540, 1510 |

REFERENCE EXAMPLE 22

Synthesis of benzyl 2-deoxy-2-(3,4-didecyloxybenzoyl)amino-3-O-tetradecanoyl-6-O-t-butyldimethylsilyl-β-D-glucopyranoside

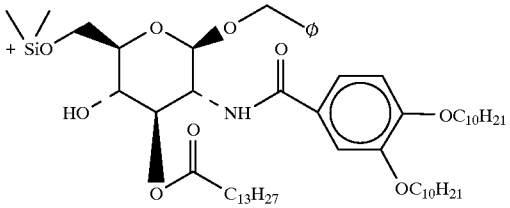

4-(N,N-dimethylamino)pyridine (122 mg) was added to a solution of the compound prepared in reference example 21 in dry pyridine (10 ml), and the mixture was stirred for 5 hours at room temperature.

The reaction solution was evaporated, and the obtained residue was dissolved in methylene chloride (60 ml), and the solution was washed with successively, 1N aqueous solution of hydrochloric acid, water and a saturated aqueous solution of sodium bicarbonate, and then evaporated.

The residue was purified by column chromatography on silica-gel ($CH_2Cl_2$:EtOAc=20:1) to give the title compound (856 mg) having the following physical data:

TLC: Rf 0.66 ($CH_2Cl_2$:EtOAc=10:1);

IR ($CHCl_3$): ν3476, 2940, 2860, 1726, 1660, 1600, 1497, 1462, 1264, 1075, 836 $cm^{-1}$.

REFERENCE EXAMPLES 22(a)~22(e)

By the same procedure as in reference example 22, using the starting materials specified, the following compounds having the physical data shown in Table XVII were prepared:

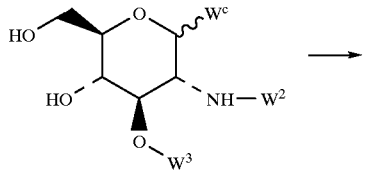

-continued

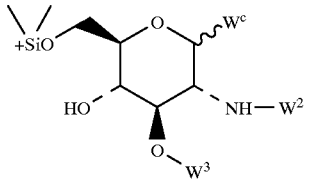

TABLE XVII

| No. | $W^2$, $W^3$, $W^c$ | Name | Starting material | TLC | IR ($cm^{-1}$) |
|---|---|---|---|---|---|
| 22 (a) | $W^2$: 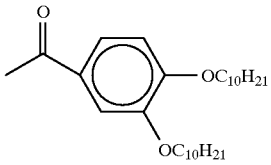 $W^3$: 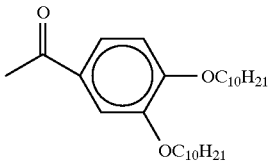 $W^c$: 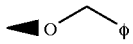 | Benzyl 2-deoxy-2-(3,4-didecyloxybenzoyl)amino-3-6-O-t-butyldimethylsilyl-β-D-glucopyranoside | reference example 21 (a) | 0.81 (AcOEt:n-hexane = 3:5) | ν3400, 3270, 2910, 2850, 1710, 1680, 1630, 1600, 1540, 1510 |
| 22 (b) | $W^2$: 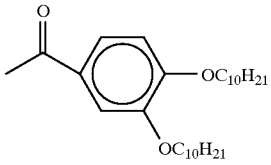 $W^3$: 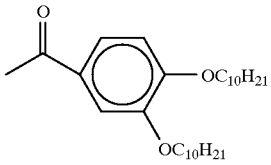 $W^c$: $---OCH_3$ | Methyl 2-deoxy-2-(3,4-didecyloxybenzoyl)-O-(3,4-didecyloxybenzoyl)-6-O-t-butyldimethylsilyl-α-D-glucopyranoside | reference example 21 (b) | 0.8 (AcOEt:n-hexane = 1:2) | ν3420, 3300, 2910, 2850, 1670, 1620, 1590, 1570, 1500, 1460, 1420, 1380, 1270, 1210, 1120, 1050 |
| 22 (c) | $W^2$: 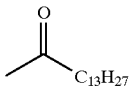 $W^3$: 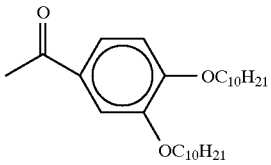 $W^c$: 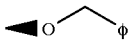 | Benzyl 2-deoxy-2-tetradecanoylamino-3-O-(3,4-didecyloxybenzoyl)-6-O-t-butyldimethylsilyl-β-D-glucopyranoside | reference example 21 (d) | 0.84 (AcOEt:n-hexane = 3:1) | ν3400, 3275, 2900, 2840, 1675, 1640, 1540, 1460, 1280, 1215, 1115 |

TABLE XVII-continued

| No. | $W^2$, $W^3$, $W^c$ | Name | Starting material | TLC | IR ($cm^{-1}$) |
|---|---|---|---|---|---|
| 22 (d) | $W^2$: 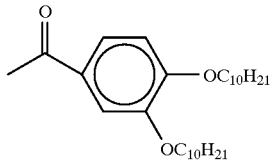 $W^3$: 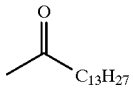 $W^c$: ---$OCH_3$ | Methyl 2-deoxy-2-(3,4-didecyloxybenzoyl)amino-3-O-tetradecanoyl-6-O-t-butyldimethylsilyl-α-D-glucopyranoside | reference example 21 (c) | 0.87 (AcOEt:n-hexane = 1:4) | ν3460, 2910, 2840, 1720, 1645, 1595, 1490, 1460, 1260 |
| 22 (e) | $W^2$: 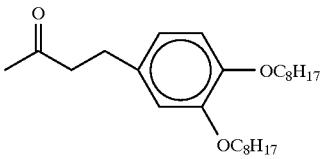 $W^3$: 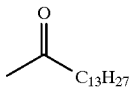 $W^c$: 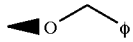 | Benzyl 2-deoxy-2-[3-(3,4-dioctyloxy)phenylpropionyl]amino-3-O-tetrandecanoyl-6-O-t-butyldimethylsilyl-β-D-glucopyranoside | reference example 21 (f) | 0.56 (AcOEt:$CH_2Cl_2$ = 1:20) | ν3450, 2920, 2850, 1720, 1675, 1505, 1460, 1255, 1080, 1060 |

REFERENCE EXAMPLE 23

Synthesis of 2-deoxy-2-[3-(9-phenylnonanoyl) oxytetradecanoyl]amino-3-O-(9-phenylnonanoyl)-1, 5-anhydro-D-xylitol

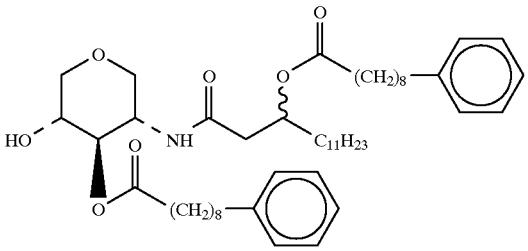

To a stirring solution of the compound (more polar; 260 mg) prepared in reference example 16 dissolved into THF, palladium-carbon (content 10% 80 mg) was added in small portions. In an atmosphere of hydrogen, the mixture was stirred overnight at 60°–70° C.

After reaction, the reaction solution was filtered. The filtrate was evaporated to give the title compound (more polar).

REFERENCE EXAMPLES 23(a)~23(j)

By the same procedures as reference example, using the starting material specified, the following compounds having the physical data shown in Table XVIII were prepared:

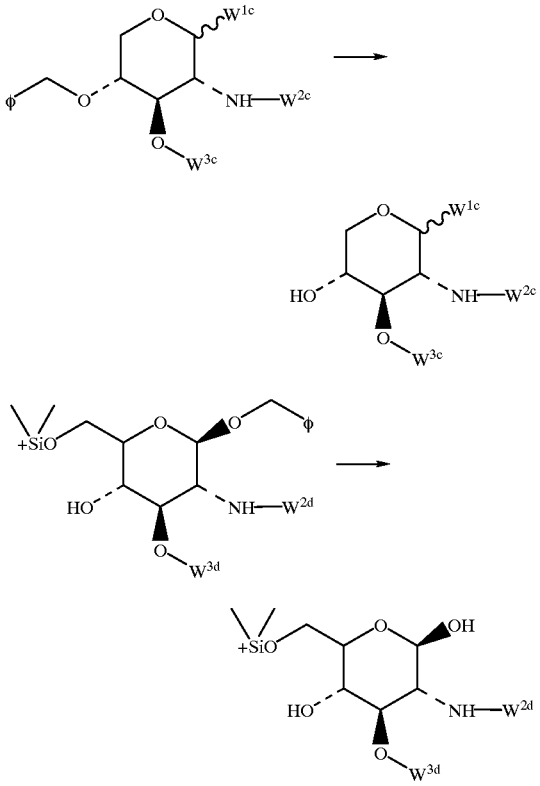

-continued

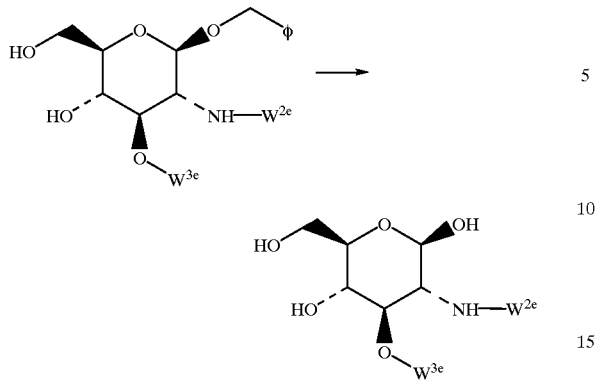

TABLE XVIII

| No. | $W^{1c}$, $W^{2c}$, $W^{3c}$, $W^{2d}$, $W^{3d}$, $W^{2e}$, $W^{3e}$ | Name | Starting material | TLC | IR ($cm^{-1}$) |
|---|---|---|---|---|---|
| 23 (a) | $W^{1c}$: —H<br>$W^{2c}$: 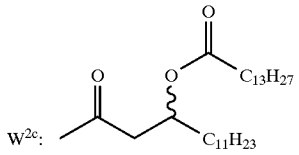 <br>$W^{3c}$: 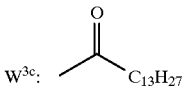 | 2-deoxy-2-(3-tetra decanoyloxytetradecanoyl) amino-3-O-tetradecanoly-1,5-anhydro-D-xylitol (less polar) | reference example 16 (b) | 0.52 (AcOEt:n-hexane = 3:5) | ν3450, 3280, 2910, 2850, 1730, 1650, 1530 |
| 23 (b) | $W^{1c}$: —H<br>$W^{2c}$: 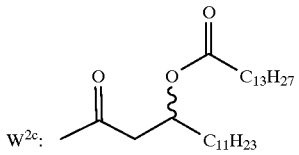 <br>$W^{3c}$: 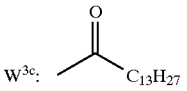 | 2-deoxy-2-(3-tetra decanoyloxytetradecanoyl) amino-3-O-tetradecanoyl-1,5-anhydro-D-xylitol (more polar) | reference example 16 (c) | 0.55 (AcOEt:n-hexane = 1:1) | ν3450, 3320, 2920, 2850, 1730, 1620, 1550 |
| 23 (c) | $W^{1c}$: —H<br>$W^{2c}$: 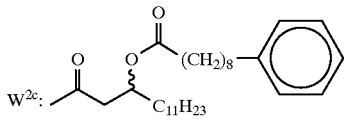 <br>$W^{3c}$: 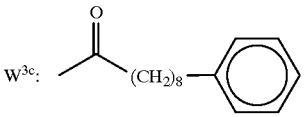 | 2-deoxy-2-[3-(9-phenyl nonanoyl)oxytetradecanoyl] amino-3-O-(9-phenyl nonanoyl)-1,5-anhydro-D-xylitol (less polar) | reference example 16 (a) | | |

TABLE XVIII-continued

| No. | $W^{1c}$, $W^{2c}$, $W^{3c}$, $W^{2d}$, $W^{3d}$, $W^{2e}$, $W^{3e}$ | Name | Starting material | TLC | IR ($cm^{-1}$) |
|---|---|---|---|---|---|
| 23 (d) | $W^{1c}$: —H<br>$W^{2c}$: 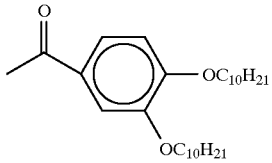 <br>$W^{3c}$: 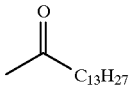 | 2-deoxy-2-(3,4-didecyloxy benzoyl)amino-3-O-tetra decanoyl-1,5-anhydro-D-xylitol | reference example 16 (d) | 0.43 (AcOEt:n-hexane = 1:1) | ν3430, 3200, 2905, 2840, 1745, 1610, 1540, 1505, 1460, 1360, 1265 |
| 23 (e) | $W^{1c}$: – –$OCH_3$<br>$W^{2c}$: 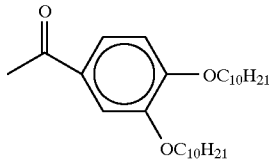 <br>$W^{3c}$: 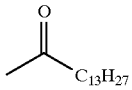 | Methyl 2-deoxy-2-(3,4-didecyloxybenzoyl)amino-O-tetradecanoyl-1,5-anhydro-α-D-xyloside | reference example 16 (e) | | |
| 23 (f) | $W^{2e}$: 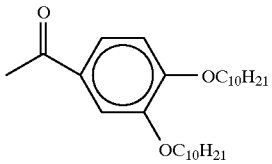 <br>$W^{3e}$: 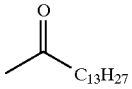 | 2-deoxy-2-(3,4-didecyloxy benzoyl)amino-3-tetra decanoyl-D-glucopyranos | reference example 21 (c) | | |
| 23 (g) | $W^{2d}$: 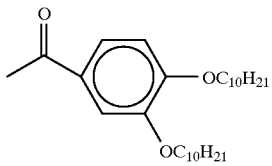 <br>$W^{3d}$: 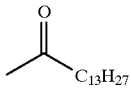 | 2-deoxy-2-(3,4-didecyloxy benzoyl)amino-3-O-tetradecanoyl-6-O-t-butyldimethylsilyl-D-glucopyranose | reference example 22 | 0.50 (AcOEt:n-hexane = 10:1) | |
| 23 (h) | $W^{2d}$: 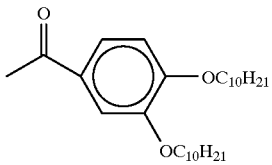 | 2-deoxy-2-(3,4-didecyloxy benzoyl)amino-3-O-(3,4-didecyloxybenzoyl)-6-O-t-butyldimethylsilyl-D-glucopyranose | reference example 22 (a) | 0.63 (AcOEt:n-hexane = 3:5) | ν3400, 3270, 2910, 2850, 1710, 1680, 1630, 1600, 1540, 1510 |

TABLE XVIII-continued

| No. | $W^{1c}$, $W^{2c}$, $W^{3c}$, $W^{2d}$, $W^{3d}$, $W^{2e}$, $W^{3e}$ | Name | Starting material | TLC | IR ($cm^{-1}$) |
|---|---|---|---|---|---|
| | $W^{3d}$: 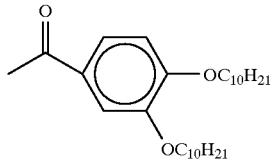 | | | | |
| 23 (i) | $W^{2d}$: 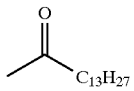 $W^{3d}$: 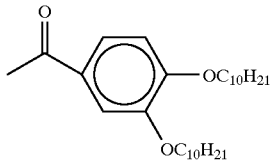 | 2-deoxy-2-tetradecanoylamino-3-O-(3,4-didecyloxybenzoyl)-6-O-t-butyldimethylsilyl-D-glucopyranose | reference example 22 (c) | 0.28 ($AcOEt:CH_2Cl_2$ = 1:10) | ν3450, 2930, 2820, 1690, 1595, 1500, 1480, 1260 (neat) |
| 23 (j) | $W^{2d}$: 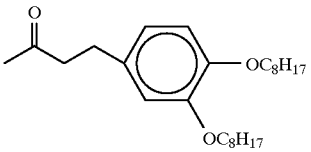 $W^{3d}$: 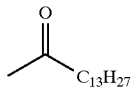 | 2-deoxy-2-[3-(3,4-dioctyloxy)phenylpropyonyl]amino-3-O-tetradecanoyl-6-O-t-butyldimethylsilyl-D-glucopyranose | reference example 22 (e) | 0.40 ($AcOEt:CH_2Cl_2$ = 1:10) | ν3450, 2965, 2840, 1720, 1660, 1500, 1460, 1250, 1075, 825 |

EXAMPLE 3

Synthesis of *salt form of* 2-deoxy-2-[3-(9-phenylnonanoyl)oxytetradecanoyl]amino-3-O-(9-phenylnonanoyl)-4-O-sulfo-1,5-anhydro-D-xylitol

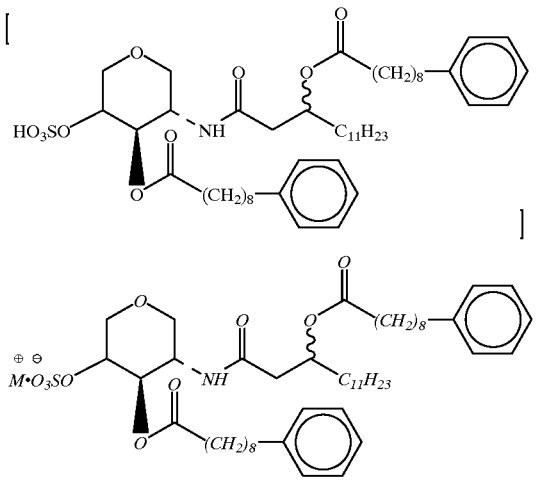

The mixture of a crude products (200 mg) prepared in reference example 23, sulfur trioxide-pyridine complex (144 mg) and pyridine (8 ml) was stirred for 3 hours at room temperature.

After reaction, pyridine was separated as the toluene azeotrope. The residue was purified by column chromatography on silica-gel ($CH_2Cl_2$:$CH_3OH$=10:1) to give the title compound (more polar; 180 mg) having the following physical data[:]. *The title compound was obtained in the pyridine salt form, but a part of the pyridine salt was converted into a mixture of calcium, sodium and magnesium salts by salt-exchanging with calcium, sodium and magnesium ions which were present in the silica gel as impurities.*

TLC: Rf 0.44 ($CH_2Cl_2$:$CH_3OH$=5:1);

IR: ν3450, 3280, 2910, 2850, 1720, 1640, 1520, 1450, 1370, 1250, 1160, 1090, 1060, 990, 810, 740, 690 $cm^{-1}$.

EXAMPLES 3(a)~3(e)

By the same procedure as in example 3, using the starting material specified, the following compounds having the physical data shown in Table XIX were prepared[:]. *The title compounds were obtained in the pyridine salt form, but a part of the pyridine salt in each example was converted into a mixture of calcium, sodium and magnesium salts by salt-exchanging with calcium, sodium and magnesium ions which were present in the silica gel as impurities.*

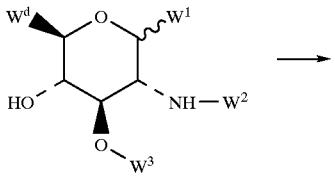

-continued

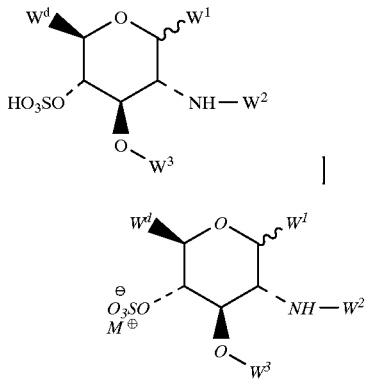

TABLE XIX

| No. | $W^1$, $W^2$, $W^3$, $W^d$ | Name *salt form of* | Starting material | TLC | IR ($cm^{-1}$) |
|---|---|---|---|---|---|
| example 3 (a) | $W^2$: 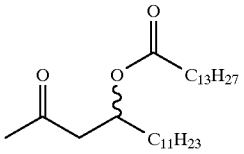 $W^3$: 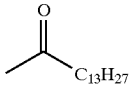 $W^1$, $W^d$: —H | 2-deoxy-2-[3-tetradecanoyl oxytetradecanoyl]amino-3-O-tetradecanoyl-4-O-sulfo-1,5-anhydro-D-xylitol (less polar) | reference example 23 (a) | 0.23 ($CH_2Cl_2$: MeOH = 10:1) | ν3450, 2910, 2840, 2670, 1720, 1650, 1530, 1460, 1370, 1260, 1220(S), 1160, 1100, 1050, 990, 800, 710 |
| example 3 (b) | $W^2$: 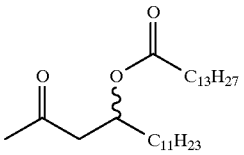 $W^3$: 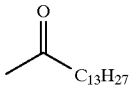 $W^1$, $W^d$: —H | 2-deoxy-2-[3-tetradecanoyl oxytetradecanoyl]amino-3-O-tetradecanoyl-4-O-sulfo-1,5-anhydro-D-xylitol (more polar) | reference example 23 (b) | 0.20 ($CH_2Cl_2$: MeOH = 10:1) | ν3450, 3280, 2900, 2840, 1730, 1650, 1540, 1470, 1380, 1250, 1200, 1170, 1100, 1060, 1000, 810 |
| example 3 (c) | $W^2$: 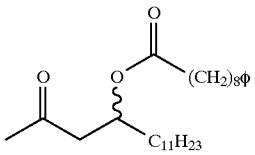 $W^3$: 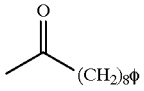 $W^1$, $W^d$: —H | 2-deoxy-2-[3-(9-phenylnonanoyl)oxytetradeca noyl]amino-3-O-(9-phenylnonanoyl)-4-O-sulfo-1,5-anhydro-D-xylitol (less polar) | reference example 23 (c) | 0.49 ($CH_2Cl_2$: MeOH = 5:1) | ν3450, 3300, 2910, 2840, 1720, 1650, 1540, 1450, 1380, 1260, 1230, 1170, 1090, 1060, 1000, 810, 740, 690 |

TABLE XIX-continued

| No. | $W^1$, $W^2$, $W^3$, $W^d$ | Name *salt form of* | Starting material | TLC | IR ($cm^{-1}$) |
|---|---|---|---|---|---|
| example 3 (d) | $W^2$: 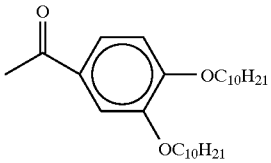 <br>$W^3$: 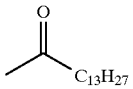 <br>$W^1$, $W^d$: —H | 2-deoxy-2-(3,4-didecyloxybenzoyl)amino-3-O-tetradecanoyl-4-O-sulfo-1,5-anhydro-D-xylitol | reference example 23 (d) | 0.33 (chloroform: MeOH = 10:1) | ν3425, 3360, 2910, 1725, 1635, 1505, 1260, 1215 |
| example 3 (e) | $W^1$: —$OCH_3$<br>$W^2$: 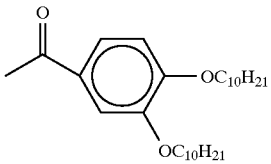 <br>$W^3$: 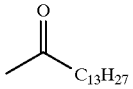 <br>$W^d$: —H | Methyl 2-dexoy-2-(3,4-didecyloxybenzoyl)amino-3-O-tetradecanoyl-4-O-sulfo-1,5-anhydro-α-D-xyloside | reference example 23 (e) | 0.30 ($CH_2Cl_2$: MeOH = 10:1) | ν3420, 3350, 2910, 1720, 1640, 1510, 1270, 1210 |

*REFERENCE EXAMPLES 24(a)~24(f)*

*By the same procedure as in Example 3, except for purification by column chromatography, using the starting material specified, the following compounds having the physical data shown in Table XIX (A) were prepared:*

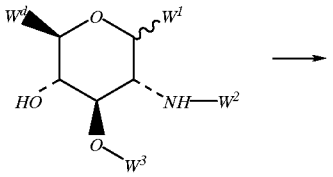

-continued

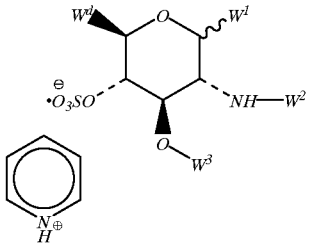

TABLE XIX(A)

| No. | $W^1$, $W^2$, $W^3$, $W^d$ | Name - Pyridine Salt of | Starting material | TLC | IR ($cm^{-1}$) |
|---|---|---|---|---|---|
| reference example 24 (a) | $W^1$: ∿OH<br>$W^2$: 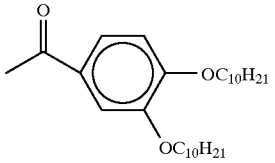 <br>$W^3$: 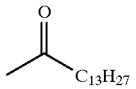 <br>$W^d$: 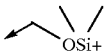 | 2-deoxy-2-(3,4-didecyloxybenzoyl)amino-3-O-tetradecanoyl-4-O-sulfo-6-O-t-butyldimethylsilyl-D-glucopyranose | reference example 23 (g) | 0.20 ($CH_2Cl_2$: MeOH = 10:1) | |
| reference example 24 (b) | $W^1$: ∿OH<br>$W^2$: 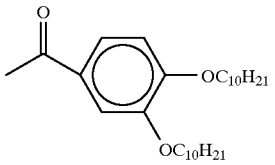 <br>$W^3$: 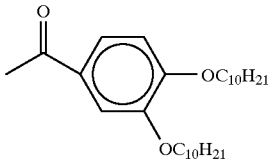 <br>$W^d$: 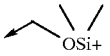 | 2-deoxy-2-(3,4-didecyloxy benzoyl)amino-3-O-(3,4-didecyloxybenzoyl)-4-O-sulfo-6-O-t-butyldimethyl silyl-D-glucopyranose | reference example 23 (h) | | |
| reference example 24 (c) | $W^1$: – –$OCH_3$<br>$W^2$: 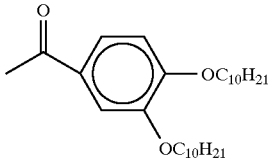 <br>$W^3$: 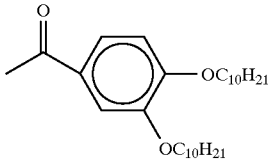 <br>$W^d$: 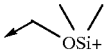 | Methyl 2-deoxy-2-(3,4-didecyloxybenzoyl)amino-3-O-(3,4-didecyloxybenzoyl)-4-O-sulfo-6-O-t-butyldiemthylsilyl-D-glucopyranoside | reference example 22 (b) | 0.68 ($CH_2Cl_2$: MeOH = 20:3) | |
| reference example 24 (d) | $W^1$: ∿OH<br>$W^2$: 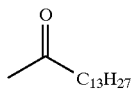 | 2-deoxy-2-(tetradecanoyl amino)-3-O-(3,4-didecyloxy benzoyl)-4-O-sulfo-6-O-t-butyldiemthylsilyl-D-glucopyranose | reference example 23 (i) | | |

TABLE XIX(A)-continued

| No. | $W^1$, $W^2$, $W^3$, $W^d$ | Name - Pyridine Salt of | Starting material | TLC | IR ($cm^{-1}$) |
|---|---|---|---|---|---|
| | $W^3$: 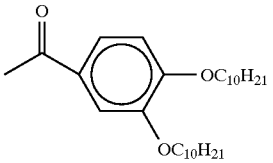 $W^d$: 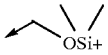 | | | | |
| reference example 24 (e) | $W^1$: $-\,-OCH_3$ $W^2$: 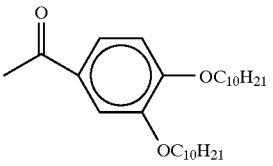 | Methyl 2-deoxy-2-(3,4-didecyloxybenzoyl)amino-3-O-tetradecanoyl-4-O-sulfo-6-O-t-butyldimethylsilyl-D-glucopyranoside | reference example 22 (d) | | |
| | $W^3$: 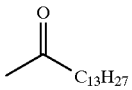 $W^d$: 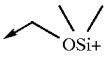 | | | | |
| reference example 24 (f) | $W^1$: $\sim OH$ $W^2$: 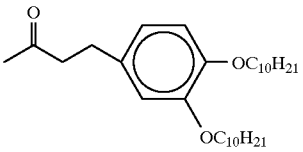 | 2-deoxy-2-[3-(3,4-dioctyloxy)phenylpropionyl] amino-3-O-tetradecanoyl-4-O-sulfo-6-O-t-butyldimethyl silyl-D-glucopyranose | reference example 23 (j) | 0.5 ($CH_2Cl_2$: MeOH = 10:1) | |
| | $W^3$: 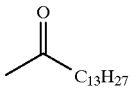 $W^d$: 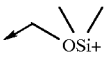 | | | | |

EXAMPLE 4

Synthesis of *salt form of* 2-deoxy-2-(3,4-didecyloxybenzoyl)amino-3-O-tetradecanoyl-4-O-sulfo-D-glycopyranose

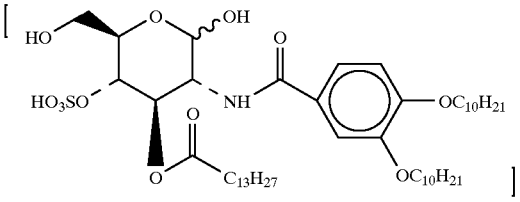

-continued

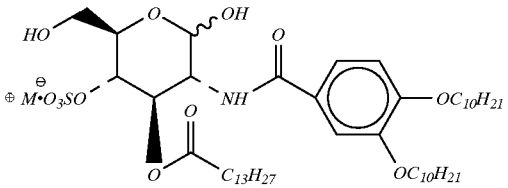

The crude products prepared in reference example 24(a) was dissolved in a mixed solvent of acetic acid (10 ml), THF (10 ml) and water (5 ml), and stirred for 30 minutes at 50° C. After reaction, the reaction solution was evaporated, and acetic acid was separated as the toluene azeotrope.

Further, the reaction solution was evaporated. The residue was purified by column chromatography on silica-gel ($CH_2Cl_2$:$CH_3OH$=20:3). To the compound obtained, dry dioxan was added, and the solution was freeze-dried to give the title compound (261 mg) having the following physical data[:]. *The title compound was obtained in the pyridine salt form, but a part of the pyridine salt was converted into a mixture of calcium, sodium and magnesium salts by salt-exchanging with calcium, sodium and magnesium ions which were present in the silica gel as impurities.*

TLC: Rf 0.15 ($CH_2Cl_2$:$CH_3OH$=20:3);

IR: ν3450, 2940, 2860, 1730, 1632, 1601, 1580, 1522, 1507, 1460, 1272, 1227, 1130, 1043, 996, 816, 765, 720, 600 $cm^{-1}$.

EXAMPLES 4(a)~4(e)

By the same procedure as in reference example 16, using the starting material specified, the following compounds having the physical data shown in Table XX were prepared[:]. *The title compounds were obtained in the pyridine salt form, but a part of the pyridine salt in each example was converted into a mixture of calcium, sodium and magnesium salts by salt-exchanging ions which were present in the silica gel as impurities.*

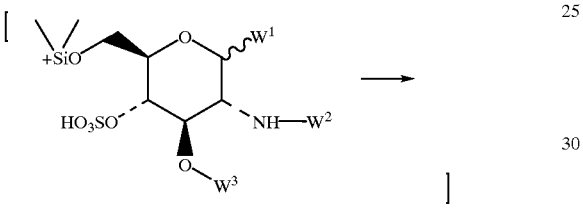

-continued

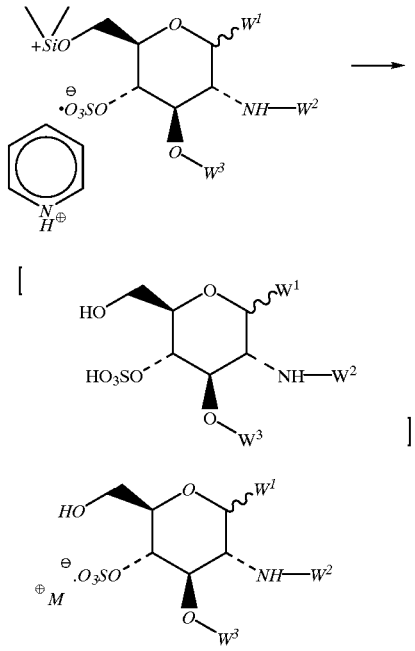

TABLE XX

| No. | $W^1$, $W^2$, $W^3$ | Name - *salt form of* | Starting material | TLC | IR ($cm^{-1}$) |
|---|---|---|---|---|---|
| 4 (a) | $W^1$: ∿OH<br>$W^2$: 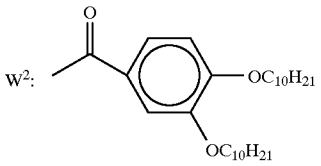 <br>$W^3$: 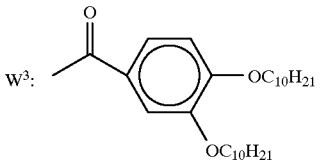 | 2-deoxy-2-(3,4-didecyloxybenzoyl)amino-3-O-(3,4-didecyloxybenzoyl)-4-O-sulfo-D-glucopyranose | reference exampel 24 (b) | 0.10 ($CH_2Cl_2$:MeOH = 9:1) | ν3420, 2910, 2850, 1700, 1630, 1600, 1510, 1460, 1420, 1350, 1270, 1210, 1130, 1030, 990 |
| 4 (b) | $W^1$: – –$OCH_3$<br>$W^2$: 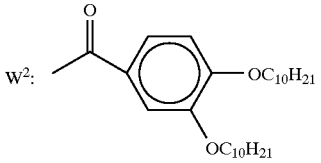 | Methyl 2-deoxy-2-(3,4-didecyloxybenzoyl)amino-3-O-(3,4-didecyloxybenzoyl)-4-O-sulfo-α-D-glucopyranoside | reference example 24 (c) | 0.50 ($CH_2Cl_2$:MeOH = 20:3) | ν3400, 2920, 2850, 1690, 1630, 1600, 1500, 1460, 1420, 1370, 1260, 1210, 1120, 1030, 990 |

TABLE XX-continued

| No. | $W^1$, $W^2$, $W^3$ | Name - *salt form of* | Starting material | TLC | IR ($cm^{-1}$) |
|---|---|---|---|---|---|
| | $W^3$: 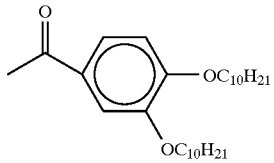 | | | | |
| 4 (c) | $W^1$: ∿OH<br>$W^2$: 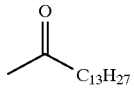 <br>$W^3$: 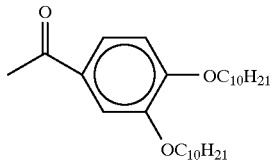 | 2-deoxy-2-tetradecanoyl amino-3-O-(3,4-didecyloxy benzoyl)amino-4-O-sulfo-D-glucopyranose | reference example 24 (d) | 0.29 ($CH_2Cl_2$:MeOH = 20:3) | ν3350, 2910, 2835, 1110, 1605, 1265, 1205 |
| 4 (d) | $W^1$: – –$OCH_3$<br>$W^2$: 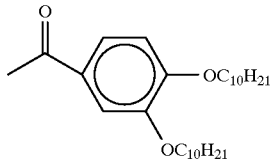 <br>$W^3$: 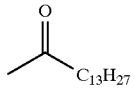 | Methyl 2-deoxy-2-(3,4-didecyloxybenzoyl)amino-3-O-tetradecanoyl-4-O-sulfo-α-D-glucopyranoxide | reference example 24 (e) | 0.24 ($CH_2Cl_2$:MeOH = 20:3) | ν3425, 2910, 2840, 1720, 1635, 1495, 1260 |
| 4 (e) | $W^1$: ∿OH<br>$W^2$: 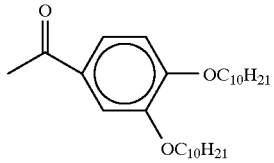 <br>$W^3$: 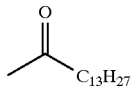 | 2-deoxy-2-[3-(3,4-dioctyloxy)phenylpropionyl] amino-3-O-tetradecanoyl-4-O-sulfo-D-glucopyranose | reference example 24 (f) | 0.29 ($CH_2Cl_2$:MeOH = 20:3) | ν3400, 2915, 2850, 1720, 1640, 1520, 1460, 1260 |

EXAMPLE 5

Synthesis of *salt form of* 2-deoxy-2-(3,4-didecyloxybenzoyl)amino-3-O-tetradecanoyl-4,6-O-disulfo-D-glucopyranose

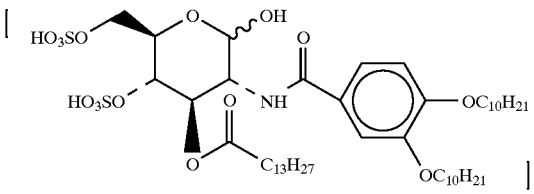

-continued

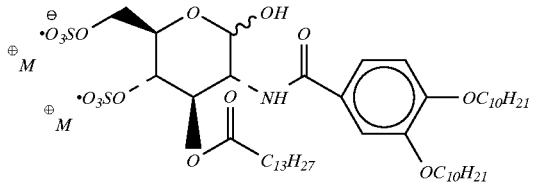

By the same procedure as in example 3, using the compound (0.57 g) prepared in reference example 9(f), the title compound having the following physical data was prepared. In this case, a two-fold amount of a sulfur trioxide-pyridine complex which was used in example 3 was used. *The title*

*compound was obtained in the pyridine salt form, but a part of the pyridine salt was converted into a mixture of calcium, sodium and magnesium salts by salt-exchanging with calcium, sodium and magnesium ions which were present in the silica gel as impurities.*

TLC: Rf 0.16 ($CH_2Cl_2$:MeOH=4:1);

IR: ν 3400, 2920, 2850, 1730, 1630, 1600, 1570, 1540, 1510, 1460, 1380, 1340, 1260, 1210, 1000 $cm^{-1}$.

EXAMPLES 5(a)~5(d)

By the same procedure as in example 5, using the starting material specified, the following compounds having the physical data shown in Table XXI were prepared[:]. *The title compounds were obtained in the pyridine salt form, but a part of the pyridine salt in each example was converted into a mixture of calcium, sodium and magnesium salts by salt-exchanging with calcium, sodium and magnesium ions which were present in the silica gel as impurities.*

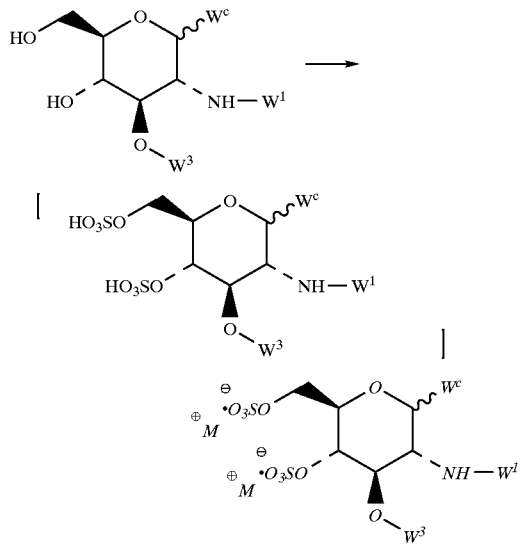

TABLE XXI

| No. | $W^1$, $W^2$, $W^3$ | Name - *salt form of* | Starting material | TLC | IR ($cm^{-1}$) |
|---|---|---|---|---|---|
| 5 (a) | $W^1$: – –$OCH_3$<br>$W^2$: 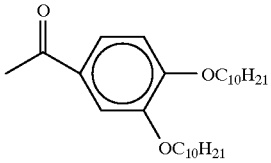 <br>$W^3$: 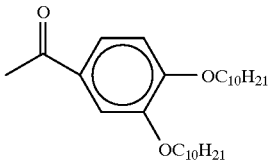 | Methyl 2-deoxy-2-(3,4-didecyloxybenzoyl)amino-3-O-(3,4-didecyloxybenzoly)-4,6-O-disulfo-α-D-glucopyranoside | reference example 21 (b) | 0.50 ($CH_2Cl_2$:MeOH = 4:1) | ν3400, 2930, 2850, 1690, 1630, 1600, 1510, 1460, 1430, 1270, 1210, 1130, 1010, 870, 820, 760, 600 |
| 5 (b) | $W^1$: – –$OCH_3$<br>$W^2$: 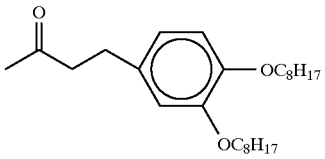 <br>$W^3$: 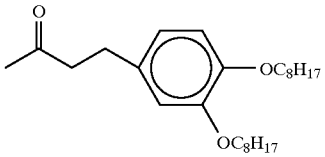 | Methyl 2-deoxy-2-[3-(3,4-dioctyloxyphenyl)propanoyl]amino-3-O-[3-(3,4-dioctyloxyphenyl)propanoyl]-4,6-O-disulfo-α-D-glucopyranoside | reference example 21 (g) | 0.15 ($CH_2Cl_2$:MeOH = 20:3) | ν3410, 2920, 2850, 1720, 1630, 1510, 1460, 1240, 1010 |

TABLE XXI-continued

| No. | $W^1$, $W^2$, $W^3$ | Name - *salt form of* | Starting material | TLC | IR ($cm^{-1}$) |
|---|---|---|---|---|---|
| 5 (c) | $W^1$: – – $OCH_3$<br>$W^2$: 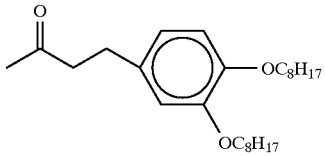 <br>$W^3$: 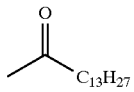 | Methyl-2-deoxy-2-[3-(3,4-dioctyloxyphenyl)propanoyl] amino-3-O-tetradecanoyl-4,6-O-disulfo-α-D-glucopyranoside | reference example 21 (h) | 0.14 ($CH_2Cl_2$:MeOH = 20:3) | ν3400, 2920, 2850, 1720, 1630, 1510, 1460, 1220, 1000, 920 |
| 5 (d) | $W^1$: – – – $OCH_3$<br>$W^2$: 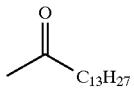 <br>$W^3$: 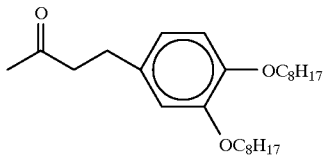 | Methyl 2-deoxy-2-tetradecanoylamino-3-O-[3-(3,4-dioctyloxyphenyl) propanoyl]-4,5-O-disulfo-α-D-glucopyranoside | reference example 21 (i) | 0.16 ($CH_2Cl_2$:MeOH = 20:3) | ν3400, 2910, 2840, 1720, 1630, 1500, 1460, 1370, 1220, 1050 |

What is claimed is:

1. A glucopyranose compound of formula (I) or (IA):

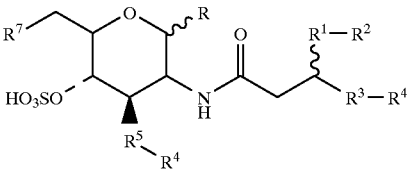

(I)

wherein R represents a hydrogen atom, a hydroxy group or an alkoxy group of from 1 to 4 carbon atom(s);

$R^1$ represents a single bond or an oxycarbonylalkylene group of from 2 to 20 carbon atoms;

$R^2$ and $R^6$, independently, represent a hydrogen atom or a general formula:

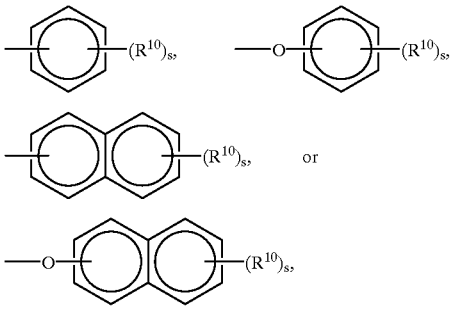

wherein $R^{10}$ represents a hydrogen atom, an alkyl or alkoxy group of from 1 to 7 carbon atom(s) or a halogen atom, and s represents 1, 2 or 3, respectively;

$R_3$ represents an alkylene group of from 1 to 20 carbon atom(s);

$R^4$ represents a hydrogen atom or a formula:

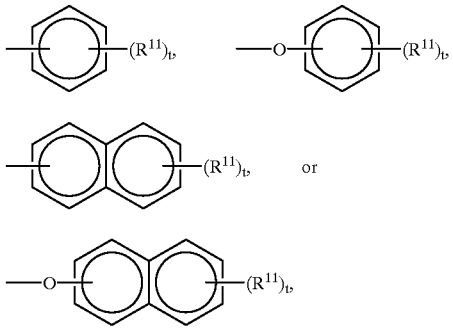

wherein $R^{11}$ represents a hydrogen atom, an alkyl or alkoxy group of from 1 to 7 carbon atom(s) or a halogen atom, and t represents 1, 2 or 3;

$R^5$ represents an oxycarbonylalkylene group of from 2 to 20 carbon atoms;

$R^7$ represents a hydrogen atom or a hydroxy group;

with the proviso that $R^2$, $R^4$ and $R_6$ do not represent hydrogen atoms at the same time; or (IA)

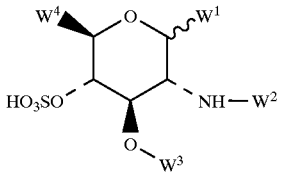

wherein $W^1$ represents a hydrogen atom, a hydroxy group or an alkoxy group of from 1 to 4 carbon atom(s);

$W^2$ represents a group represented by A, B, D or E:

A represents a formula:

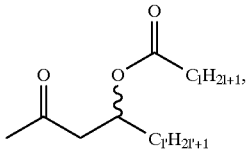

B represents a formula:

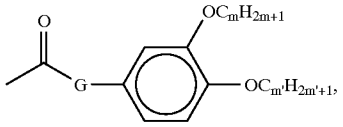

D represents a formula:

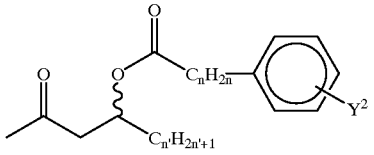

and

E represents a formula:

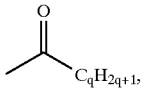

in each of A, B, D and E, l and q each represents an integer of 11~15, m and m' each represents an integer of 6~12, n represents an integer of 6–10, l' and n' each represents an integer of 9~13, G represents a single bond or an alkylene group of from 1 to 4 carbon atom(s);

$Y^2$ represents a hydrogen atom, an alkyl or alkoxy group of from 1 to 7 carbon atom(s) or a halogen atom;

$W_3$ represents a group represented by L, M or Q:

L represents a formula:

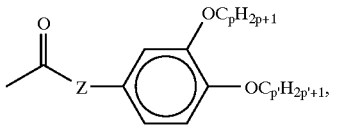

M represents a formula:

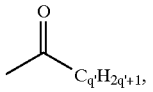

and

Q represents a formula:

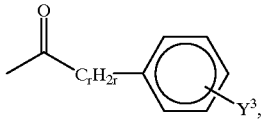

in each of L, M and Q, Z represents a single bond or an alkylene group of from 1 to 4 carbon atom(s), p and p' each represents an integer of 6~12, q' represents an integer of 11~15, r represents an integer of 6~10, $Y^3$ represents a hydrogen atom, an alkyl or alkoxy group of from 1 to 7 carbon atom(s) or a halogen atom;

$W^4$ represents a hydrogen atom, hydroxymethyl group or sulfoxymethyl group;

with the proviso that when $W^4$ represents hydroxymethyl group, (A,M), (A,Q), (D,M), (D,Q) and (E,M) as the combination of ($W^2$, $W^3$) are excluded, and when $W^4$ represents sulfoxymethyl group, (A,M) and (E,M) as the combination of ($W^2$, $W^3$) are excluded, or a non-toxic salt of the glucopyranose compound.

2. A compound according to claim 1, wherein $R^7$ is a hydroxy group.

3. A compound according to claim 2, wherein R is a hydroxy group.

4. A compound according to claim 3, wherein $R^2$ is a phenyl or phenoxy group, and $R^4$ is a hydrogen atom.

5. A compound according to claim 4, which is selected from the group consisting of 2-deoxy-2-[3R-(4-phenylbutyryloxy)tetradecanoyl]amino-3-O-(4-phenylbutyryl)-4-O-sulfo-D-glucopyranose, 2-deoxy-2-[3S-(5-phenylpentanoyloxy)tetradecanoyl]amino-3-O-(5-phenylpentanoyl)-4-O-sulfo-D-glucopyranose, 2-deoxy-2-[3S-(7-phenylheptanoyloxy)tetradecanoyl]amino-3-O-(7-phenylheptanoyl)-4-O-sulfo-D-glucopyranose, 2-deoxy-2-[3S-(9-phenylnonanoyloxy)tetradecanoyl]amino-3-O-(9-phenylnonanoyl)-4-O-sulfo-D-glucopyranose, 2-deoxy-2-[3S-(10-phenyldecanoyloxy)tetradecanoyl]amino-3-O-(10-phenyldecanoyl)-4-O-sulfo-D-glucopyranose, 2-deoxy-2-[3R-(10-phenyldecanoyloxy)tetradecanoyl]amino-3-O-(10-phenyldecanoyl)-4-O-sulfo-D-glucopyranose, 2-deoxy-2-[3S-(11-phenylundecanoyloxy)tetradecanoyl]amino-3-O-(11-phenylundecanoyl)-4-O-sulfo-D-glucopyranose, 2-deoxy-2-[3S-(13-phenyltridecanoyloxy)tetradecanoyl]amino-3-O-(13-phenyltridecanoyl)-4-O-sulfo-D-glucopyranose, 2-deoxy-2-[3R-(9-phenylnonanoyloxy)tetradecanoyl]amino-3-O-(9-phenylnonanoyl)-4-O-sulfo-D-glucopyranose and 2-deoxy-2-[3S-(8-phenoxyoctanoyloxy)tetradecanoyl]amino-3-O-(8-phenoxyoctanoyl)-4-O-sulfo-D-glucopyranose.

6. A compound according to claim 3, wherein both of $R^2$ and $R^4$ are phenyl groups.

7. A compound according to claim 6, which is selected from the group consisting of 2-deoxy-2-[3R-(9-phenylnonanoyloxy)-9-phenylnonanoyl]amino-3-O-(9-phenylnonanoyl)-4-O-sulfo-D-glucopyranose and 2-deoxy-2-[3S-(9-phenylnonanoyloxy)-9-phenylnonanoyl]amino-3-O-(9-phenylnonanoyl)-4-O-sulfo-D-glucopyranose.

8. A compound according to claim 3, wherein $R^2$ is a phenyl or phenoxy group substituted by one to three alkyl or alkoxy group(s) of from 1 to 7 carbon atom(s) or halogen atom(s).

9. A compound according to claim 8, which is selected from the group consisting of 2-deoxy-2-[3S-[8-(4-methoxyphenyl)octanoyloxy]tetradecanoyl]amino-3-O-[8-(4-methoxyphenyl)octanoyl]-4-O-sulfo-D-glucopyranose, 2-deoxy-2-[3S-[9-(4-chlorophenyl)nonanoyloxy]tetradecanoyl]amino-3-O-[9-(4-chlorophenyl)nonanoyl]-4-O-sulfo-D-glucopyranose, 2-deoxy-2-[3S-[5-(4-pentylphenyl)pentanoyloxy]tetradecanoyl]amino-3-O-[5-(4-pentylphenyl)pentanoyl]-4-O-sulfo-D-glucopyranose, 2-deoxy-2-[3S-[8-(4-chlorophenoxy)octanoyloxy]tetradecanoyl]amino-3-O-[8-(4-chlorophenoxy)octanoyl]-4-O-sulfo-D-glucopyranose and 2-deoxy-2-[3S-[8-(3,5-dichlorophenoxy)octanoyloxy]tetradecanoyl]amino-3-O-[8-(3,5-dichlorophenoxy)octanoyl]-4-O-sulfo-D-glucopyranose.

10. A compound according to claim 3, wherein $R^2$ is a naphthyl or naphthyloxy group.

11. A compound according to claim 10, which is selected from the group consisting of 2-deoxy-2-[3S-[9-(1-naphthyl)nonanoyloxy]tetradecanoyl]amino-3-O-[9-(1-naphthyl)nonanoyl]-4-O-sulfo-D-glucopyranose and 2-deoxy-2-[3S-[9-(2-naphthyl)nonanoyloxy]tetradecanoyl]amino-3-O-[9-(2-naphthyl)nonanoyl]-4-O-sulfo-D-glucopyranose.

12. A compound according to claim 3, wherein $R^1$ is a single bond, $R^2$ is a hydrogen atom and $R^4$ is a naphthyl or naphthyloxy group.

13. A compound according to claim 12, which is selected from the group consisting of 2-deoxy-2-[9-(1-naphthyl)nonanoyl]amino-3-O-[9-(1-naphthyl)nonanoyl]-4-O-sulfo-D-glucopyranose and 2-deoxy-2-[9-(2-naphthyl)nonanoyl]amino-3-O-[9-(2-naphthyl)nonanoyl]-4-O-sulfo-D-glucopyranose.

14. A compound according to claim 2, wherein R is a hydrogen atom.

15. A compound according to claim 14, wherein $R^2$ is a phenyl or phenoxy group, and $R^4$ is a hydrogen atom.

16. A compound according to claim 15, which is selected from the group consisting of 2-deoxy-2-[3R-(9-phenylnonanoyloxy)tetradecanoyl]amino-3-O-(9-phenylnonanoyl)-4-O-sulfo-1,5-anhydro-D-glucitol and 2-deoxy-2-[3R-(8-phenoxyoctanoyloxy)tetradecanoyl]amino-3-O-(8-phenoxyoctanoyl)-4-O-sulfo-1,5-anhydro-D-glucitol.

17. A compound according to claim 14, wherein $R^2$ is a phenyl or phenoxy group substituted by one to three alkyl or alkoxy group(s) of from 1 to 7 carbon atom(s) or halogen atom(s).

18. A compound according to claim 17, which is selected from the group consisting of 2-deoxy-2-[3R-[8-(4-methoxyphenyl)octanoyloxy)tetradecanoyl]amino-3-O-[8-(4-methoxyphenyl)octanoyl]-4-O-sulfo-1,5-anhydro-D-glucitol, 2-deoxy-2-[3R-[8-(4-chlorophenoxy)octanoyloxy]tetradecanoyl]amino-3-O-[8-(4-chlorophenoxy)octanoyl]-4-O-sulfo-1,5-anhydro-D-glucitol and 2-deoxy-2-[3R-[5-(4-pentylphenyl)pentanoyloxy]tetradecanoyl]amino-3-O-[5-(4-pentylphenyl)pentanoyl]-4-O-sulfo-1,5-anhydro-D-glucitol.

19. A compound according to claim 14, wherein $R^2$ is a naphthyl or naphthyloxy group.

20. A compound according to claim 19, which is 2-deoxy-2-[3R-[9-(1-naphthyl)nonanoyloxy]tetradecanoyl]amino-3-O-[9-(1-naphthyl)octanoyl]-4-O-sulfo-1,5-anhydro-D-glucitol.

21. A compound according to claim 2, wherein R is a methoxy group.

22. A compound according to claim 21, which is methyl 2-deoxy-2-[3R-(9-phenylnonanoyloxy)tetradecanoyl]amino-3-O-(9-phenylnonanoyl)-4-O-sulfo-β-D-glucopyranoside.

23. A compound according to claim 1, wherein both of $R^7$ and R are hydrogen atoms.

24. A compound according to claim 23, which is 2,6-deoxy-2-[3S-(9-phenylnonanoyloxy)tetradecanoyl]amino-3-O-(9-phenylnonanoyl)-4-O-sulfo-1,5-anhydro-D-glucitol.

25. A compound according to claim 1, wherein $W^4$ is a hydrogen atom.

26. A compound according to claim 1 or claim 25, wherein $R^2$ is the formula represented by B.

27. A compound according to claim 1 or claim 26, wherein $W_3$ is the formula represented by L.

28. A compound according to claim 1 or claim 27, which is selected from the group consisting of 2-deoxy-2-(3-tetradecanoyloxytetradecanoyl)amino-3-O-tetradecanoyl-4-O-sulfo-1,5-anhydro-D-xylitol, 2-deoxy-2-[3-(9-phenylnonanoyl)oxytetradecanoyl]amino-3-O-(9-phenylnonanoyl)-4-O-sulfo-1,5-anhydro-D-xylitol, 2-deoxy-2-(3,4-didecyloxybenzoyl)amino-3-O-tetradecanoyl-4-O-sulfo-1,5-anhydro-D-xylitol, methyl 2-deoxy-2-(3,4-didecyloxybenzoyl)amino-3-O-tetradecanoyl-4-O-sulfo-5-anhydro-D-glucopyranoside, 2-deoxy-2-(3,4-didecyloxybenzoyl)amino-3-O-tetradecanoyl-4-O-sulfo-D-glucopyranose, 2-deoxy-2-(3,4-didecyloxybenzoyl)amino-3-O-(3,4-didecyloxybenzoyl)-4-O-sulfo-D-glucopyranose, methyl 2-deoxy-2-(3,4-didecyloxybenzoyl)amino-3-O-(3,4-didecyloxybenzoyl)-4,6-disulfo-α-D-glucopyranoside, methyl 2-deoxy-2-(3,4-didecyloxybenzoyl)amino-3-O-(3,4-didecyloxybenzoyl)-4-O-sulfo-α-D-glucopyranoside, 2-deoxy-2-(3,4-didecyloxybenzoyl)amino-3-O-tetradecanoyl-4,6-O-disulfo-D-glucopyranoside, methyl 2-deoxy-2-(3,4-didecyloxybenzoyl)amino-3-O-tetradecanoyl-4-O-sulfo-D-glucopyranoside, 2-deoxy-2-tetradecanoylamino-3-O-(3,4-didecyloxybenzoyl)-4-O-sulfo-D-glucopyranose, 2-deoxy-2-[3-(3,4-dioctyloxy)phenylpropionyl]amino-3-O-tetradecanoyl-4-O-sulfo-D-glucopyranose, methyl 2-deoxy-2-[3-(3,4-dioctyloxyphenyl)propanoyl]amino-3-O-[3-(3,4-dioctyloxyphenyl)propanoyl]-4,6-disulfo-α-D-glucopyranoside, methyl 2-deoxy-2-[3-(3,4-dioctyloxyphenyl)propanoyl]amino-3-O-tetradecanoyl-4,6-O-disulfo-α-D-glucopyranoside and methyl 2-deoxy-2-tetradecanoylamino-3-O-[3-(3,4-dioctyloxyphenyl)propanoyl]-4,5-O-disulfo-α-D-glucopyranoside.

29. A pharmaceutical composition for use in enhancing immunity, or in the treatment of a tumor comprising as active ingredient, a compound of the formula (I) or (IA) as set forth in claim 1, with a pharmaceutically acceptable carrier and/or coating.

* * * * *